US008642557B2

(12) United States Patent
Akamatsu et al.

(10) Patent No.: US 8,642,557 B2

(45) Date of Patent: Feb. 4, 2014

(54) CTLA4 PROTEINS AND THEIR USES

(75) Inventors: Yoshiko Akamatsu, Palo Alto, CA (US); Veronica Juan, Redwood City, CA (US); Robert B. Dubridge, Belmont, CA (US)

(73) Assignee: Abbvie Biotherapeutics Inc., Redwood City, CA (US)

( * ) Notice: Subject to any disclaimer, the term of this patent is extended or adjusted under 35 U.S.C. 154(b) by 0 days.

(21) Appl. No.: 13/046,498

(22) Filed: Mar. 11, 2011

(65) Prior Publication Data

US 2011/0305712 A1 Dec. 15, 2011

Related U.S. Application Data

(60) Provisional application No. 61/313,516, filed on Mar. 12, 2010.

(51) Int. Cl.
*A61K 38/16* (2006.01)

(52) U.S. Cl.
USPC .......................................................... 514/21.2

(58) Field of Classification Search
None
See application file for complete search history.

(56) References Cited

U.S. PATENT DOCUMENTS

| | | | |
|---|---|---|---|
| 5,770,197 | A | 6/1998 | Linsley et al. |
| 5,977,318 | A | 11/1999 | Linsley et al. |
| 6,090,914 | A | 7/2000 | Linsley et al. |
| 6,107,056 | A | 8/2000 | Oaks |
| 6,750,334 | B1 | 6/2004 | Gray et al. |
| 7,030,225 | B1 | 4/2006 | Tamatani et al. |
| 7,034,121 | B2 | 4/2006 | Carreno et al. |
| 7,105,166 | B1 | 9/2006 | Linsley et al. |
| 7,229,962 | B2 | 6/2007 | Chung et al. |
| 7,304,033 | B2 | 12/2007 | Larsen et al. |
| 7,385,045 | B2 | 6/2008 | Yang et al. |
| 7,432,344 | B1 | 10/2008 | Lechler et al. |
| 7,482,327 | B2 | 1/2009 | Hagerty et al. |
| 7,504,554 | B2 | 3/2009 | Liu et al. |
| 7,541,164 | B2 | 6/2009 | Schilling et al. |
| 2004/0014171 | A1 | 1/2004 | Peach et al. |
| 2009/0186097 | A1 | 7/2009 | Ayares |
| 2009/0258031 | A1 | 10/2009 | Karrer et al. |
| 2011/0287032 | A1* | 11/2011 | Lazar et al. ................ 424/178.1 |

FOREIGN PATENT DOCUMENTS

| | | | |
|---|---|---|---|
| WO | WO 01/30966 | A4 | 5/2001 |
| WO | WO 01/92337 | A2 | 12/2001 |
| WO | WO 02/02638 | A2 | 1/2002 |
| WO | WO 2005/014612 | A1 | 2/2005 |
| WO | WO 2005/108432 | A2 | 11/2005 |
| WO | WO 2008/047150 | A2 | 4/2008 |
| WO | WO 2009/058564 | A2 | 5/2009 |
| WO | WO 2011/103584 | A2 | 8/2011 |

OTHER PUBLICATIONS

Larsen et al., American Journal of Transplantation, 2005; 5: 443-453.*
Akamatsu et al., "Whole IgG surface display on mammalian cells: Application to isolation of neutralizing chicken monoclonal anti-IL-12 antibodies," J. Immunol. Methods, 327, 40-52 (2007).
van den Beucken et al., "building novel binding ligands to B7.1 and B7.2 based on human antibody single variable light chain domains," J. Mol. Biol., 310, 591-601 (2001).
Davis et al., "Abatacept binds to the Fc receptor CD64 but does not mediate complement-dependent cytotoxicity or antibody-dependent cellular cytotoxicity," J. Rheumatol., 34, 2204-2210 (2007).
Fukumoto et al., "Peptide mimics of the CTLA4-binding domain stimulate T-cell proliferation," Nature Biotechnology, 16, 267-270 (1998).
Greenwald et al., "Effects of blocking B7-1 and B7-2 interactions during a type 2 in vivo immune response," J. Immunol., 158, 4088-4096 (1997).
International Search Report corresponding to related International Application No. PCT/US2011/028221 dated Dec. 16, 2011.
Larsen et al., "Rational development of LEA29Y (belatacept), a high-affinity variant of CTLA-4-lg with potent immunosuppressive properties," Amer. J. Transplantation, 5, 443-453 (2005).
Li et al., "The protein-protein interface evolution acts in a similar way to antibody affinity maturation," J. Biol. Chem., 285, 3865-3871 (2010).
Linsley et al., "The Clinical Utility of Inhibiting CD28—Mediated Costimulation," Immunol. Rev., 229, 307-321 (2009).
Linsley et al., "Human B7-1 (CD80) and B7-2 (CD86) bind with similar avidities but distinct kinetics to CD28 and CTLA-4 receptors," Immunity, 1, 793-801 (1994).
McIntyre et al., "Treatment of Transplant Rejection," Drugs of the Future, 30, 873-876 (2005).
Metzler et al., "Solution structure of human CTLA-4 and delineation of a CD90/CD86 binding site conserved in CD28," Nat. Strct. Biol., 4, 527-531 (1997).
Morton et al., "Differential effects of CTLA-4 substitutions on the binding of Human CD80 (B7-1) and CD86 (B7-2)," J. Immunol., 156, 1047-1054 (1996).
Nuttal et al., "Design and expression of soluble CTLA-4 variable domain as a scaffold for the display of functional polypeptides," Proteins: Structure, Function and Genetics, 36, 217-227 (1999).
Osei-Hyiaman et al., "Association of a novel point mutation (C159G) of the CTLA4 gene with Type 1 Diabetes in West Africans but not in Chinese," Diabetes, 50, 2169-2171 (2001).
Peach et al., "Complementarity determining Region 1 (CDR1)- and CDR3-analogous regions in CTLA-4 and CD28 determine the binding to B7-1," J. Exp. Med., 180, 2049-2058 (1994).
Peggs et al., "Principles and uses of anti-CTLA4 antibody in human cancer immunotherapy," Current Opinion in Immunol., 18, 206-213 (2006).
Salomon et al., "Complexities of CD28/B7: CTLA-4 costimulatory pathways in autoimmunity and transplantation," Annu. Rev. Immunol., 19, 225-252 (2001).
Schwartz, "Costimulation of T lymphocytes: The role of CD28, CTLA-4, and B7/BB1 in interleukin-1 production and immunotherapy," Cell, 71, 1065-1068 (1992).

(Continued)

*Primary Examiner* — Ilia Ouspenski
(74) *Attorney, Agent, or Firm* — Dechert LLP

(57) ABSTRACT

The present disclosure relates to CTLA4 proteins and uses of such proteins, for example to treat diseases associated with the dysregulation of immune responses.

43 Claims, 27 Drawing Sheets

(56) References Cited

OTHER PUBLICATIONS

Truneh et al., "Differential recognition by CD28 of its cognate counter receptors CD80 (B7.1) and B70 (B7.2) analysis by site directed mutagenesis," Mol. Immunol., 33, 321-334 (1996).

Vaughan et al., "Porcine CTLA4-lg lacks a MYPPPY Motif, binds inefficiently to Human B7 and specifically suppresses Human $CD4^{+}$T Cell responses costimulated by pig but not Human B7," J. Immunol., 165, 3175-3181 (2000).

* cited by examiner

```
            1           2           3           4
 123456789  0123456789  0123456789  0123456789  0123456789
 MHVAQPAVV  LASSRGIASF  VCEYASPGKA  TEVRVTVLRQ  ADSQVTEVCA

5           6           7           8           9
0123456789  0123456789  0123456789  0123456789  0123456789
ATYMMGNELT  FLDDSICTGT  SSGNQVNLTI  QGLRAMDTGL  YICKVELMYP

1           1           1
0           1           2
0123456789  0123456789  01234
PPYYLGIGNG  TQIYVIDPEP  CPDSD
```

FIGURE 1A

| CDR-like loop No. | Sequence | SEQ ID NO. |
|---|---|---|
| 1 | PGKATEVR | 2 |
| 2 | TYMMGNELTFLDD | 3 |
| 3 | KVELMYPPPYYL | 4 |

FIGURE 1B

```
                       1          2          3          4
             123456789 0123456789 0123456789 0123456789 0123456789
hCTLA-4      MHVAQPAVV LASSRGIASF VCEYASPGKA TEVRVTVLRQ ADSQVTEVCA
Abatacept    MHVAQPAVV LASSRGIASF VCEYASPGKA TEVRVTVLRQ ADSQVTEVCA

            5          6          7          8          9
            0123456789 0123456789 0123456789 0123456789 0123456789
hCTLA-4     ATYMMGNELT FLDDSICTGT SSGNQVNLTI QGLRAMDTGL YICKVELMYP
Abatacept   ATYMMGNELT FLDDSICTGT SSGNQVNLTI QGLRAMDTGL YICKVELMYP

            1          1          1          1          1
            0          1          2          3          4
            0123456789 0123456789 0123456789 0123456789 0123456789
hCTLA-4     PPYYLGIGNG TQIYVIDPEP CPDSDFLLWI LAAVSSGLFF YSFLLTAVSL
Abatacept   PPYYLGIGNG TQIYVIDPEP CPDSDQEPKS SDKTHTSPPS PAPELLGGSS
Human Fcγ1                             VEPKS CDKTHTCPPC PAPELLGGPS

            1          1          1          1          1
            5          6          7          8          9
            0123456789 0123456789 0123456789 0123456789 0123456789
hCTLA-4     SKMLKKRSPL TTGVYVKMPP TEPECEKQFQ PYFIPIN
Abatacept   VFLFPPKPKD TLMISRTPEV TCVVVDVSHE DPEVKFNWYV DGVEVHNAKT
Human Fcγ1  VFLFPPKPKD TLMISRTPEV TCVVVDVSHE DPEVKFNWYV DGVEVHNAKT

            2          2          2          2          2
            0          1          2          3          4
            0123456789 0123456789 0123456789 0123456789 0123456789
Abatacept   KPREEQYNST YRVVSVLTVL HQDWLNGKEY KCKVSNKALP APIEKTISKA
Human Fcγ1  KPREEQYNST YRVVSVLTVL HQDWLNGKEY KCKVSNKALP APIEKTISKA

            2          2          2          2          2
            5          6          7          8          9
            0123456789 0123456789 0123456789 0123456789 0123456789
Abatacept   KGQPREPQVY TLPPSRDELT KNQVSLTCLV KGFYPSDIAV EWESNGQPEN
Human Fcγ1  KGQPREPQVY TLPPSRDELT KNQVSLTCLV KGFYPSDIAV EWESNGQPEN

            3          3          3          3          3
            0          1          2          3          4
            0123456789 0123456789 0123456789 0123456789 0123456789
Abatacept   NYKTTPPVLD SDGSFFLYSK LTVDKSRWQQ GNVFSCSVMH EALHNHYTQK
Human Fcγ1  NYKTTPPVLD SDGSFFLYSK LTVDKSRWQQ GNVFSCSVMH EALHNHYTQK

            3
            5
            01234567
Abatacept   SLSLSPGK
Human Fcγ1  SLSLSPGK
```

FIGURE 1C

| CDR-like Loop No. | Residue | Position in CDR-like Loop | Position in Polypeptide Chain |
|---|---|---|---|
| 1 (SEQ ID NO: 2) | P | 1 | 26 |
| | G | 2 | 27 |
| | K | 3 | 28 |
| | A | 4 | 29 |
| | T | 5 | 30 |
| | E | 6 | 31 |
| | V | 7 | 32 |
| | R | 8 | 33 |
| 2 (SEQ ID NO: 3) | T | 1 | 51 |
| | Y | 2 | 52 |
| | M | 3 | 53 |
| | M | 4 | 54 |
| | G | 5 | 55 |
| | N | 6 | 56 |
| | E | 7 | 57 |
| | L | 8 | 58 |
| | T | 9 | 59 |
| | F | 10 | 60 |
| | L | 11 | 61 |
| | D | 12 | 62 |
| | D | 13 | 63 |
| 3 (SEQ ID NO: 4) | K | 1 | 93 |
| | V | 2 | 94 |
| | E | 3 | 95 |
| | L | 4 | 96 |
| | M | 5 | 97 |
| | Y | 6 | 98 |
| | P | 7 | 99 |
| | P | 8 | 100 |
| | P | 9 | 101 |
| | Y | 10 | 102 |
| | Y | 11 | 103 |
| | L | 12 | 104 |

Figure 7

| WT | Position in Polypeptide Chain/Position in CDR-like Loop | High affinity substitutions for CD80 and CD86 binding | SEQ ID NO: |
|---|---|---|---|
| CDR-like Loop 1 | | | |
| K | 28/3 | H, T | 8,9 |
| A | 29/4 | H | 10 |
| CDR-like Loop 2 | | | |
| T | 51/1 | Y | 11 |
| M | 53/3 | F, Y | 12,13 |
| L | 58/8 | G | 14 |
| L | 61/11 | H, Y | 15,16 |
| CDR-like Loop 3 | | | |
| K | 93/1 | M, Q | 17,18 |

Figure 8

| WT | Position in Polypeptide Chain/Position in CDR-like Loop | High affinity substitutions for CD80 *binding/* Neutral substitutions for CD86 binding | SEQ ID NO: |
|---|---|---|---|
| CDR-like Loop 2 | | | |
| L | 58/8 | A, N, Q | 19,21 |
| L | 61/11 | A | 22 |
| CDR-like Loop 3 | | | |
| K | 93/1 | V | 23 |
| L | 104/12 | H, Y | 24,.25 |

Figure 9

| WT | Position in Polypeptide Chain/Position in CDR-like Loop | Candidate high affinity substitutions for CD80 binding/ Neutral substitutions for CD86 binding | SEQ ID NO: |
|---|---|---|---|
| CDR-like Loop 1 | | | |
| T | 30/5 | E | 26 |
| CDR-like Loop 2 | | | |
| M | 54/4 | R | 27 |
| G | 55/5 | P | 28 |
| E | 57/7 | P | 29 |
| L | 58/8 | E, P, Y | 30, 31, 32 |
| L | 61/11 | F | 33 |
| CDR-like Loop 3 | | | |
| L | 104/12 | I | 34 |

Figure 10

| WT | Position in Polypeptide Chain/Position in CDR-like Loop | High affinity substitutions for CD80 binding/ Low affinity substitutions for CD86 binding | SEQ ID NO: |
|---|---|---|---|
| CDR-like Loop 3 | | | |
| K | 93/1 | I | 35 |

Figure 11

| WT | Position in Polypeptide Chain/Position in CDR-like Loop | Candidate high affinity substitutions for CD80 binding/ Low affinity substitutions for CD86 *binding* | SEQ ID NO: |
|---|---|---|---|
| CDR-like Loop 2 | | | |
| L | 58/8 | H, K | 36, 37 |
| D | 62/12 | H | 38 |

Figure 12

| WT | Position in Polypeptide Chain/Position in CDR-like Loop | Neutral substitutions for CD80 binding/ High affinity substitutions for CD86 binding | SEQ ID NO: |
|---|---|---|---|
| CDR-like Loop 2 | | | |
| M | 54/4 | W, Y | 39, 40 |

Figure 13

| WT | Position in Polypeptide Chain/Position in CDR-like Loop | Candidate neutral substitutions for CD80 binding/ High affinity substitutions for CD86 binding | SEQ ID NO: |
|---|---|---|---|
| CDR-like Loop 1 | | | |
| R | 33/8 | D | 41 |
| CDR-like Loop 2 | | | |
| L | 61/11 | W | 42 |

Figure 14

| WT | Position in Polypeptide Chain/Position in CDR-like Loop | Low affinity substitutions for CD80 binding/ High affinity substitutions for CD86 binding | SEQ ID NO: |
|---|---|---|---|
| CDR-like Loop 1 | | | |
| A | 29/4 | K | 43 |
| CDR-like Loop 2 | | | |
| T | 51/1 | N | 44 |
| M | 53/3 | W | 45 |
| CDR-like Loop 3 | | | |
| L | 96/4 | K, R | 46, 47 |

Figure 15

| WT | Position in Polypeptide Chain/Position in CDR-like Loop | Neutral substitutions for CD80 and CD86 binding | SEQ ID NO: |
|---|---|---|---|
| CDR-like Loop 1 | | | |
| G | 27/2 | A | 48 |
| CDR-like Loop 2 | | | |
| Y | 52/2 | F | 49 |
| N | 56/6 | T | 50 |
| CDR-like Loop 3 | | | |
| L | 104/12 | M | 51 |

Figure 16

| WT | Position in Polypeptide Chain/Position in CDR-like Loop | Candidate neutral substitutions for CD80 and CD86 binding | SEQ ID NO: |
|---|---|---|---|
| CDR-like Loop 1 | | | |
| P | 26/1 | I, L, M, Q, T, V | 52, 53, 54, 55, 56, 57 |
| K | 28/3 | R | 58 |
| A | 29/4 | P, S | 59, 60 |
| T | 30/5 | H, M, S | 61, 63 |
| V | 32/7 | E | 64 |
| R | 33/8 | P | 65 |
| CDR-like Loop 2 | | | |
| T | 51/1 | A | 66 |
| Y | 52/2 | H, M, W | 67, 68, 69 |
| M | 53/3 | D | 70 |
| M | 54/4 | D, G, H, L | 71, 72, 73, 74 |
| G | 55/5 | D, H, T | 75, 76, 77 |
| N | 56/6 | A, F, G, H, I, K, L, M, Q, R, S, V, Y | 78 to 90, respectively |
| E | 57/7 | A, D, H, K, M, N, Q, R, S, T, V | 91 to 101, respectively |
| L | 58/8 | I, R, T | 102, 103, 104 |
| T | 59/9 | I, M, N, Q, R, S, V | 105 to 111, respectively |
| L | 61/11 | E, I, M, T, V | 112, 113, 114, 115, 116 |
| D | 62/12 | R | 117 |
| D | 63/13 | E, G, H, T | 118, 119, 120, 121 |
| CDR-like Loop 3 | | | |
| K | 93/1 | G | 122 |
| V | 94/2 | G, I | 123, 124 |
| E | 95/3 | W | 125 |
| P | 99/7 | H, T, L | 126, 127, 128 |
| Y | 102/10 | T | 129 |

Figure 17

| WT | Position in Polypeptide Chain/Position in CDR-like Loop | Neutral substitutions for CD80 binding/ low affinity substitutions for CD86 binding | SEQ ID NO: |
|---|---|---|---|
| CDR-like Loop 1 | | | |
| K | 28/3 | Y | 130 |

Figure 18

| WT | Position in Polypeptide Chain/Position in CDR-like Loop | Candidate neutral substitutions for CD80 binding/ low affinity substitutions for CD86 binding | SEQ ID NO: |
|---|---|---|---|
| CDR-like Loop 1 | | | |
| P | 26/1 | N | 131 |
| G | 27/2 | I, Q, W | 132, 133, 134 |
| K | 28/3 | E, I, M, P, Q, V | 135 to 140, respectively |
| T | 30/5 | I, L | 141, 142 |
| CDR-like Loop 2 | | | |
| M | 53/3 | E, L, N | 143, 144, 145 |
| M | 54/4 | A, Q, S | 146, 147, 148 |
| L | 58/8 | D, V | 149, 150 |
| T | 59/9 | H, K, L, P | 151, 152, 153, 154 |
| L | 61/11 | D, G, Q, R | 155, 156, 157, 158 |
| D | 62/12 | A, E, S | 159, 160, 161 |
| D | 63/13 | Q, S | 162, 163 |
| CDR-like Loop 3 | | | |
| K | 93/1 | R | 164 |

Figure 19

| WT | Position in Polypeptide Chain/Position in CDR-like Loop | Candidate low affinity substitutions for CD80 binding/ Neutral substitutions for CD86 binding | SEQ ID NO: |
|---|---|---|---|
| CDR-like Loop 1 | | | |
| P | 26/1 | R | 165 |
| G | 27/2 | D, P | 166, 167 |
| A | 29/4 | N | 168 |
| T | 30/5 | K | 169 |
| E | 31/6 | D, G, P, R, T | 170, 171, 172, 173, 174 |
| V | 32/7 | G, H, T | 175, 176, 177 |
| R | 33/8 | E, G, I, M, N, Q, W, Y | 178 to 185, respectively |
| CDR-like Loop 2 | | | |
| T | 51/1 | E, G, I, V | 186, 187, 188, 189 |
| Y | 52/2 | A, D, I, K, L, Q, R, S, T | 190 to 198, respectively |
| M | 53/3 | H, P, S | 199, 200, 201 |
| G | 55/5 | A, I, L, N, Q, R, Y | 202 to 208, respectively |
| E | 57/7 | G, I, W, Y | 209, 210, 211, 212 |
| T | 59/9 | D, G, Y | 213, 214, 215 |
| F | 60/10 | D, G, H, L | 216, 217, 218, 219 |
| D | 62/12 | G, I, W | 220, 221, 222 |
| D | 63/13 | A, Y | 223, 224 |
| CDR-like Loop 3 | | | |
| K | 93/1 | D, H, N, P, W | 225, 226, 227, 228, 229 |
| V | 94/2 | A, D, H, N, P, R, T, W | 230 to 237, respectively |
| E | 95/3 | G, I, K, P, Q, R, S, T, V, Y | 238 to 247, respectively |
| L | 96/4 | A, G, H, M, P, Q | 248 to 253, respectively |
| M | 97/5 | D, G, I, N, S, V | 254 to 259, respectively |
| P | 99/7 | I, M, W, Y | 260, 261, 262, 263 |
| P | 100/8 | H, L, T, V, W | 264, 265, 266, 267, 268 |
| P | 101/9 | L | 269 |
| Y | 102/10 | H | 270 |
| Y | 103/11 | H, L, P, T | 271, 272, 273, 274 |
| L | 104/12 | P | 275 |

Figure 20

| Row # | WT | Position in Polypeptide Chain/Position in CDR-like Loop | Substitutions | SEQ ID NO: |
|---|---|---|---|---|
| | | CDR-like Loop 3 | | |
| 1 | L | 104/12 | E | 276 |
| | | CDR-like Loop 1 | | |
| 2 | G | 27/2 | H, T | 277, 278 |
| 3 | K | 28/3 | G, N, S | 279, 280, 281 |
| | | CDR-like Loop 2 | | |
| 4 | M | 54/4 | K | 282 |
| 5 | L | 61/11 | P | 283 |
| | | CDR-like Loop 1 | | |
| 6 | G | 27/2 | S | 284 |
| | | CDR-like Loop 1 | | |
| 7 | A | 29/4 | T, W, Y | 285, 286, 287 |
| | | CDR-like Loop 2 | | |
| 8 | T | 51/1 | S | 288 |
| | | CDR-like Loop 1 | | |
| 9 | T | 30/5 | G | 289 |
| | | CDR-like Loop 1 | | |
| 10 | P | 26/1 | H, K, S | 290, 291, 292 |
| 11 | A | 29/4 | G, V | 293, 294 |
| 12 | T | 30/5 | A, D, N, Q, Y | 295, 296, 297, 298, 299 |
| | | CDR-like Loop 2 | | |
| 13 | M | 53/3 | V, I | 300-301 |
| 14 | M | 54/4 | V | 302 |
| 15 | G | 55/5 | E | 303 |
| 16 | N | 56/6 | D | 304 |
| 17 | L | 58/8 | S | 305 |
| 18 | T | 59/9 | A | 306 |
| 19 | D | 62/12 | N | 307 |
| | | CDR-like Loop 3 | | |
| 20 | K | 93/1 | E | 308 |
| 21 | Y | 98/6 | I | 309 |
| 22 | L | 104/12 | Q, W | 310-311 |

Figure 21

| Row # | WT | Position in Polypeptide Chain/Position in CDR-like Loop | Substitutions | SEQ ID NO: |
|---|---|---|---|---|
| CDR-like Loop 1 | | | | |
| 23 | P | 26/1 | A | 312 |
| 24 | G | 27/2 | V | 313 |
| 25 | K | 28/3 | A, D | 314-315 |
| 26 | V | 32/7 | I | 316 |
| CDR-like Loop 1 | | | | |
| 27 | G | 27/2 | R | 317 |
| 28 | A | 29/4 | Q | 318 |
| 29 | T | 30/5 | R | 319 |
| CDR-like Loop 2 | | | | |
| 30 | D | 63/13 | K | 320 |
| CDR-like Loop 3 | | | | |
| 31 | K | 93/1 | S | 321 |
| 32 | Y | 98/6 | P | 322 |
| 33 | P | 100/8 | A | 323 |
| 34 | L | 104/12 | D, S, V | 324, 325, 326 |

Figure 21, continued

| SEQ ID NO: | 26 | 27 | 28 | 29 | 30 | 31 | 32 | 33 | SEQ ID NO: | 51 | 52 | 53 | 54 | 55 | 56 | 57 | 58 | 59 | 60 | 61 | 62 | 63 | SEQ ID NO: | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|
| 2 | P | G | K | A | T | E | V | R | 3 | T | Y | M | M | G | N | E | L | T | F | L | D | D | 4 | K | V | E | L | M | Y | P | P | P | Y | Y | L |
| 327 | | | | | | S | | | 3 | | | | | | | | | | | | | | 4 | | | | | | | | | | | | |
| 328 | | | | | | | | S | 3 | | | | | | | | | | | | | | 4 | | | | | | | | | | | | |
| 2 | | | | | | | | | 331 | S | | | | | | | | | | | | | 4 | | | | | | | | | | | | |
| 2 | | | | | | | | | 3 | | | | | | | | | | | | | | 333 | S | | | | | | | | | | | |
| 2 | | | | | | | | | 3 | | | | | | | | | | | | | | 334 | | | | | | P | | | | | | |
| 2 | | | | | | | | | 3 | | | | | | | | | | | | | | 335 | | | | | | | | | | P | | |
| 2 | | | | | | | | | 3 | | | | | | | | | | | | | | 336 | A | | A | | | | | | | | | |
| 2 | | | | | | | | | 3 | | | | | | | | | | | | | | 337 | | | | | A | | | | | | | |
| 2 | | | | | | | | | 3 | | | | | | | | | | | | | | 338 | | | | | | A | | | | | | |
| 2 | | | | | | | | | 3 | | | | | | | | | | | | | | 339 | | | | | | | A | | | | | |
| 2 | | | | | | | | | 3 | | | | | | | | | | | | | | 340 | | | | | | | | A | | | | |
| 2 | | | | | | | | | 3 | | | | | | | | | | | | | | 341 | | | | | | | | | A | | | |
| 2 | | | | | | | | | 3 | | | | | | | | | | | | | | 342 | | | | | | | | | | A | | |
| 2 | | | | | | | | | 3 | | | | | | | | | | | | | | 343 | | | | | A | A | A | A | A | A | | |
| 329 | | | A | | | A | | A | 3 | | | | | | | | | | | | | | 4 | | | | | | | | | | | | |
| 2 | | | | | | | | | 332 | | | I | | | | | | | | | | | 4 | | | | | | | | | | | | |
| 330 | | | | Y | | | | | 3 | | | | | | | | | | | | | | 344 | | | | | | | | | | | | E |
| 2 | | | | | | | | | 3 | | | | | | | | | | | | | | 345 | | | | | | F | | | | | | |

Figure 22-1

| SEQ ID NO: | 26 | 27 | 28 | 29 | 30 | 31 | 32 | 33 | SEQ ID NO: | 51 | 52 | 53 | 54 | 55 | 56 | 57 | 58 | 59 | 60 | 61 | 62 | 63 | SEQ ID NO: | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|
| 2 | P | G | K | A | T | E | V | R | 3 | T | Y | M | M | G | N | E | L | T | F | L | D | D | 4 | K | V | E | L | M | Y | P | P | P | Y | Y | L |
| 2 | | | | | | | | | 3 | | | | | | | | | | | | | | 355 | | | | | | | | | | | | E |
| 2 | | | | | | | | | 3 | | | | | | | | | | | | | | 356 | | | | | | | | | | | | S |
| 2 | | | | | | | | | 3 | | | | | | | | | | | | | | 357 | | | | | | | | | | | | T |
| 2 | | | | | | | | | 3 | | | | | | | | | | | | | | 358 | | | | | | | | | | | | A |
| 2 | | | | | | | | | 3 | | | | | | | | | | | | | | 359 | | | | | | | | | | | | W |
| 2 | | | | | | | | | 3 | | | | | | | | | | | | | | 360 | | | | | | | | | | | | Q |
| 2 | | | | | | | | | 3 | | | | | | | | | | | | | | 361 | | | | | | | | | | | | K |
| 2 | | | | | | | | | 3 | | | | | | | | | | | | | | 362 | | | | | | | | | | | | R |
| 2 | | | | | | | | | 3 | | | | | | | | | | | | | | 363 | | | | | | | | | | | | G |
| 2 | | | | | | | | | 3 | | | | | | | | | | | | | | 364 | | | | | | | | | | | | D |
| 346 | | | | | G | | | | 3 | | | | | | | | | | | | | | 365 | | | | | | | | | | | | E |
| 347 | | | | | N | | | | 3 | | | | | | | | | | | | | | 365 | | | | | | | | | | | | E |
| 348 | | | | Y | | | | | 3 | | | | | | | | | | | | | | 365 | | | | | | | | | | | | E |
| 349 | | | | L | | | | | 3 | | | | | | | | | | | | | | 365 | | | | | | | | | | | | E |
| 350 | | | | W | | | | | 3 | | | | | | | | | | | | | | 365 | | | | | | | | | | | | E |
| 351 | | | | T | | | | | 3 | | | | | | | | | | | | | | 365 | | | | | | | | | | | | E |
| 352 | K | R | G | V | Q | | | | 3 | | | | | | | | | | | | | | 4 | | | | | | | | | | | | |
| 353 | Y | T | G | Y | G | | | | 3 | | | | | | | | | | | | | | 4 | | | | | | | | | | | | |
| 354 | Y | R | N | Q | Q | | | | 3 | | | | | | | | | | | | | | 4 | | | | | | | | | | | | |

Figure 22-2

| SEQ ID NO: | 26 | 27 | 28 | 29 | 30 | 31 | 32 | 33 | SEQ ID NO: | 51 | 52 | 53 | 54 | 55 | 56 | 57 | 58 | 59 | 60 | 61 | 62 | 63 | SEQ ID NO: | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|
| 2 | P | G | K | A | T | E | V | R | 3 | T | Y | M | M | G | N | E | L | T | F | L | D | D | 4 | K | V | E | L | M | Y | P | P | P | Y | Y | L |
| 366 | P | Y | D | G | Q | | | | 3 | | | | | | | | | | | | | | 4 | | | | | | | | | | | | |
| 367 | H | V | S | R | R | | | | 3 | | | | | | | | | | | | | | 4 | | | | | | | | | | | | |
| 2 | | | | | | | | | 3 | | | | | | | | | | | | | | 368 | | | | | A | | | | | | | |
| 2 | | | | | | | | | 3 | | | | | | | | | | | | | | 369 | | | | | | A | | | | | | |
| 2 | | | | | | | | | 3 | | | | | | | | | | | | | | 370 | | | | | | | A | | | | | |
| 2 | | | | | | | | | 3 | | | | | | | | | | | | | | 371 | | | | | | | | A | | | | |
| 2 | | | | | | | | | 3 | | | | | | | | | | | | | | 372 | | | | | | | | | A | | | |
| 2 | | | | | | | | | 3 | | | | | | | | | | | | | | 373 | | | | | | | | | | A | | |
| 2 | | | | | | | | | 3 | | | | | | | | | | | | | | 374 | | | | | | D | | | | | | |
| 2 | | | | | | | | | 3 | | | | | | | | | | | | | | 375 | | | | | | E | | | | | | |
| 2 | | | | | | | | | 3 | | | | | | | | | | | | | | 376 | | | | | | F | | | | | | |
| 2 | | | | | | | | | 3 | | | | | | | | | | | | | | 377 | | | | | | G | | | | | | |
| 2 | | | | | | | | | 3 | | | | | | | | | | | | | | 378 | | | | | | H | | | | | | |
| 2 | | | | | | | | | 3 | | | | | | | | | | | | | | 379 | | | | | | I | | | | | | |
| 2 | | | | | | | | | 3 | | | | | | | | | | | | | | 380 | | | | | | K | | | | | | |
| 2 | | | | | | | | | 3 | | | | | | | | | | | | | | 381 | | | | | | L | | | | | | |
| 2 | | | | | | | | | 3 | | | | | | | | | | | | | | 382 | | | | | | M | | | | | | |
| 2 | | | | | | | | | 3 | | | | | | | | | | | | | | 383 | | | | | | N | | | | | | |
| 2 | | | | | | | | | 3 | | | | | | | | | | | | | | 384 | | | | | | P | | | | | | |

Figure 22-3

| SEQ ID NO: | 26 | 27 | 28 | 29 | 30 | 31 | 32 | 33 | SEQ ID NO: | 51 | 52 | 53 | 54 | 55 | 56 | 57 | 58 | 59 | 60 | 61 | 62 | 63 | SEQ ID NO: | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|
| 2 | P | G | K | A | T | E | V | R | 3 | T | Y | M | M | G | N | E | L | T | F | L | D | D | 4 | K | V | E | L | M | Y | P | P | P | Y | Y | L |
| 2 | | | | | | | | | 3 | | | | | | | | | | | | | | 401 | | | | | | Q | | | | | | |
| 2 | | | | | | | | | 3 | | | | | | | | | | | | | | 402 | | | | | | R | | | | | | |
| 2 | | | | | | | | | 3 | | | | | | | | | | | | | | 403 | | | | | | S | | | | | | |
| 2 | | | | | | | | | 3 | | | | | | | | | | | | | | 404 | | | | | | T | | | | | | |
| 2 | | | | | | | | | 3 | | | | | | | | | | | | | | 405 | | | | | | V | | | | | | |
| 2 | | | | | | | | | 3 | | | | | | | | | | | | | | 406 | | | | | | W | | | | | | |
| 385 | | | | Y | | | | | 3 | | | | | | | | | | | | | | 4 | | | | | | | | | | | | |
| 2 | | | | | | | | | 392 | | | | T | | | | | | | | | | 4 | | | | | | | | | | | | |
| 386 | A | | | | A | | | | 393 | | | T | V | E | D | | | | | | | | 47 | | | | | L | | | | | | | V |
| 387 | S | | | | D | | | | 394 | | | | V | E | D | | | | | | | | 408 | | | | | | | | | | | | V |
| 388 | S | | N | | A | K | F | | 395 | | | T | V | E | | | | | A | | N | | 409 | | | | | | | | | | | | A |
| 389 | | | | | Y | | | | 396 | | | | T | | | | | | | | | | 4 | | | | | | | | | | | | |
| 390 | S | | N | | A | | | | 397 | | | T | V | E | D | | | A | | | | | 408 | | | | | | | | | | | | V |
| 390 | S | | N | | A | | | | 398 | | | T | V | E | | | | A | | | | | 409 | | | | | | | | | | | | A |
| 2 | | | | | | | | | 399 | | | V | | | | | S | | | | | | 410 | E | | | | | | | | | | | |
| 2 | | | | | | | | | 400 | | | | | | | | S | | | | | | 410 | E | | | | | | | | | | | |
| 391 | | S | | | | | | | 400 | | | | | | | | S | | | | | | 410 | E | | | | | | | | | | | |

Figure 22-4

| SEQ ID NO: | 26 | 27 | 28 | 29 | 30 | 31 | 32 | 33 | SEQ ID NO: | 51 | 52 | 53 | 54 | 55 | 56 | 57 | 58 | 59 | 60 | 61 | 62 | 63 | SEQ ID NO: | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|
| 2 | P | G | K | A | T | E | V | R | 3 | T | Y | M | M | G | N | E | L | T | F | L | D | D | 4 | K | V | E | L | M | Y | P | P | P | Y | Y | L |
| 2 | | | | | | | | | 414 | | | | | | | | S | | | P | | | 423 | E | | | | | | | | | | | |
| 411 | | | N | | | | | | 415 | | | | | | | | S | | | | | | 423 | E | | | | | | | | | | | |
| 2 | | | | | | | | | 416 | | | | | | D | | | | | | | | 4 | | | | | | | | | | | | |
| 412 | | | | | N | | | | 417 | | | | | E | | | | | | | | | 4 | | | | | | | | | | | | |
| 412 | | | | | N | | | | 418 | | | | K | E | | | | | | | | | 4 | | | | | | | | | | | | |
| 412 | | | | | N | | | | 419 | | | | K | E | D | | | | | | | | 4 | | | | | | | | | | | | |
| 412 | | | | | N | | | | 420 | | | | V | E | D | | | | | | | | 4 | | | | | | | | | | | | |
| 412 | | | | | N | | | | 421 | | | | K | | D | | | | | | | | 4 | | | | | | | | | | | | |
| 412 | | | | | N | | | | 421 | | | | K | | D | | | | | | | | 424 | | | | | | | | | | | | E |
| 412 | | | | | N | | | | 422 | | | | K | | | | | | | | | | 4 | | | | | | | | | | | | |
| 412 | | | | | N | | | | 422 | | | | K | | | | | | | | | | 424 | | | | | | | | | | | | E |
| 413 | | | | | N | | I | | 422 | | | | K | | | | | | | | | | 4 | | | | | | | | | | | | |
| 413 | | | | | N | | I | | 422 | | | | K | | | | | | | | | | 424 | | | | | | | | | | | | E |
| 413 | | | | | N | | I | | 419 | | | | K | E | D | | | | | | | | 4 | | | | | | | | | | | | |
| 413 | | | | | N | | I | | 418 | | | | K | E | | | | | | | | | 4 | | | | | | | | | | | | |
| 413 | | | | | N | | I | | 421 | | | | K | | D | | | | | | | | 4 | | | | | | | | | | | | |

Figure 22-5

| SEQ ID NO: | 26 | 27 | 28 | 29 | 30 | 31 | 32 | 33 | SEQ ID NO: | 51 | 52 | 53 | 54 | 55 | 56 | 57 | 58 | 59 | 60 | 61 | 62 | 63 | SEQ ID NO: | 93 | 94 | 95 | 96 | 97 | 98 | 99 | 100 | 101 | 102 | 103 | 104 |
|---|---|---|---|---|---|---|---|---|---|---|---|---|---|---|---|---|---|---|---|---|---|---|---|---|---|---|---|---|---|---|---|---|---|---|---|
| 2 | P | G | K | A | T | E | V | R | 3 | T | Y | M | M | G | N | E | L | T | F | L | D | D | 4 | K | V | E | L | M | Y | P | P | P | Y | Y | L |
| 425 | | | | | N | | I | | 437 | | | | K | | D | | | | | | | | 449 | | | | | | | | | | | | E |
| 425 | | | | | N | | I | | 438 | | | | | | D | | | | | | | | 4 | | | | | | | | | | | | |
| 426 | | | | | | | I | | 438 | | | | | | D | | | | | | | | 4 | | | | | | | | | | | | |
| 426 | | | | | | | I | | 437 | | | | K | | D | | | | | | | | 4 | | | | | | | | | | | | |
| 427 | | H | | | | | I | | 439 | | | | | E | D | | | | | | | | 4 | | | | | | | | | | | | |
| 427 | | H | | | | | I | | 437 | | | | K | | D | | | | | | | | 4 | | | | | | | | | | | | |
| 428 | | | | | D | | I | | 440 | | | | E | | D | | | | | | | | 4 | | | | | | | | | | | | |
| 429 | | H | | | D | | I | | 439 | | | | | E | D | | | | | | | | 4 | | | | | | | | | | | | |
| 430 | | H | | | N | | I | | 437 | | | | K | | D | | | | | | | | 4 | | | | | | | | | | | | |
| 431 | | H | | | N | | | | 439 | | | | | E | D | | | | | | | | 4 | | | | | | | | | | | | |
| 431 | | H | | | N | | | | 441 | | | | V | E | D | | | | | | | | 4 | | | | | | | | | | | | |
| 432 | | H | N | | A | | I | | 442 | | | | K | E | D | | | | | | | | 4 | | | | | | | | | | | | |
| 433 | | H | N | | D | | I | | 443 | | | | E | E | D | | | | | | | | 4 | | | | | | | | | | | | |
| 433 | | H | N | | D | | I | | 444 | | | | V | E | D | | | | | | | K | 4 | | | | | | | | | | | | |
| 2 | | | | | | | | | 445 | | | | | | | | | | | K | | | 4 | | | | | | | | | | | | |
| 2 | | | | | | | | | 3 | | | | | | | | | | | | | | 450 | | | F | | | | | | | | | |
| 2 | | | | | | | | | 3 | | | | | | | | | | | | | | 449 | | | | | | | | | | | | E |
| 434 | | | | I | | | | | 3 | | | | | | | | | | | | | | 4 | | | | | | | | | | | | |
| 435 | | | | | | | | F | 3 | | | | | | | | | | | | | | 4 | | | | | | | | | | | | |
| 2 | | | | | | | | | 446 | C | | | | | | | | | | | | | 4 | | | | | | | | | | | | |
| 2 | | | | | | | | | 447 | K | | | | | | | | | | | | | 4 | | | | | | | | | | | | |
| 2 | | | | | | | | | 3 | | | | | | | | | | | | | | 451 | | | M | | | | | | | | | |
| 436 | | | | Y | | | | | 448 | | | | | | | | | | | Y | | | 449 | | | | | | | | | | | | E |

Figure 22-6

CTLA4 PROTEINS AND THEIR USES

1. CROSS REFERENCE TO RELATED APPLICATIONS

This application claims the benefit of U.S. Provisional Application No. 61/313,516, filed Mar. 12, 2010, the contents of which are incorporated by reference herein in their entireties.

1.1 Sequence Listing

The instant application contains a Sequence Listing which has been submitted in ASCII format via EFS-Web and is hereby incorporated by reference in its entirety. Said ASCII copy, created on Feb. 11, 2011, is named 237US161.txt and is 498,294 bytes in size.

2. FIELD OF THE INVENTION

The present invention relates to CTLA4 proteins, pharmaceutical compositions comprising CTLA4 proteins, and therapeutic uses of such proteins.

3. BACKGROUND

T-cell lymphocytes play a critical role in cell-mediated immunity by providing for an adaptive response to specific pathogens. T-cell activation depends on activation of at least two signaling pathways, one that is antigen specific and the other that is antigen nonspecific. A T-helper cell antigenic response requires activation of a first signaling pathway by the binding of the T-cell receptor to an antigen bound to MHC (major histocompatibility complex) on the surface of an antigen presenting cell (APC). The antigenic response also requires activation of a second signaling pathway, which produces a co-stimulatory signal, by the binding of CD28 protein on the surface of the T-cell to CD80 (B7-1) and CD86 (B7-2) on the surface of the APC. Because the antigen-specific signal is not sufficient to generate a full antigenic response, T-cell receptor/antigen-MHC binding without co-stimulation may lead to clonal inactivation or anergy. (See, e.g., Jenkins et al., 1993, Curr. Opin. Immunol. 5:361). The co-stimulatory pathway plays a role not only in T-cell activation and differentiation, but also in tissue migration and peripheral tolerance induction. (See Salomon et al., 2001, Ann. Rev. Immunol. 19:225.)

Activated T-cells also express on their cell surface cytotoxic T-lymphocyte-associated antigen 4 (CTLA4), a homologue of CD28 that binds CD80 and CD86 with higher affinity. CTLA4 expression results in competitive binding to CD80 and CD86, blocking the CD80/86-CD28 interaction and terminating T-cell activation. Because these signaling pathways determine the magnitude of a T-cell response to antigen, as well as downstream responses to antigen, agents that modulate one or more costimulatory signals, e.g., by blocking one or more of the interactions between CD80/CD86 and CD28 and/or CTLA4, may be effective in treating disorders that result from disregulated cell-mediated immune responses. (See, e.g., Mueller, et al., 1989, Annu Rev. Immunol. 7:445).

Suitable agents for the disruption of the CD80/86-CD28 interaction include antibodies and fusion proteins. For example, in an experimental autoimmune encephalomyelitis (EAE) model, T-cells were blocked using anti-CD80 and anti-CD86 antibodies. (See Racke, et al., 1995, J. Clin. Invest. 96:2195). In another example, anti-CD80 and anti-CD86 antibodies were used to block type 2 in vivo immune responses (i.e., immune responses mediated by IgG antibodies and directed against cell-surface or matrix antigens) and the production of IL-4. (Greenwald, et al., 1997, J. Immunol. 158:4088) CD28-Ig fusion proteins have been demonstrated to interact with CD80 and/or CD86 on dendritic cells and to activate them, which results in an adjuvant activity of soluble CD28 that produces enhanced T-cell mediated immune responses in vivo. (Orabona et al., 2004, Nature Immunol. 5(11):1134). Alternatively, CTLA4-Ig fusion proteins have been used to disrupt CD80/86-CD28 interactions. (See, e.g., McIntyre, et al., 2005, Drugs of the Future, 30:873).

Recent studies of T-cell activation and the costimulatory pathway indicate that CD80 and CD86 can play different roles in immune responses, and especially in autoimmunity. Thus, blocking the binding of only one of CD80 or CD86 to CD28 has been shown to produce disparate effects in vivo, depending on the disease being studied and the timing of administration (See Salomon, 2001, Annu Rev. Immunol. 19:225; Kuchroo, et al., 1995, Cell 80:707; Racke, et al., 1995, J. Clin. Invest. 96:2195; Lenschow et al., 1995, J. Exp. Med. 181:1145; and Greenwald, et al., J. Immunol., 1997, 158:4088).

Antibodies that bind to CTLA4 and disrupt CTLA4 inhibition of CD28-mediated T-cell responses are currently in development for the treatment of various cancers. Ipilimumab, a human anti-CTLA4 $IgG_1$ antibody, is in Phase III trials for melanoma and in Phase II trials for breast cancer and prostate cancer. Tremelimumab, a human anti-CTLA4 $IgG_2$ antibody, is in Phase II trials for prostate cancer, bladder cancer, and colorectal cancer.

Fusion proteins that bind to CD80 and/or CD86 and disrupt the interaction with CTLA4 and CD28 are good candidates for the development of immunomodulatory agents. Fusion proteins allow for the engineering of proteins with, for example, improved solubility, stability, deliverability, and/or activity. One such immunomodulatory agent is the soluble fusion protein abatacept (Orencia®), developed for the treatment of rheumatoid arthritis (RA) and juvenile idiopathic arthritis, autoimmune disorders which attack the joints, causing painful swelling that can eventually result in bone erosion and joint deformity.

Abatacept is a CTLA4-Ig fusion protein consisting of the extracellular domain of human CTLA4 and a modified Fc portion of human immunoglobulin $G_1$ ($IgG_1$) that includes hinge, CH2, and CH3 domains. The CTLA4 domain provides binding activity and the Fc portion is believed to provide stability, solubility and deliverability. Abatacept inhibits the interaction of CD28 on T-cells with CD80 and/or CD86 proteins on APC cells, thereby resulting in inhibition of T-cell activation. (See, e.g., Schwartz, 1992, Cell 71:1065). Accordingly, administration of abatacept results in a decrease in T-cell proliferation, activation and signaling, and attenuates the autoimmune response in rheumatoid arthritis. A second-generation soluble recombinant CTLA4-Ig fusion protein known as belatacept differs from abatacept in two amino acids and has a greater binding affinity for CD80 and CD86. Belatacept is in ongoing Phase III trials for use in kidney and other organ transplantation. (See Linsley et al., 2009, Immunol. Reviews 229:307-321). A third fusion protein, MAXY-4, a protein derived from abatacept but having increased binding to CTLA4 targets, is currently in preclinical development by Perseid Therapeutics, LLC and Astellas Pharma, Inc. for treatment of autoimmune diseases and transplant rejection.

Therapy with abatacept can be cost prohibitive. Higher affinity variants of abatacept could reduce the required effective therapeutic dose and therefore reduce the cost of therapy. Moreover, because less of the agent is required to achieve a beneficial result, the risk of developing an immunogenic response to the agent itself may also be decreased. Other side-effects may also be reduced. There is a need to provide improved fusion proteins with differential binding to the CD80 and CD86 proteins, for example, by generating variants with higher relative affinity for one isoform relative to the other. Such improved variants may provide targeted immune modulation for specific conditions or pathologies. Adverse effects or exacerbation of immune responses observed in some cases of CTLA4-Ig and anti-CTLA4 antibody therapies may also be reduced.

Citation or identification of any reference in Section 2 or in any other section of this application shall not be construed as an admission that such reference is available as prior art to the present disclosure.

4. SUMMARY

The present disclosure relates to proteins comprising a CTLA4 binding domain that are capable of binding CD80 and/or CD86 and that are related in sequence to SEQ ID NO: 1 (FIG. 1A). In certain aspects, the CTLA4 protein of the disclosure further comprises a fusion partner, such as an immunoglobulin domain, which is a non-CTLA4 protein.

CTLA4 has three CDR-like loops, referred to herein (in amino- to carboxy-terminal order) as CDR-like loop 1, CDR-like loop 2 and CDR-like loop 3. The CDR-like loops of CTLA4 is shown in FIG. 1B.

CTLA4 was subjected to comprehensive mutagenesis in its CDR-like loops to produce a population of variants with single point mutations. The variant population was then screened to identify point mutants that resulted in similar or increased binding affinity to CD80 or CD86 based on the variants' behavior in a population.

Variants were identified whose behavior in the population indicated a similar or higher binding affinity to CD80 or to CD86 relative to wild type CTLA4. Some of the variants were isolated from the population and their biological properties, such as binding to CD80 and CD86 (described in Example 1), inhibition of IL-2 secretion by Jurkat cells (described in Example 1) and inhibition of T-cell proliferation (described in Example 2), were further characterized. The amino acid substitutions in these variants are listed in FIGS. 8, 9, 11, 13, 15, 16 and 18. Other variants were not isolated from the population and their binding characteristics are based on their behavior in the population. The amino acid substitutions in these variants, which are referred to as "candidate" mutations, are listed in FIGS. 10, 12, 14, 17, 19, 20.

Accordingly, the present disclosure provides CTLA4 proteins comprising CDR-like loops that have at least one amino acid substitution as compared to the CDR-like loops of SEQ ID NO: 1. Exemplary substitutions in the CDR-like loops are found in FIGS. 8, 9, 10, 11, 12, 13, 14, 15, 16, 17, 18, 19 and 20. Preferred amino acid substitutions that can be incorporated into the CTLA4 proteins of the disclosure (singly or in combination) include, but are not limited to, the amino acid substitutions K28H and A29H in CDR-like loop 1.

In certain aspects, the present disclosure provides CTLA4 proteins that have at least one amino acid substitution in the CDR-like loops as compared to SEQ ID NO: 1 and that bind with high affinity to CD80 and CD86 as compared to a wild-type CTLA4 binding domain. Exemplary substitutions in the CDR-like loops that result in high affinity binding to CD80 and CD86 are found in FIG. 8 and in row 1 of FIG. 21.

In other aspects, the present disclosure provides CTLA4 proteins that have at least one amino acid substitution in the CDR-like loops as compared to the CDR-like loops of SEQ ID NO: 1 that bind with high affinity to CD80 and with neutral affinity (i.e., comparable to abatacept) to CD86 as compared to a wild-type CTLA4 binding domain. Exemplary substitutions in the CDR-like loops that result in high affinity binding to CD80 and with neutral affinity binding to CD86 are found in FIGS. 9, 10 and in rows 2-5 of FIG. 21.

In yet other embodiments, the present disclosure provides CTLA4 proteins that have at least one amino acid substitution in the CDR-like loops as compared to the CDR-like loops of SEQ ID NO: 1 that bind with high affinity to CD80 and with low affinity to CD86 as compared to a wild-type CTLA4 binding domain. Exemplary substitutions that result in high affinity binding to CD80 and low affinity binding to CD86 are found in FIGS. 11, 12 and in row 6 of FIG. 21.

In some embodiments, the present disclosure provides CTLA4 proteins that have at least one amino acid substitution in the CDR-like loops as compared to the CDR-like loops of SEQ ID NO: 1 that bind with neutral affinity to CD80 and with high affinity to CD86 as compared to a wild-type CTLA4 binding domain. Exemplary substitutions that result in neutral affinity binding to CD80 and high affinity binding to CD86 are found in FIGS. 13, 14 and rows 7-8 of FIG. 21.

In various embodiments, the present disclosure provides CTLA4 proteins that have at least one amino acid substitution in the CDR-like loops as compared to the CDR-like loops of SEQ ID NO: 1 and that bind with low affinity to CD80 and with high affinity to CD86 as compared to wild-type CTLA4 binding domain. Exemplary substitutions that result in low affinity binding to CD80 and high affinity binding to CD86 are found in FIG. 15 and in row 9 of FIG. 21.

In certain embodiments, the present disclosure provides CTLA4 proteins that have at least one amino acid substitution in the CDR-like loops as compared to the CDR-like loops of SEQ ID NO: 1 that bind with neutral affinity to CD80 and CD86 as compared to a wild-type CTLA4 binding domain. Exemplary substitutions that result in neutral affinity binding to CD80 and CD86 are found in FIGS. 16, 17 and rows 10-22 of FIG. 21.

In various embodiments, the present disclosure provides CTLA4 proteins that have at least one amino acid substitution in the CDR-like loops as compared to the CDR-like loops of SEQ ID NO: 1 that bind with neutral affinity to CD80 and with low affinity to CD86 as compared to a wild-type CTLA4 binding domain. Exemplary substitutions that bind with neutral affinity to CD80 and with low affinity to CD86 are found in FIGS. 18, 19 and rows 23-26 of FIG. 21.

In some embodiments, the present disclosure provides CTLA4 proteins that have at least one amino acid substitution in the CDR-like loops as compared to the CDR-like loops of SEQ ID NO: 1 that bind with low affinity to CD80 and with neutral affinity to CD86 as compared to a wild-type CTLA4 binding domain. Exemplary substitutions that bind with low affinity to CD80 and with neutral affinity to CD86 are found in FIG. 20 and in rows 27-34 of FIG. 21.

In certain embodiments, the present disclosure provides a variant CTLA4 polypeptide comprising an amino acid sequence having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from K28H, K28T, A29H, T51Y, M53F, M53Y, L58G, L61H, L61Y, K93M and K93Q.

In other embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from L58A, L58N, L58Q, L61A, K93V, L104H and L104Y.

In still other embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from T30E, M54R, G55P, E57P, L58E, L58P, L58Y, L61F and L104I.

In various embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide includes the amino acid substitution K93I as compared to SEQ ID NO: 1.

In other embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from L58H, L58K and D62H.

In some embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide includes at least one amino acid substitution selected from M54W and M54Y as compared to SEQ ID NO: 1.

In other embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from R33D and L61W.

In still other embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from A29K, T51N, M53W, L96K and L96R.

In various embodiments, the present disclosure provies a variant CTLA4 polypeptide comprising an amino acid sequence having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from G27A, Y52F, N56T and L104M.

In certain embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from P26I, P26L, P26M, P26Q, P26T, P26V, K28R, A29P, A29S, T30H, T30M, T305, V32E, R33P, T51A, Y52H, Y52M, Y52W, M53D, M54D, M54G, M54H, M54L, G55D, G55H, G55T, N56A, N56F, N56G, N56H, N56I, N56K, N56L, N56M, N56Q, N56R, N56S, N56V, N56Y, E57A, E57D, E57H, E57K, E57M, E57N, E57Q, E57R, E575, E57T, E57V, L58I, L58R, L58T, T59I, T59M, T59N, T59Q, T59R, T59S, T59V, L61E, L61I, L61M, L61T, L61V, D62R, D63E, D63G, D63H, D63T, K93G, V94G, V94I, E95W, P99H, P99T, P99L and Y102T.

In various embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide includes the amino acid substitution K28Y as compared to SEQ ID NO: 1.

In certain embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from P26N, G27I, G27Q, G27W, K28E, K28I, K28M, K28P, K28Q, K28V, T301, T30L, M53E, M53L, M53N, M54A, M54Q, M54S, L58D, L58V, T59H, T59K, T59L, T59P, L61D, L61G, L61Q, L61R, D62A, D62E, D62S, D63Q, D63S and K93R.

In some embodiments, the present disclosure provides a variant CTLA4 polypeptide having at least 90%, at least 95%, at least 97%, at least 98% or at least 99% sequence identity to amino acids 21 to 112 of SEQ ID NO: 1, wherein the variant polypeptide has at least one amino acid substitution as compared to SEQ ID NO: 1 selected from P26R, G27D, G27P, A29N, T30K, E31D, E31G, E31P, E31R, E31T, V32G, V32H, V32T, R33E, R33G, R33I, R33M, R33N, R33Q, R33W, R33Y, T51E, T51G, T51I, T51V, Y52A, Y52D, Y52I, Y52K, Y52L, Y52Q, Y52R, Y52S, Y52T, M53H, M53P, M53S, G55A, G55I, G55L, G55N, G55Q, G55R, G55Y, E57G, E57I, E57W, E57Y, T59D, T59G, T59Y, F60D, F60G, F60H, F60L, D62G, D62I, D62W, D63A, D63Y, K93D, K93H, K93N, K93P, K93W, V94A, V94D, V94H, V94N, V94P, V94R, V94T, V94W, E95G, E95I, E95K, E95P, E95Q, E95R, E95S, E95T, E95V, E95Y, L96A, L96G, L96H, L96M, L96P, L96Q, M97D, M97G, M97I, M97N, M97S, M97V, P99I, P99M, P99W, P99Y, P100H, P100L, P100T, P100V, P100W, P101L, Y102H, Y103H, Y103L, Y103P, Y103T, and L104P.

The variant CTLA4 proteins of the disclosure can comprise one or more additional mutations or combinations of mutations selected from one or more of FIG. 8, 9, 10, 11, 12, 13, 14, 15, 16, 17, 18, 19, 20, 21, and 22-1 to 22-6.

In certain aspects, the mutations in the CDR-like loops of the variant CTLA4 polypeptides of the disclosure as compared to abatacept (SEQ ID NO: 6) do not comprise (a) A29K; (b) M53E; (c) L61Y; (d) L104M; (e) R33P; (f) T59I; (g) L61F. In other aspects, the mutations in the CDR-like loops of the variant CTLA4 polypeptides of the disclosure as compared to abatacept (SEQ ID NO: 6) do not consist of (a) A29K; (b) M53E; (c) L61Y; (d) L104M; (e) R33P; (f) T59I; (g) L61F; (h) a combination of two or more of A29K, M53E, L61Y, L104M, R33P, T59I and L61F; or (i) a combination of three or more of A29K, M53E, L61Y, L104M, R33P, T59I and L61F. By way of example and not limitation, in specific embodiments, the mutations in the CDR-like loops of the variant CTLA4 polypeptides of the disclosure as compared to abatacept (SEQ ID NO: 6) do not comprise or consist of (1) A29K and, optionally, one, two, or more substitutions independently selected from M53E, L61Y, L104M, R33P, T59I and L61F; (2) M53E and, optionally, one, two, or more substitutions independently selected from A29K, L61Y, L104M, R33P, T59I and L61F; (3) L61Y and, optionally, one, two or more substitutions independently selected from A29K, M53E, L104M, R33P, T59I and L61F; (4) L104M and, optionally, one, two, or more substitutions independently selected from A29K, M53E, L61Y, R33P, T59I and L61F; (5) R33P and, optionally, one, two, or more substitutions independently selected from A29K, M53E, L61Y, L104M, T59I and L61F; (6) T59I and, optionally, one, two, or more substitutions independently selected from A29K, M53E, L61Y, L104M, R33P, and L61F; or (7) L61F and, optionally, one, two, or more substitutions independently selected from A29K, M53E, L61Y, L104M, R33P, and T59I.

In certain aspects, the variant CTLA4 polypeptide is a fusion protein. In certain embodiments, the fusion partner is a immunoglobulin constant domain, such as an $IgG_1$.

In various aspects, the CTLA4 proteins of the disclosure have sequences having at least 75% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity or at least 99% sequence identity to the amino acid sequence of a wild-type CTLA4 binding domain (amino acids 21 to 112 of SEQ ID NO: 1) or to the wild-type CTLA4 extracellular domain (SEQ ID NO: 1).

In various aspects, the CTLA4 proteins of the disclosure have up to 2, up to 3, up to 4, up to 5, up to 6, up to 7, up to 8, up to 9, or up to 10 amino acid substitutions in the CDR-like loops as compared to the CDR-like loops of SEQ ID NO: 1.

Nucleic acids comprise nucleotide sequences encoding the CTLA4 proteins of the disclosure are provided herein, as are vectors comprising nucleic acids. Additionally, prokaryotic and eukaryotic host cells transformed with a vector comprising a nucleotide sequence encoding a CTLA4 protein are provided herein, as well as eukaryotic (such as mammalian) host cells engineered to express the nucleotide sequences. Methods of producing CTLA4 proteins by culturing host cells are also provided.

The CTLA4 proteins of the disclosure are useful in the treatment of cancers, autoimmune diseases and the rejection of cell, organ or tissue graft transplants. In certain aspects, the CTLA4 proteins are useful in treating an autoimmune disease selected from rheumatoid arthritis and juvenile idiopathic arthritis.

It should be noted that the indefinite articles “a” and “an” and the definite article “the” are used in the present application, as is common in patent applications, to mean one or more unless the context clearly dictates otherwise. Further, the term “or” is used in the present application, as is common in patent applications, to mean the disjunctive “or” or the conjunctive “and.”

All publications mentioned in this specification are herein incorporated by reference. Any discussion of documents, acts, materials, devices, articles or the like that has been included in this specification is solely for the purpose of providing a context for the present disclosure. It is not to be taken as an admission that any or all of these matters form part of the prior art base or were common general knowledge in the field relevant to the present disclosure as it existed anywhere before the priority date of this application.

The features and advantages of the disclosure will become further apparent from the following detailed description of embodiments thereof.

5. BRIEF DESCRIPTION OF THE FIGURES

FIGS. 1A-1C. FIG. 1A shows the amino acid sequence of the human CTLA4 extracellular domain (SEQ ID NO: 1). Amino acids in the CDR-like loops (underlined) were identified by visual inspection of reported CTLA4 co-crystal structures. (Schwartz et al., 2001, Nature 410:604; Stamper et al., 2001, Nature 410:608). FIG. 1B shows the sequences of the CDR-like loops of wild-type CTLA4 and the corresponding sequence identifiers. FIG. 1C shows an alignment of (i) full-length human CTLA4 extracellular domain and containing a transmembrane domain (Genbank Accession No. NM_005214; SEQ ID NO: 5), (ii) abatacept as set forth in U.S. Pat. No. 5,434,131 (SEQ ID NO: 6); and (iii) human Fcγ1 (SEQ ID NO: 7). The extracellular domain of wild-type CTLA4-Ig comprises amino acids 1-124 of hCTLA4, which corresponds to the CTLA4 extracellular domain. CTLA4 dimerizes through the cysteine residue at position 120. Abatacept has a glutamine residue at position 125, which is at the junction of the hCTLA4 extracellular domain and the human Fcγ1. The $CH_1$ region of hFcγ1 contains a valine at the equivalent position. The human Fcγ1 region with the $IgG_1m(a)$ allotype starts at position 126 and is italicized. Cysteine residues at positions 130, 136 and 139 that are present in the Fcγ1 and are involved in disulfide bridges have been mutated to serine in abatacept. Position 148 in the CH2 region of Fcγ1 is mutated from proline to serine in abatacept. (Davis et al., 2007, J. Rheumatol. 34(11):2204).

FIGS. 2A-2B show the binding of novel CTLA4-Ig variants to CD80 and CD86 as measured by competition AlphaLISA®. Relative binding activities of variants that showed improved binding to at least one of CD80 and CD86 are shown in FIG. 2A. Relative binding activities of variants that showed equivalent binding to at least one of CD80 and CD86 are shown in FIG. 2B. Open and solid bars indicate the binding data with CD80 and CD86, respectively. Data are normalized with an $IC_{50}$ value obtained from wild-type CTLA4-Ig, and are shown as the average fold improvement from two independent sets of experiments. Binding activity of abatacept that contains the mutation P148S mutation in the CH2 domain was confirmed to have negligible impact on ligand binding. Each data point of the dilution curve was duplicated in the assay plate. The average $IC_{50}$ value of wild-type CTLA4-Ig was determined to be 0.89 nM±0.26 and 4.26 nM±0.76 for CD80 and CD86, respectively. Error bars represent the range of values obtained from duplicate experiments.

FIG. 3 shows the binding activity of known CTLA4-Ig variants to CD80 and CD86 as measured by competition AlphaLISA®.

FIGS. 4A-4C show the ability of wild-type and CTLA4-Ig variants to inhibit IL-2 production of Jurkat T-cells upon stimulation. FIG. 4A shows IL-2 production from Jurkat T-cells upon stimulation with CHO-K1 cells expressing CD80 or CD86 in the presence of wild-type CTLA4-Ig or control antibody. FIG. 4B shows full inhibition curves with titrating amounts of commercial abatacept or wild-type CTLA4-Ig or belatacept produced in-house. Relative potencies of selected CTLA-Ig variants of the disclosure in the inhibition of IL-2 production normalized with an $IC_{50}$ value obtained from wild-type CTLA4-Ig are shown in FIG. 4C. Error bars represent the range of values obtained from duplicate experiments.

FIGS. 5A-5E show the ability of wild-type and CTLA4-Ig variants to inhibit proliferation of primary allo-stimulated T-cells. Symbols represent means of triplicate determinations. Data are representative of at least three independent experiments.

FIGS. 6A-6D show the ability of wild-type and CTLA4-Ig variants to inhibit proliferation of secondary allo-stimulated T-cells. Symbols represent means of triplicate determinations. Data are representative of at least three independent experiments.

FIG. 7 shows the numbering of the amino acids in the CDR-like loops of wild-type CTLA4-Ig.

FIG. 8 shows mutations in the wild-type CTLA4 CDR-like loops that binding studies indicate increase affinity for CD8O and CD86.

FIG. 9 shows mutations in the wild-type CTLA4 CDR-like loops that binding studies indicate increase affinity for CD80, and do not substantially impact CD86 binding.

FIG. 10 shows candidate mutations that can be incorporated in the wild-type CTLA4 CDR-like loops for increasing affinity toward CD80 while not substantially impacting CD86 binding.

FIG. 11 shows mutations in the wild-type CTLA4 CDR-like loops that binding studies indicate increase affinity for CD80 and decrease affinity for CD86.

FIG. 12 shows candidate mutations that can be incorporated in the wild-type CTLA4 CDR-like loops for increasing affinity toward CD80 and decreasing affinity toward CD86.

FIG. 13 shows mutations in the wild-type CTLA4 CDR-like loops that binding studies indicate increase affinity for CD86 while not substantially impacting CD80 binding.

FIG. 14 shows candidate mutations that can be incorporated in the wild-type CTLA4 CDR-like loops for increasing affinity toward CD86 while not substantially impacting CD80 binding.

FIG. 15 shows mutations in the wild-type CTLA4 CDR-like loops that binding studies indicate decrease affinity for CD80 and increase affinity for CD86.

FIG. 16 shows mutations in the wild-type CTLA4 CDR-like loops that binding studies indicate do not substantially impact binding to CD80 or CD86.

FIG. 17 shows candidate mutations that can be incorporated in the wild-type CTLA4 CDR-like loops and that do not substantially impact binding to CD80 or CD86.

FIG. 18 shows mutations in the wild-type CTLA4 CDR-like loops that binding studies indicate decrease affinity for, CD86 while not substantially impacting binding to CD80.

FIG. 19 shows candidate mutations that can be incorporated in the wild-type CTLA4 CDR-like loops for decreasing affinity for CD86 while not substantially impacting CD80 binding.

FIG. 20 shows candidate mutations that can be incorporated in the wild-type CTLA4 CDR-like loops for decreasing affinity for CD80 while not substantially impacting CD86 binding.

Figure 2A:
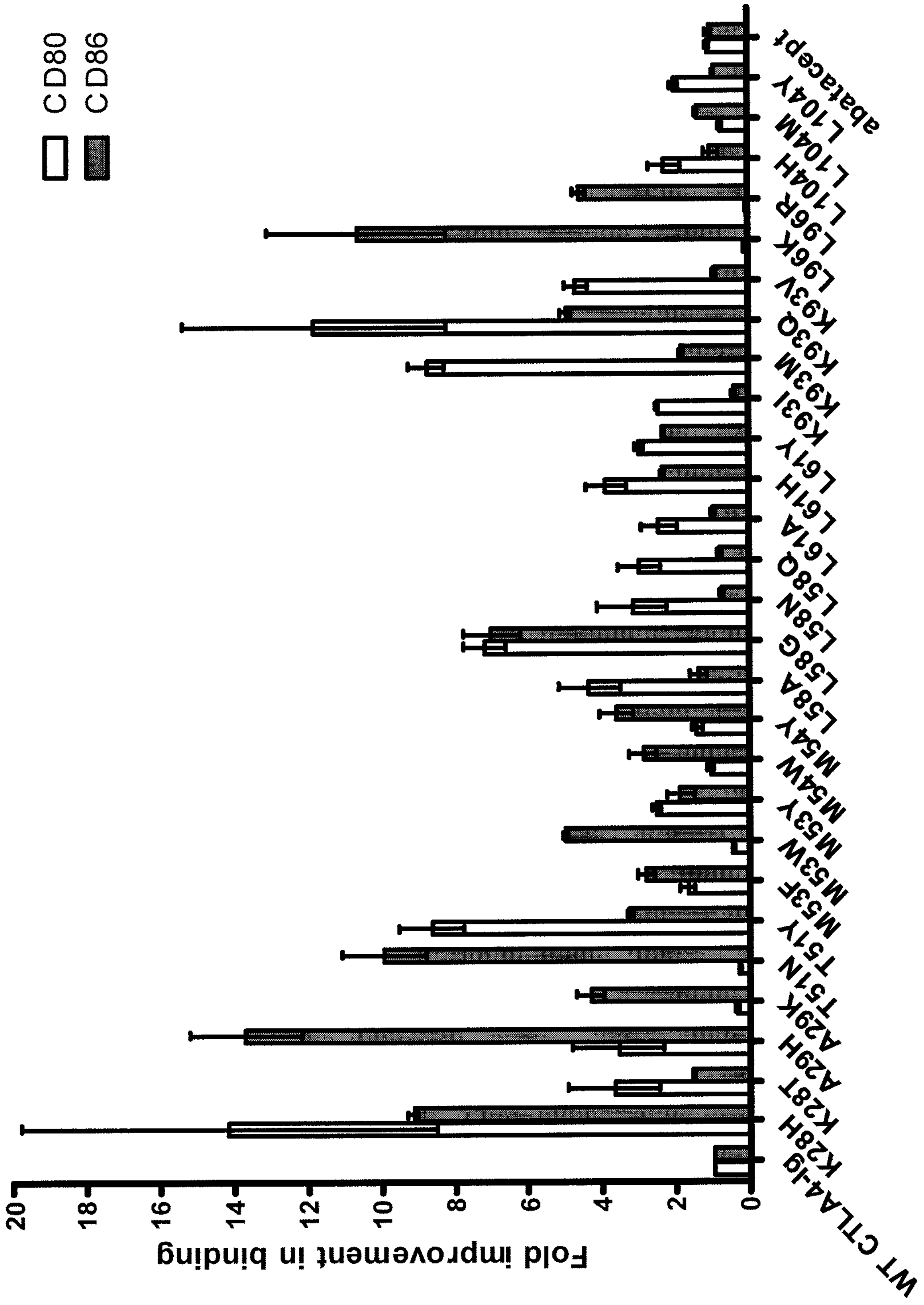
Figure 2B:
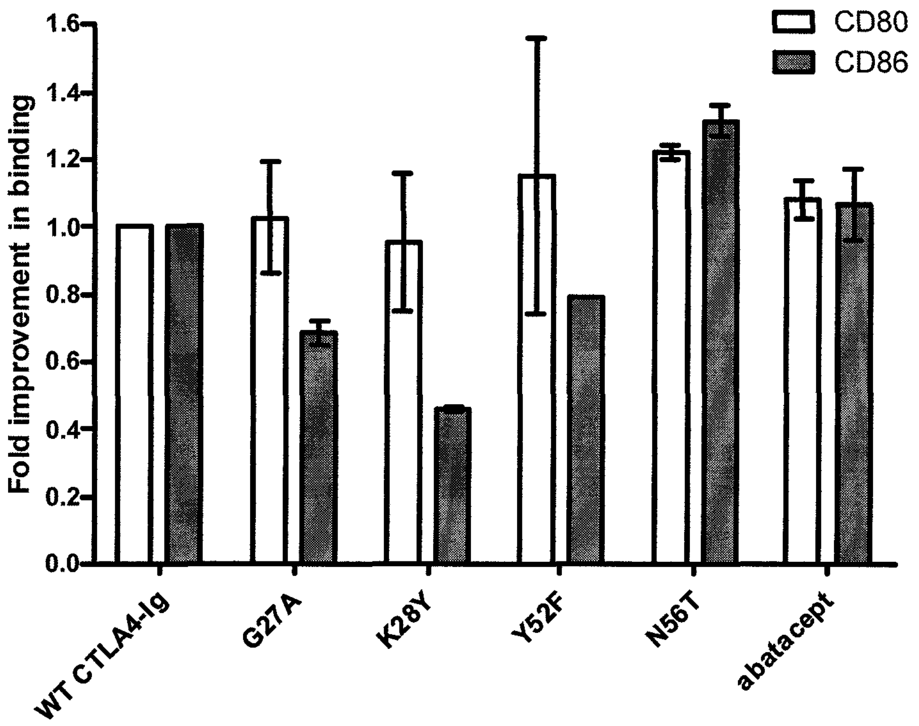

FIG. 21 shows known mutations in the wild-type CTLA4 CDR-like loops that can be incorporated into the CTLA4 proteins of the disclosure. Row 1 shows known mutations that can be incorporated in the wild-type CTLA4 CDR-like loops for increasing affinity for CD80 and CD86. Rows 2-5 show known mutations that can be incorporated in the wild-type CTLA4 CDR-like loops for increasing affinity for CD80 while not substantially impacting CD86 binding. Row 6 shows known mutations that can be incorporated in the wild-type CTLA4 CDR-like loops for increasing affinity for CD80 while decreasing affinity for CD86. Rows 7-8 show known mutations that can be incorporated in the wild-type CTLA4 CDR-like loops for increasing affinity for CD86 while not substantially impacting CD80 binding. Row 9 shows known mutations that can be incorporated in the wild-type CTLA4 CDR-like loops for increasing affinity for CD86 while decreasing affinity for CD80. Rows 10-22 show known mutations that can be incorporated in the wild-type CTLA4 CDR-like loops which do not substantially impact CD80 or CD86 binding. Rows 23-26 show known mutations that can be incorporated in the wild-type CTLA4 CDR-like loops for decreasing affinity for CD86 while not substantially impacting affinity for CD80. Rows 27-34 show known mutations that can be incorporated in the wild-type CTLA4 CDR-like loops for decreasing affinity for CD80 while not substantially impacting affinity for CD86.

FIGS. 22-1 to 22-6 show known mutations in the wild-type CTLA4 CDR-like loops that can be incorporated into the CTLA4 proteins of the disclosure.

6. DETAILED DESCRIPTION

The present disclosure provides novel polypeptides comprising variant CD80- and/or CD86-binding fragments of CTLA4 ("CTLA4 binding domain") that inhibit or suppress immune responses. The polypeptides of the disclosure comprise at least a CTLA4 binding domain that has one or more amino acid substitutions that maintain or alter the binding properties of CTLA4 to CD80 and/or CD86. Optionally, the variant CTLA4 binding domains are fused to a different (non-CTLA4) amino acid sequence, such as that of an immunoglobulin constant region. These novel polypeptides are collectively referred to herein as "CTLA4 proteins" or "CTLA4 polypeptides".

6.1. CTLA4 Extracellular Domain

The variant polypeptides of the disclosure comprise an amino acid sequence that is related in sequence to the CTLA4 extracellular domain (SEQ ID NO: 1). The CTLA4 extracellular domain is a single chain polypeptide that adopts an immunoglobulin variable fold with three CDR-like loops. The variant polypeptides of the disclosure contain at least one amino acid substitution in at least one CDR-like loop as compared to CTLA4 that maintain or alter the protein's binding properties to CD80 and/or CD86. In certain aspects, the variant CTLA4 polypeptides of the disclosure bind to CD80 and/or CD86 and block their interactions with their respective ligands, e.g., CTLA4 or CD28, thereby inhibiting one or more immune cell mediated responses. The variant CTLA4 polypeptides of the disclosure can also have amino acid mutations (e.g., deletions, insertions, additions or substitutions) in the non-CDR-like loop portions of the CTLA4 extracellular domain. Suitable mutations in the non-CDR-like regions of the CTLA4 extracellular domain include, but are not limited to, those disclosed, for example in U.S. Pat. Nos. 5,977,318; 6,107,056; 6,750,334; 7,034,121; 7,229,962; 7,432,344; 7,504,554; 7,385,045; 7,105,166; 6,090,914; 5,770,197; and U.S. Patent publication no. 2009/0258031, each of which is incorporated by reference herein in its entirety.

In certain embodiments, the variant CTLA4 polypeptides of the disclosure have an amino acid sequence that is at least 75% identical to the amino acid sequence of a CTLA4 binding domain (e.g., amino acids 21-112 of SEQ ID NO: 1). In other embodiments, the variant CTLA4 polypeptides of the disclosure have an amino acid sequence that is at least 75% identical to the amino acid sequence of the CTLA4 extracellular domain (e.g., amino acids 1-124 of SEQ ID NO: 1). In various embodiments, the variant CTLA4 polypeptides of the disclosure have an amino acid sequence that is at least 80% identical, at least 85% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence of a CTLA4 binding domain or to the amino acid sequence of a CTLA4 extracellular domain.

In some embodiments, the variant CTLA4 polypeptides of the disclosure comprise at least one mutation compared to a wild-type CTLA4 extracellular domain. In other embodiments, the variant CTLA4 polypeptides of the disclosure comprise at least one mutation compared to a wild-type CTLA4 binding domain. In other embodiments, the variant CTLA4 polypeptides of the disclosure comprise up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, or up to 20 amino acid substitutions as compared to a wild-type CTLA4 extracellular domain or as compared to a wild-type CTLA4 binding domain.

In certain embodiments, the CTLA4 extracellular domain includes amino acid residues 1-124 of the human CTLA4 protein (SEQ ID NO: 1). In various embodiments, the CTLA4 polypeptide of the disclosure is a CD80- and/or CD86-binding fragment of the CTLA4 extracellular domain comprising CDR-like sequences that are related to the CDR-like sequences of CTLA4. In certain embodiments, the binding fragment comprises a portion of the CTLA4 extracellular domain starting anywhere between amino acids 1 to 12 of SEQ ID NO: 1 and ending anywhere between amino acids 112 to 124 of SEQ ID NO: 1. In certain embodiments, the binding fragment is from amino acid 12 to amino acid 112 of SEQ ID NO: 1, from amino acid 10 to amino acid 112 of SEQ ID NO: 1, from amino acid 8 to amino acid 112 of SEQ ID NO: 1, from amino acid 6 to amino acid 112 of SEQ ID NO: 1, from amino acid 4 to amino acid 112 of SEQ ID NO: 1, from amino acid 1 to amino acid 112, amino acid 113, amino acid 114, amino acid 115, amino acid 116, amino acid 117, amino acid 118, amino acid 119, amino acid 120, amino acid 121, amino acid 122 or amino acid 123 of SEQ ID NO: 1. In yet other embodiments, the binding portion is from amino acid 12 to amino acid 114 of SEQ ID NO: 1, from amino acid 12 to amino acid 116 of SEQ ID NO: 1, from amino acid 12 to amino acid 118 of SEQ ID NO: 1, from amino acid 12 to amino acid 120 of SEQ ID NO: 1, from amino acid 12 to amino acid 122 of SEQ ID NO: 1, or from amino acid 12, amino acid 11, amino acid 10, amino acid 9, amino acid 8, amino acid 7, amino acid 6, amino acid 5, amino acid 4, amino acid 3 or amino acid 2 to amino acid 124 of SEQ ID NO: 1.

In certain embodiments, the CDR-like loops of CTLA4 are grafted onto a non-CTLA4 protein scaffold. The non-CTLA4 protein scaffold can be any protein scaffold known in the art that allows the CDR-like loops to maintain a three-dimensional structure that binds to CD80 and/or CD86. In certain embodiments, the non-CTLA4 protein scaffold is a variable domain of a camelid heavy chain antibody (VHH) or a variable domain of the shark new antigen receptor (VNAR) ("nanobodies"). In other embodiments, the scaffold can be from a protein other than an immunoglobulin. Such scaffolds for use in the CTLA4 variant proteins of the disclosure include, but are not limited to, fibronectin III (AdNectin), β-sandwich proteins (iMAB), lipocalins (Anticalin), EETI-II/AGRP (Microbody), BPTI/LACI-D1/ITI-D2 (Kunitz domain), thioredoxin (Peptide aptamer), protein A (Affibody), ankyrin repeat (DARPin), γB-crystallin/ubiquitin (Affilin), $CTLD_3$ (Tetranectin) and $(LDLR\text{-}A\ module)_3$ (Avimer).

In some embodiments, the variant CTLA4 polypeptide of the disclosure is a monomer. In other embodiments, the CTLA4 polypeptide is a dimer. In certain embodiments, the CTLA4 dimer is a covalent dimer, e.g., a disulfide-linked dimer. In other embodiments, the CTLA4 dimer is a non-covalent dimer. In still other embodiments, the CTLA4 polypeptide is a multimer, e.g., a tetramer.

The variant CTLA4 polypeptides of the present disclosure have a binding affinity for a CTLA4 ligand. In certain embodiments the CTLA4 polypeptides have a binding affinity for the extracellular domain of human CD80, or a portion thereof. In various embodiments, the CTLA4 polypeptides have a binding affinity for the extracellular domain of human CD86, or a portion thereof.

In some embodiments, the variant CTLA4 polypeptides of the disclosure have a binding affinity for CD80 and/or CD86 that is increased compared to the binding affinity of the wild-type CTLA4 extracellular domain, e.g., in the context of abatacept. As used herein, a variant with "increased affinity" for CD80 and/or CD86 (a "high affinity" variant) refers to a polypeptide of the disclosure having a binding affinity that is at least 1.5×, at least 1.75×, at least 2×, at least 2.5×, at least 3×, at least 3.5×, at least 4×, at least 4.5×, at least 5×, at least 5.5×, at least 6×, at least 6.5×, at least 7×, at least 7.5×, at least 8×, at least 8.5×, at least 9×, at least 9.5×, at least 10×, or at least 20× or greater than the binding affinity of the CTLA4 extracellular domain for CD80 and/or CD86. In other embodiments, the variant CTLA4 polypeptides of the disclosure have a binding affinity for CD80 and/or CD86 that is about equal to the binding affinity of the wild-type CTLA4 extracellular domain, e.g., in the context of abatacept for CD80 and/or CD86 (a "neutral affinity" variant). As used herein, a "neutral affinity" variant has a binding affinity for CD80 and/or CD86 that is between about 0.5× and about 1.5× of the binding affinity of the CTLA4 extracellular domain for the ligand, such as about 0.6×, about 0.7×, about 0.8×, about 0.9×, about lx, about 1.1×, about 1.2×, about 1.3×, about 1.4× or about 1.5× of the binding affinity of the CTLA4 extracellular domain. In certain embodiments, a variant polypeptide of the disclosure has a decreased binding affinity for CD80 and/or CD86 as compared to the CTLA4 extracellular domain ("low affinity" variant). As used herein, a "low affinity" variant of the disclosure has a binding affinity that is less than 0.5×, less than 0.4×, less than 0.3×, less than 0.2×, less than 0.1×, less than 0.05×, less than 0.01× or less of the binding affinity of the CTLA4 extracellular domain.

In particular embodiments a variant CTLA4 protein of the disclosure is a high affinity variant with respect to both CD80 and CD86 binding. In some embodiments, the variant polypeptide is a high affinity variant with respect to CD80 and a neutral affinity variant with respect to CD86. In other embodiments, the variant CTLA4 polypeptide is a high affinity variant with respect to CD86 binding and neutral affinity variant with respect to CD80 binding. In still other embodiments, the variant CTLA4 protein of the disclosure is a high affinity variant with respect to CD80 binding and a low affinity variant with respect to CD86 binding. In yet other embodiments, the variant protein is a high affinity variant with respect to CD86 binding and a low affinity variant with respect to CD80 binding. In still other embodiments, the variant polypeptide of the disclosure is a neutral affinity variant with respect to both CD80 binding and CD86 binding. In various embodiments, the variant CTLA4 polypeptide of the disclosure is a low affinity variant with respect to CD86 binding and a neutral affinity variant with respect to CD80 binding. In yet other embodiments, the variant CTLA4 polypeptide of the disclosure is a neutral affinity variant with respect to CD86 binding and a low affinity variant with respect to CD80 binding.

In certain embodiments, the CTLA4 polypeptides of the disclosure comprise a variant CTLA4 binding domain in the context of full length CTLA4 (Genbank Accession No. AAL07473.1, which is incorporated herein by reference).

6.2. CTLA4 Fusion Partners

In certain aspects, the CTLA4 polypeptide of the disclosure can be a fusion protein in which the variant CTLA4 binding domain is operably linked to the amino acid sequence of another polypeptide, referred to herein as a "fusion partner." As used herein, the term "fusion partner" refers to a non-CTLA4 polypeptide that is covalently attached to the CTLA4 polypeptide variant, either directly or through a linker sequence. In various embodiments, the C-terminus of the CTLA4 binding domain is linked to the N-terminus of the fusion partner. In some embodiments, the fusion partner can comprise a transmembrane domain and/or a cytoplasmic domain. In these embodiments, the CTLA4 fusion protein is expressed on the surface of a cell. In particular embodiments, the fusion partner comprises a polypeptide that facilitates secretion, expression and/or solubility of the CTLA4 polypeptide.

In some embodiments, the CTLA4 fusion proteins of the disclosure are monomeric. In other embodiments, the CTLA4 fusion proteins of the disclosure are dimeric, either due to covalent linkage (e.g., by disulfide bonds) between the CTLA4 portions of two monomers and/or between the fusion partner polypeptides or due to non-covalent association of the CTLA4 and/or fusion partner portions of the monomers.

In some embodiments, the fusion partner is a protein or protein domain that dimerizes, such as lambda repressor, upstream binding factor, and leucine zipper domains (e.g., fos/jun). In particular embodiments, the fusion partner is an immunoglobulin (Ig) Fc polypeptide, i.e., the Fc domain of an Ig polypeptide, or a fragment thereof. In certain embodiments, the Fc polypeptide or fragment can be derived from various species, including, e.g., human, mouse, primate, etc., and can be derived from a different species than the CTLA4 binding domain to which it is linked. Thus, for example, in some embodiments, the CTLA4 binding domain is derived from a human protein and the fusion partner is derived from a mouse protein. In particular embodiments, the CTLA4 polypeptide and the fusion partner are both derived from human proteins.

In certain embodiments, the Ig Fc polypeptide comprises a first constant region ($CH_1$), a hinge region, a second constant region ($CH_2$) and a third constant region ($CH_3$) in the order (from the N-terminus to the C-terminus) $CH_1$-hinge-$CH_2$—$CH_3$. In some embodiments, the fusion partner optionally comprises a fourth constant region ($CH_4$). In some embodiments, the fusion partner is an immunoglobulin Fc fragment comprising the hinge region, $CH_2$ domain and $CH_3$ domain of the Ig polypeptide. In still other embodiments, the Ig Fc fragment comprises a single constant domain, such as the hinge region and a $CH_1$, $CH_2$ or $CH_3$ domain. In certain aspects, the Ig Fc does not have a hinge, e.g., an IgM. In some embodiments, the Ig Fc polypeptide comprises a wild-type Ig Fc polypeptide. Exemplary Fc polypeptides include, but are not limited to, $IgG_1$, $IgG_2$, $IgG_3$, $IgG_4$, IgA, IgE, IgD and IgM. In particular embodiments, the Fc polypeptide is an IgG.

Alternatively, the immunoglobulin Fc fusion partner is a modified Ig polypeptide. In certain embodiments, the Fc polypeptide has one or more amino acid substitutions compared to wild-type. For example, in certain embodiments, the Fc polypeptide is a mutant IgG in which one or more cysteine residues have been substituted with another amino acid (e.g., a serine residue) to eliminate one or more disulfide bonds formed between two Ig chains. In other embodiments, the Fc polypeptide is an IgG polypeptide in which one or more amino acid residues is substituted with another amino acid (e.g., proline) to reduce effector function (reduced Fc receptor binding). See U.S. Patent Publication no. 2009/0258031.

In some embodiments, the Fc fusion partner or a fragment thereof can be modified to alter at least one constant region-mediated biological effector function relative to the corresponding wild type sequence. For example, in some embodiments, the Fc polypeptide can be modified to reduce at least one constant region-mediated biological effector function relative to an unmodified Fc region, e.g., reduced binding to the Fc receptor (FcγR). FcγR binding can be reduced by mutating the immunoglobulin constant region segment at particular regions necessary for FcγR interactions (see e.g., Canfield and Morrison, 1991, J. Exp. Med. 173:1483-1491; and Lund et al., 1991, J. Immunol. 147:2657-2662). Reduction in FcγR binding ability of the Fc region can also reduce other effector functions which rely on FcγR interactions, such as opsonization, phagocytosis and antibody-dependent cellular cytotoxicity ("ADCC").

In other embodiments, the Fc polypeptide can be modified to acquire or improve at least one constant region-mediated biological effector function relative to an unmodified Fc region, e.g., to enhance FcγR interactions (see, e.g., US 2006/0134709). For example, the Fc region can be modified to bind FcγRIIA, FcγRIIB and/or FcγRIIIA with greater affinity than the corresponding wild type constant region.

Thus, Fc fusion proteins of the disclosure can have alterations in biological activity that result in increased or decreased opsonization, phagocytosis, or ADCC as compared to a fusion protein having the corresponding wild-type Fc region. Such alterations are known in the art. For example, the Fc polypeptides can be modified as antibodies are modified to reduce ADCC activity, e.g., as described in U.S. Pat. Nos. 5,834,597 and 7,083,784; and US Patent Publication Nos. 2006/0198840, and 2007/0122403. An exemplary ADCC lowering variant corresponds to "mutant 3" shown in FIG. 4 of U.S. Pat. No. 5,834,597, in which residue 236 is deleted and residues 234, 235 and 237 (using EU numbering) are substituted with alanines.

In some embodiments, the Fc polypeptides for use in CTLA4 proteins of the disclosure have low levels of or lack fucose. Antibodies lacking fucose in the Fc region have been correlated with enhanced ADCC activity, especially at low doses of antibody. See Shields et al., 2002, J. Biol. Chem. 277:26733-26740; Shinkawa et al., 2003, J. Biol. Chem. 278: 3466-73. Methods of preparing fucose-less proteins include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

In yet another aspect, the proteins of the disclosure or fragments thereof can include Fc regions that have been modified to increase or reduce their binding affinities to the fetal Fc receptor, FcRn, for example by mutating the immunoglobulin constant region segment at particular regions involved in FcRn interactions (see e.g., WO 2005/123780). In particular embodiments, the Ig Fc fusion partner of the IgG class is mutated such that at least one of amino acid residues 250, 314, and 428 of the heavy chain constant region is substituted alone, or in any combinations thereof, such as at positions 250 and 428, or at positions 250 and 314, or at positions 314 and 428, or at positions 250, 314, and 428, with positions 250 and 428 a specific combination. For position 250, the substituting amino acid residue can be any amino acid residue other than threonine, including, but not limited to, alanine, cysteine, aspartic acid, glutamic acid, phenylalanine, glycine, histidine, isoleucine, lysine, leucine, methionine, asparagine, proline, glutamine, arginine, serine, valine, tryptophan, or tyrosine. For position 314, the substituting amino acid residue can be any amino acid residue other than leucine, including, but not limited to, alanine, cysteine, aspartic acid, glutamic acid, phenylalanine, glycine, histidine, isoleucine, lysine, methionine, asparagine, proline, glutamine, arginine, serine, threonine, valine, tryptophan, or tyrosine. For position 428, the substituting amino acid residues can be any amino acid residue other than methionine, including, but not limited to, alanine, cysteine, aspartic acid, glutamic acid, phenylalanine, glycine, histidine, isoleucine, lysine, leucine, asparagine, proline, glutamine, arginine, serine, threonine, valine, tryptophan, or tyrosine. Specific combinations of suitable amino acid substitutions are identified in Table 1 of U.S. Pat. No. 7,217,797, which table is incorporated by reference herein in its entirety. Such mutations increase binding of the Fc polypeptide to FcRn, which protects the protein from degradation and increases its half-life.

In certain embodiments, the Fc polypeptides for use in CTLA4 fusion proteins of the disclosure have an amino acid sequence that is at least 75% identical to the amino acid sequence of human Fcγ1 (SEQ ID NO: 7). In various embodiments, the Fc polypeptides have an amino acid sequence that is at least 80% identical, at least 85% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence of human Fcγ1 (SEQ ID NO: 7).

In some embodiments, the Fc polypeptides for use in CTLA4 fusion proteins of the disclosure comprise at least one mutation compared to human Fcγ1 (SEQ ID NO: 7). In other embodiments, the variant CTLA4 polypeptides of the disclosure comprise up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, or up to 20 or more amino acid substitutions as compared to wild-type human Fcγ1.

In some embodiments, the variant CTLA4 proteins of the disclosure are fusion proteins comprising a CTLA4 binding region comprising about 124 amino acids covalently linked (either directly or indirectly) at the C-terminus to an IgG Fc fusion partner comprising about 231 amino acids (the hinge, $CH_2$ and $CH_3$ regions of the Fc). In certain embodiments, the CTLA4 extracellular domain and the Ig Fc domain are linked via a linker, wherein the linker comprises from about 1 to about 10 amino acids. In particular embodiments, the linker comprises 1 amino acid.

In some embodiments, the variant fusion proteins of the disclosure comprise at least one amino acid substitution as compared to wild-type abatacept (SEQ ID NO: 5). In certain embodiments, the amino acid substitution is in the CTLA4 extracellular domain, e.g., in a CDR-like loop of CTLA4. In other embodiments, the variant fusion proteins of the disclosure comprise at least one amino acid substitution in the CTLA4 extracellular domain and at least one amino acid substitution in the Fc domain as compared to wild-type abatacept (SEQ ID NO: 5).

In certain embodiments, the CTLA4 fusion proteins of the disclosure have an amino acid sequence that is at least 75% identical to the amino acid sequence of wild-type abatacept (SEQ ID NO: 6). In various embodiments, the fusion proteins have an amino acid sequence that is at least 80% identical, at least 85% identical, at least 90% identical, at least 91% identical, at least 92% identical, at least 93% identical, at least 94% identical, at least 95% identical, at least 96% identical, at least 97% identical, at least 98% identical or at least 99% identical to the amino acid sequence of wild-type abatacept (SEQ ID NO: 6).

In some embodiments, the CTLA4 fusion proteins of the disclosure comprise at least one mutation compared to wild-type abatacept (SEQ ID NO: 6). In other embodiments, the variant CTLA4 polypeptides of the disclosure comprise up to 2, up to 3, up to 4, up to 5, up to 6, up to 7, up to 8, up to 9, up to 10, up to 11, up to 12, up to 13, up to 14, up to 15, up to 16, up to 17, up to 18, up to 19, or up to 20 or more amino acid substitutions as compared to wild-type abatacept.

In addition to the modifications described above, a CTLA4 protein of the disclosure can be modified in the CTLA4 portion and/or the fusion partner portion to include a signal sequence for secretion from the host cell or a peptide purification sequence, e.g., an epitope tag, a FLAG tag, a polyhistidine sequence, or a GST fusion. In certain embodiments, the CTLA4 proteins of the disclosure comprise one or more modified amino acids, e.g., a glycosylated amino acid, a PEGylated amino acid, a farnesylated amino acid, an acetylated amino acid, a biotinylated amino acid, an amino acid conjugated to a lipid moiety, and/or an amino acid conjugated to an organic derivatizing agent. In certain embodiments, the presence of modified amino acids is advantageous in, for example, (a) increasing polypeptide serum half-life and/or functional in vivo half-life, (b) reducing polypeptide antigenicity or immunogenicity, (c) increasing polypeptide storage stability, (d) increasing bioavailability, (e) decreasing effector function, and/or (f) decreasing or inhibiting undesired self-association (e.g., aggregate formation) between two or more CTLA4 proteins of the disclosure. Amino acid(s) can be modified, for example, co-translationally or post-translationally during recombinant production (e.g., N-linked glycosylation at N—X—S/T motifs during expression in mammalian cells) or modified by synthetic means.

In another aspect, a CTLA4 protein of the disclosure can be modified by the addition of protecting groups to the side chains of one or more the amino acids in the CTLA4 portion and/or in the fusion partner portion. Such protecting groups can facilitate transport of the polypeptides of the disclosure through membrane(s) or through certain tissue(s), for example, by reducing the hydrophilicity and increasing the lipophilicity of the polypeptides. Examples of suitable protecting groups include ester protecting groups, amine protecting groups, acyl protecting groups, and carboxylic acid protecting groups, which are known in the art (see, e.g., U.S. Pat. No. 6,121,236). Other modifications of the CTLA4 proteins of the disclosure, for example, by addition of polyethylene glycol or a detectable label, are discussed in Sections 5.6 and 5.7 below.

6.3. Increased Stability of CTLA4 Polypeptides

In certain aspects, the present disclosure provides CTLA4 polypeptides having increased protein stability as compared to wild-type CTLA4 Ig. The present disclosure provides CTLA4 polypeptides having single or multiple amino acid substitutions in their CDR-like loop regions as compared to the CDR-like loops of wild type CTLA4 extracellular domain and/or in the regions of the CTLA4 extracellular domain that are outside the CDR-like loops and/or in the fusion partner polypeptide, if present, wherein at least one substitution results in increased stability of the CTLA4 polypeptide as compared to wild-type CTLA4 Ig. In certain embodiments, the increased stability is upon storage of the CTLA4 polypeptide. In other embodiments, the increased stability is due to resistance to degradation by proteases and the like. In various embodiments, the increased stability is due to increased conformational stability. In some embodiments, the increased stability is due to decreased aggregation.

In certain embodiments, the increased stability does not affect the binding affinity of the variant CTLA4 polypeptides of the disclosure to CD80 and/or CD86. In certain embodiments, the stability of a CTLA4 protein of the disclosure can be at least 0.1-fold, at least 0.2-fold, at least 0.3-fold, at least 0.4-fold, at least 0.5-fold, at least 0.6-fold, at least 0.7-fold, at least 0.8-fold, at least 0.9-fold, at least 1-fold, at least 2-fold, at least 3-fold, at least 4-fold, at least 5-fold, at least 6-fold, at least 7-fold, at least 8-fold, at least 9-fold, or at least 10-fold of the stability of wild-type CTLA4 Ig. In certain embodiments, the stability of a CTLA4 protein of the disclosure is increased relative to the stability of wild-type CTLA4 Ig in a range between any of the foregoing values, e.g., 0.1-fold to 2-fold, 5-fold to 10-fold, 0.9-fold to 6-fold, or the like. In certain aspects, the stability of a CTLA4 polypeptide of the disclosure in a sample is greater than the stability of wild-type CTLA4 Ig in a sample where the samples are substantially identical (e.g., are both in pharmaceutical compositions containing the same ingredients) and/or are processed or handled in substantially the same way (e.g., are stored under the same conditions of temperature and humidity for the same period of time).

In certain aspects, the increased stability of a CTLA4 polypeptide of the disclosure is an increase in shelf-life. An increased shelf life can result from a decrease in amino acid oxidation (for example because an amino acid residue susceptible to oxidation, such as methionine, cysteine or tryptophan, in a CDR-like loop or in a region outside the CDR-like loops of the CTLA4 extracellular domain has been substituted relative to wild-type CTLA4-Ig). An increased shelf life can also result from a decrease in amino acid cyclization (for example because an amino acid residue susceptible to cyclization, such as asparagines or glutamic acid) in a CDR-like loop or in a region outside the CDR-like loops of the CTLA4 extracellular domain has been substituted relative to wild-type CTLA4 Ig. An increased shelf life can also result from the elimination of an amino acid motif that is recognized by proteases that may be in protein purifications at residual levels. An increased shelf life can also result from the elimination of an amino acid motif that causes aggregation of the protein. An increased shelf life can also result from an increase in conformational stability. The increase in shelf life or conformational stability, or decrease in oxidation, cyclization, proteolysis or aggregation levels relative to wild-type CTLA4 Ig can be at least 0.1-fold, at least 0.2-fold, at least 0.3-fold, at least 0.4-fold, at least 0.5-fold, at least 0.6-fold, at least 0.7-fold, at least 0.8-fold, at least 0.9-fold, at least 1-fold, at least 2-fold, at least 3-fold, at least 4-fold, at least 5-fold, at least 6-fold, at least 7-fold, at least 8-fold, at least 9-fold, or at least 10-fold. In certain embodiments, increase in shelf life or conformational stability, or decrease in oxidation, cyclization, proteolysis or aggregation levels relative to wild-type CTLA4 Ig is in a range between any of the foregoing values, e.g., 0.1-fold to 2-fold, 5-fold to 10-fold, 0.9-fold to 6-fold, or the like.

The present disclosure further provides methods for screening CTLA4 polypeptides for increased stability relative to wild-type CTLA4 Ig. In specific embodiments, the methods comprise the steps of: (a) determining the amount of full-length CTLA4 polypeptide in a first sample; and (b) comparing the amount of full-length CTLA4 polypeptide in the first sample with an amount of full-length wild-type CTLA4 Ig in a second sample. Methods of assaying for protein stability are known in the art.

6.4. Reduced Immunogenicity of CTLA4 Polypeptides

In certain aspects, the present disclosure provides CTLA4 polypeptides having reduced immunogenicity as compared to belatacept or MAXY-4 (Maxygen). The present disclosure provides CTLA4 polypeptides having single or multiple amino acid substitutions in their CDR-like loop regions as compared to the CDR-like loops of belatacept or MAXY-4 extracellular domain and/or in the regions of the CTLA4 extracellular domain that are outside the CDR-like loops and/or in the fusion partner polypeptide, if present, wherein at least one substitution results in reduced immunogenicity of the CTLA4 polypeptide as compared to belatacept or MAXY-4. In certain embodiments, the reduced immunogenicity results from one or more amino acid substitutions that result in eliminating or mitigating one or more T cell epitopes.

In certain aspects, the CTLA4 proteins of the disclosure having reduced immunogenicity have comparable or altered biological activity as compared to belatacept or MAXY-4, e.g., affinity towards CD80 and/or CD86.

In certain embodiments, the immunogenicity of a CTLA4 polypeptide of the disclosure is reduced relative to belatacept or MAXY-4. Such polypeptides generally have variant sequences relative to the CTLA4 extracellular domain and/or the fusion partner, if present. In certain embodiments, the CTLA4 polypeptides will generally have 1, 2 or 3 amino acid substitutions in one or both of the CTLA4 extracellular domain sequence and the fusion partner sequence, if present. In other embodiments, the CTLA4 polypeptides can have 4, 5, 6, 7, 8, 9, or 10 amino acid substitutions in one or both of the CTLA4 extracellular domain sequence and the fusion partner sequence, if present. In still other embodiments, the CTLA4 polypeptides can have 11, 12, 13, 14, 15, 16, 17, 18, 19, or 20 amino acid substitutions in one or both of the CTLA4 extracellular domain sequence and the fusion partner sequence, if present.

As used in the present disclosure, a variant with "reduced immunogenicity" refers to a CTLA4 polypeptide comprising a variant sequence as compared to belatacept or MAXY-4 that elicits a reduced proliferative response in peripheral blood mononuclear cells as compared to belatacept or MAXY-4. An exemplary proliferation assay that can be used to evaluate the proliferative response is set forth in Section 5.6 below. The reduced proliferative response can be reflected in terms of the percentage of responders, the stimulation index, or both.

In other embodiments, a peptide having a variant sequence as compared to the corresponding peptide in belatacept or MAXY-4 results in at least 25% fewer responders, in at least 30% fewer responders, in at least 35% fewer responders, in at least 40% fewer responders, in at least 45% fewer responders, in at least 50% fewer responders, in at least 60% fewer responders, in at least 65% fewer responders, in at least 70% fewer responders, in at least 75% fewer responders, in at least 80% fewer responders, in at least 85% fewer responders, in at least 90% fewer responders, in at least 95% fewer responders, in at least 100% fewer responders, or a reduction in responders in a range between any of the foregoing values, e.g., 25%-75% fewer responders, 50%-90% fewer responders, 60%-100% fewer responders, 70%-90% fewer responders, or the like. In certain aspects, the ability of variant peptides of belatacept or MAXY-4 to elicit a T-cell response as compared respectively to the corresponding wild-type peptides of belatacept or MAXY-4 is determined by the assay set forth in Section 5.6, below.

In other embodiments, a peptide having a variant sequence as compared to the corresponding peptide in belatacept or MAXY-4 results in a stimulation index that is at least 5% less, at least 10% less, at least 15% less, at least 20% less, at least 25% less, at least 30% less, at least 35% less, or at least 40% less than the stimulation index elicited by the corresponding peptide in wild-type CTLA4 Ig, or results in a stimulation reduced by a range between any of the foregoing values as compared to wild-type CTLA4 Ig, e.g., 5%-20% less, 10%-30% less, 30%-40% less, or the like. In certain embodiments, the stimulation index is determined by the assay set forth in Section 5.6, below.

6.5. Nucleic Acids and Expression Systems

The present disclosure encompasses nucleic acid molecules encoding the CTLA4 polypeptides of the disclosure and host cells engineered to recombinantly express the polypeptides.

A CTLA4 protein of the disclosure can be prepared by recombinant expression of a nucleic acid encoding a CTLA4 binding portion or of a nucleic acid encoding a CTLA4 fusion protein in a host cell. To express a CTLA4 protein recombinantly, a host cell is transfected with one or more recombinant expression vectors carrying nucleic acids encoding the CTLA4 proteins such that the proteins are expressed in the host cell and, optionally, secreted into the medium in which the host cells are cultured, from which medium the proteins can be recovered. Standard recombinant DNA methodologies are used to obtain nucleic acids encoding CTLA4 proteins, incorporate these nucleic acids into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

The nucleic acids encoding the variant CTLA4 polypeptides of the disclosure can be synthesized in part or completely. Alternatively, nucleic acids encoding the CTLA4 binding portion are first obtained. These DNAs can be obtained from PCR of total cellular RNA of, for example, H38 (HTLV-II-associated leukemia) cell line. See U.S. Pat. No. 5,434,131. In addition, if the CTLA4 protein is a fusion protein, nucleic acids encoding the fusion partner, e.g., an immunoglobulin constant region, can be obtained by amplification and modification of germline DNA or cDNA encoding the desired fusion protein, for example using the polymerase chain reaction (PCR). A nucleic acid encoding wild-type abatacept can be synthesized and used as a template for mutagenesis to generate a variant as described herein using routine mutagenesis techniques; alternatively, a nucleic acid encoding the variant can be directly synthesized.

Once nucleic acids encoding the variant CTLA4 binding domains are obtained, the nucleic acid can be further manipulated by standard recombinant DNA techniques, for example to operatively link the CTLA4 binding domain-encoding DNA to another nucleic acid encoding another protein, e.g., a fusion partner, such as an antibody constant region and/or a flexible linker. The term "operatively linked," as used in this context, is intended to mean that the two nucleic acids are joined such that the amino acid sequences encoded by the two nucleic acids remain in-frame.

The isolated DNA encoding the CTLA4 binding domain can be converted to a nucleic acid encoding a fusion protein by operatively linking the CTLA4 binding domain-encoding DNA to another DNA molecule encoding one or more heavy chain constant regions ($CH_1$, $CH_2$, $CH_3$ and, optionally, $CH_4$). The sequences of human heavy chain constant region nucleic acids are known in the art (see e.g., Kabat, E. A., et al., 1991, Sequences of Proteins of Immunological Interest, Fifth Edition, U.S. Department of Health and Human Services, NIH Publication No. 91-3242) and nucleic acids encompassing these regions can be obtained by standard PCR amplification. The heavy chain constant region can be an $IgG_1$, $IgG_2$, $IgG_3$, $IgG_4$, IgA, IgE, IgM or IgD constant region, but in certain embodiments is an $IgG_1$ constant region.

To express the CTLA4 proteins of the disclosure, DNAs encoding partial or full-length proteins, obtained as described above, are inserted into expression vectors such that the nucleic acids are operatively linked to transcriptional and translational control sequences. In this context, the term "operatively linked" is intended to mean that a nucleic acid encoding a CTLA4 protein is ligated into a vector such that transcriptional and translational control sequences within the vector serve their intended function of regulating the transcription and translation of the CTLA4 protein-encoding nucleic acid. The expression vector and expression control sequences are chosen to be compatible with the expression host cell used.

The nucleic acids encoding CTLA4 proteins of the disclosure are inserted into the expression vector by standard methods (e.g., ligation of complementary restriction sites on the CTLA4 protein gene fragment and vector, or blunt end ligation if no restriction sites are present). If the CTLA4 protein is a fusion protein, prior to insertion of the CTLA4 binding domain-encoding sequences, the expression vector can already carry fusion partner sequences, e.g., antibody constant region sequences. For example, one approach to converting a protein of the disclosure comprising only a CTLA4 binding domain into a CTLA4 fusion protein is to insert the nucleic acid encoding the CTLA4 binding domain into expression vectors already encoding immunoglobulin Fc such that the CTLA4-encoding sequence is operatively linked to the Fc-encoding sequence within the vector. Additionally or alternatively, the recombinant expression vector can encode a signal peptide that facilitates secretion of the CTLA4 protein from a host cell. The nucleic acid encoding a CTLA4 protein can be cloned into the vector such that the signal peptide is linked in-frame to the amino terminus of the CTLA4 protein-encoding nucleic acid. The signal peptide can be a CTLA4 signal peptide or a heterologous signal peptide, e.g., an immunoglobulin signal peptide.

In addition to nucleic acids encoding CTLA4 proteins, the recombinant expression vectors of the disclosure carry regulatory sequences that control the expression of the CTLA4 protein-encoding nucleic acids in a host cell. The term "regulatory sequence" is intended to include promoters, enhancers and other expression control elements (e.g., polyadenylation signals) that control the transcription or translation of the nucleic acids encoding the CTLA4 proteins of the disclosure. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al., and U.S. Pat. No. 4,968,615 by Schaffner et al.

In addition to the CTLA4 protein-encoding nucleic acids and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR-host cells with methotrexate selection/amplification) and the neo gene (for G418 selection). For expression of the CTLA4 proteins, the expression vector(s) encoding the CTLA4 proteins is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection and the like.

It is possible to express the CTLA4 proteins of the disclosure in either prokaryotic or eukaryotic host cells. In certain embodiments, expression of CTLA4 proteins is performed in eukaryotic cells, e.g., mammalian host cells or yeast host cells, for optimal secretion of a properly folded, post-translationally modified and immunologically active protein. Exemplary mammalian host cells for expressing the recombinant proteins of the disclosure include Chinese Hamster Ovary (CHO cells) (including DHFR-CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NS0 myeloma cells, COS cells, 293 cells and SP2/0 cells. When recombinant expression vectors encoding CTLA4 proteins are introduced into mammalian host cells, the proteins are produced by culturing the host cells for a period of time sufficient to allow for expression of the protein in the host cells or secretion of the protein into the culture medium in which the host cells are grown. CTLA4 proteins can be recovered from the culture medium using standard protein purification methods.

Recombinant DNA technology can also be used to remove some or all of the DNA encoding the CTLA4 proteins that is not necessary for binding to a CTLA4 ligand. The molecules expressed from such truncated DNA molecules are also encompassed by the proteins of the disclosure.

Once a nucleic acid encoding one or more portions of wild-type abatacept or of a CTLA4 protein with CDR-like sequences related to the CDR-like sequences of abatacept is generated, further alterations or mutations can be introduced into the coding sequence, for example to generate nucleic acids encoding CTLA4 proteins with different CDR-like sequences, or proteins with reduced affinity to the Fc receptor.

The CTLA4 proteins of the disclosure can also be produced by chemical synthesis (e.g., by the methods described in Solid Phase Peptide Synthesis, 2nd ed., 1984 The Pierce Chemical Co., Rockford, Ill.). Variant proteins can also be generated using a cell-free platform (see, e.g., Chu et al., Biochemia No. 2, 2001 (Roche Molecular Biologicals)).

Once a CTLA4 protein of the disclosure has been produced by recombinant expression, it can be purified by any method known in the art for purification of proteins, for example, using antibodies reactive with the CTLA4 binding domain of a protein of the disclosure, or chromatography (e.g., ion exchange, affinity, such as affinity for CD80 and/or CD86, and sizing column chromatography), centrifugation, differential solubility, or by any other standard technique. Further, the CTLA4 proteins of the present disclosure can be fused to heterologous polypeptide sequences described herein or otherwise known in the art to facilitate purification.

Once isolated, a CTLA4 protein can, if desired, be further purified, e.g., by high performance liquid chromatography (See, e.g., Fisher, Laboratory Techniques In Biochemistry And Molecular Biology (Work and Burdon, eds., Elsevier, 1980)), or by gel filtration chromatography on a Superdex™ 75 column (Pharmacia Biotech AB, Uppsala, Sweden).

6.6. Biological Activities of CTLA4 Proteins

In various embodiments, the CTLA4 proteins of the disclosure have certain biological activities, such as competing with abatacept for binding to CD80 and/or CD86, or blocking T-cell response.

Accordingly, in certain embodiments, CTLA4 proteins of the disclosure compete with abatacept for binding to CD80 or CD86. The ability to compete for binding to CD80 or CD86 can be tested using a competition assay. In one example of a competition assay, the AlphaLISA® (Amplified Luminescent Proximity Homogeneous) or AlphaScreen® assay can be used as a non-wash alternative to ELISA. In the AlphaLISA® assay, the ligand, CD80 or CD86 fused with a tag (e.g., CX-HA) is bound to AlphaLISA® acceptor beads conjugated with an anti-tag antibody (e.g., goat anti-human Cλ) and biotinylated abatacept is bound to AlphaScreen® strepavidin-coated donor beads (PerkinElmer, Waltham, Mass.). In the absence of competing CTLA4 variants, abatacept interacts with CD80 or CD86 and produces a signal at 615 nm. Addition of unlabeled CTLA4 variant competes with the abatacept/CD80 or CD86 interaction, reducing fluorescence quantitatively to enable determination of relative binding affinities. Abatacept can be biotinylated with Sulfo-NHS-Biotin using standard methods and dialyzed in PBS. Conjugation of AlphaLISA® acceptor beads is performed by following the "AlphaLISA® Assay Development Guide" (PerkinElmer). The binding is performed in a 384-well AlphaPlate (PerkinElmer) in assay buffer (e.g., 1% BSA, 0.01% Tween20 in PBS (pH 7.1)). Each well contains 0.5 nM biotinylated abatacept, 1:4 serially diluted CTLA4 competitor starting from 40 nM, 0.078 μg/ml CD80, and 5 μg/ml goat anti-human CX-conjugated acceptor beads. The plate is incubated in the dark for 1 h at room temperature. Streptavidin donor beads are then added to each well at 5 μg/ml. The plate is incubated in the dark at room temperature for an additional 30 min, after which it is read on an EnVision reader (PerkinElmer). Data are fit using nonlinear regression with the software GRAPHPAD PRISM (GraphPad, San Diego).

For CD86 binding, 8 nM biotinylated abatacept, 1:4 serially diluted competitor starting from 100 nM, 0.1 μg/ml CD86 and 10 μg/ml goat anti-human CX-conjugated acceptor beads are first incubated and then 10 μg/ml streptavidin donor beads are added. Variations on this competition assay can also be used to test competition between CTLA4 proteins of the disclosure and abatacept. For example, in certain aspects, the CTLA4 protein is used as a reference and abatacept is used as a test molecule. Additionally, instead of soluble CD80 or CD86, membrane-bound ligand expressed on the surface of cells (e.g., mammalian cells such as CHO) in culture can be used. Other formats for competition assay are known in the art and can be employed.

In various embodiments, a CTLA4 protein of the disclosure reduces the binding of labeled abatacept by at least 10%, by at least 20%, by at least 30%, by at least 40%, by at least 50%, by at least 60%, by at least 70%, by at least 80%, by at least 90%, by at least 95%, by at least 99%, or by a percentage ranging between any of the foregoing values (e.g., a CTLA4 protein of the disclosure reduces the binding of labeled abatacept by 10% to 40%, 50% to 70%, by 40% to 60% or by 80% to 99%) when the CTLA4 protein is used at a concentration of 0.01 μg/ml, 0.025 μg/ml, 0.05 μg/ml, 0.075 μg/ml, 0.1 μg/ml, 0.25 μg/ml, 0.5 μg/ml, 0.75 μg/ml, 1 μg/ml, 2 μg/ml, 10 μg/ml, 50 μg/ml, 100 μg/ml or at a concentration ranging between any of the forgoing values (e.g., at a concentration ranging from 0.1 μg/ml to 2 μg/ml).

In certain aspects, the CTLA4 variants of the disclosure are tested for their ability to elicit a T-cell response. In particular, CTLA4 peptides are synthesized using a multi-pin format by Mimotopes (Adelaide, Australia). The CTLA4 polypeptide sequences can be synthesized, for example, as 15-mer peptides overlapping by 12 amino acids. Peptides are resuspended in DMSO (Sigma-Aldrich) at approximately 1-2 mg/ml. Stock peptides are kept frozen at −20° C. For isolation of peripheral blood mononuclear cells, community donor buffy coat products can be purchased from the Stanford Blood Center, Palo Alto, Calif. Buffy coat material is diluted 1:1 v:v with DPBS containing no calcium or magnesium. Diluted buffy coat material (25-35 mls) is underlayed in 50 ml conical centrifuge tubes (Sarsted or Costar) with 12.5 mls of FicollPaque-PLUS (GE Healthcare). The samples are centrifuged at 900 g for 30 minutes at room temperature. Peripheral blood mononuclear cells (PBMC) are collected from the interface. DPBS is added to bring the final volume to 50 mls and the cells are centrifuged at 350 g for 5 minutes. Pelleted cells are resuspended in DPBS and counted. For isolation of dendritic cells, T75 culture flasks (Costar) are seeded with 108 freshly isolated PBMC in a total volume of 30 mls AIM V media (Invitrogen). Excess PBMC are frozen at −80° C. in 90% fetal calf serum (FCS), 10% DMSO at 5×107 cells/ml. T75 flasks were incubated at 37° C. in 5% CO2 for 2 hours. Nonadherent cells are removed, and the adherent monolayer is washed with DPBS. To differentiate dendritic cells from monocytes, 30 mis of AIM V media containing 800 units/ml of GM-CSF (R and D Systems) and 500 units/ml IL-4 (R and D Systems) are added. Flasks are incubated for 5 days. On day 5 IL-1a (Endogen) and TNFα (Endogen) are added to 50 pg/ml and 0.2 ng/ml, respectively. Flasks are incubated for two more days. On day 7, dendritic cells are collected by the addition of 3 mis of 100 mM EDTA containing 0.5 to 1.0 mg Mitomycin C (Sigma-Aldrich) for a final concentration of 10 mM EDTA and 16.5 to 33 μg/ml Mitomycin C. Flasks are incubated an additional hour at 37° C. and 5% CO2. Dendritic cells are collected, and washed in AIM V media 2-3 times. For cell culture, on day 7, previously frozen autologous PBMC are thawed quickly in a 37° C. water bath. Cells are immediately diluted into DPBS or AIM V media and centrifuged at 350 g for 5 minutes. $CD4^+$ cells are enriched by negative selection using magnetic beads (Easy-Sep $CD4^+$ kit, Stem Cell Technologies). Autologous CD4+ T cells and dendritic cells are cocultured at $2\times10^5$ $CD4^+$ T-cells per $2\times10^4$ dendritic cells per well in 96 well round bottomed plates (Costar 9077). Peptides are added at approximately 5 μg/ml. Control wells contain the DMSO (Sigma) vehicle alone at 0.25% v:v. Positive control wells contain DMSO at 0.25% and tetanus toxoid (List Biologicals or CalBioChem) at 1 μg/ml. Cultures are incubated for 5 days. On day 5, 0.25 μCi per well of tritiated thymidine (Amersham or GE Healthcare) is added. Cultures are harvested on day 6 to filtermats using a Packard Filtermate Cell harvester. Scintillation counting is performed using a Wallac MicroBeta 1450 scintillation counter (Perkin Elmer). Average background CPM values are calculated by averaging individual results from 6 to 12 replicates. The CPM values of the four positive control wells are averaged. Replicate or triplicate wells for each peptide are averaged.

Stimulation index values for the positive control and the peptide wells are calculated by dividing the average experimental CPM values by the average control values. In order to be included in the dataset, a stimulation index of greater than 3.0 in the tetanus toxoid positive control wells is required. A response is noted for any peptide resulting in a stimulation index of 2.95 or greater. Peptides are tested using peripheral blood samples from a group of 100 donors. Responses to all peptides are compiled. For each peptide tested, the percentage of the donor set that responds with a stimulation index of 2.95 or greater is calculated. In addition, the average stimulation index for all donors is calculated. $CD4^+$ T-cell epitope peptides are identified by an analysis of the percent responses to the peptides within the set of 100 donors. The average percent response and standard deviation are calculated for all peptides tested describing the CTLA4 polypeptide. A response rate greater than or equal to the average background response plus three standard deviations is considered a potential $CD4^+$ T-cell epitope.

In other aspects, a CTLA4 polypeptide of the disclosure inhibits activity of CD80 and/or CD86 in a range of in vitro assays, such as cell proliferation, cytokine (e.g., IL-2) production and cell adhesion.

In some embodiments, the activity assayed is immunosuppressive activity of the CTLA4 polypeptides of the disclosure. In particular, human blood freshly collected from donors is diluted with an equal volume of PBS and fractionated to isolate PMBCs using a Histopaque (Sigma) Ficoll gradient as per the manufacturer's instructions. PMBCs are diluted in RPMI medium (Sigma) supplemented with 10% FBS (Hyclone) and 1×PSG (penicillin, streptomycin and glutamine) (Invitrogen) and added to 96-well culture plates (BD Biosciences) at a density of $1\times10^5$ cells/well. CTLA4 proteins to be tested are serially diluted in the same medium and added to wells in quadruplicate. Cell proliferation is initiated by addition of PPD antigen (purified protein derivative from *mycobacterium tuberculosis*, Mycos) to a final concentration of SW/ml. After incubation at 37° C. for 5 days, $^3$H thymidine (GE Healthcare) is added at 1 μCi/well and plates are incubated at 37° C. for an additional 18 hours. Cells are harvested with a cell harvester (FilterMate Omnifilter-96 Harvester, Perkin Elmer) using the manufacturer's recommended conditions and measured for $^3$H thymidine incorporation using a scintillation counter (Wallac Trilux). Cell proliferation data are analyzed with GraphPad Prism 5 software using a non-linear regression curve fit model (sigmoidal dose-response, variable slope) and the least-squares fit method. The $IC_{50}$ parameters for each variant and their associated 95% confidence intervals are determined.

In certain embodiments, the activity assayed is inhibition of proliferation of primary and secondary allo-stimulated T-cells. In particular, the activity can be measured by the proliferation of human peripheral blood $CD4^+$ T-cells, for example as described by Larsen et al., 2005, Am. J. Transplant. 5:443-453. In primary allo-response assays, human $CD4^+$ T-cells ($3-10\times10^4$/well) are isolated and incubated with irradiated human B lymphoblastoid cell lines expressing equivalent amounts of CD80 and CD86 (e.g., PM cells, $8.0\times10^3$/well), along with varying concentrations of wild-type CTLA4-Ig or CTLA4 proteins of the disclosure. Primary allogenic stimulation assays proceed for 6 days before addition of 0.5 μCi/well of [$^3$H]-thymidine for the final 7 h of culture. For secondary allogenic stimulation assays, viable cells from 7-day primary allo-stimulated T-cells are isolated by differential density centrifugation and rested for 24 h. T-cells are then restimulated (secondary stimulation) by adding PM cells in the same ratio as above in the presence of titrating amounts of wild-type CTLA4-Ig or CTLA4 proteins of the disclosure. T-cells are stimulated for 3 days, pulsed with [$^3$H]-thymidine for the final 7 h of culture and harvested as above. Alternatively, the proliferation of primary and secondary allo-stimulated T-cells can be assayed as described in Example 2 below.

In various embodiments, the activity of CTLA4 variants of the disclosure can be measured by inhibition of cytokine production. For example, in specific embodiments, the cytokine is IL-2 produced by Jurkat T cells (Cox et al., 1999, Protein Expr. Purif. 17(1):26-32). Jurkat cells ($1.0\times10^5$/well)

are stimulated with 10 μg/mL PHA-L and cells (e.g., CHO-K1, 2.5x$10^4$/well) expressing recombinant CD80 or CD86 in the presence of titrating amounts of wild-type CTLA4-Ig or CTLA4 proteins of the disclosure. After 24 hours of culture, IL-2 concentration in the culture supernatant is measured using, for example, an AlphaLISA® Human IL-2 kit (Perkin Elmer). Alternatively, IL-2 concentration can be measured by other methods known in the art (e.g., ELISA).

Alternatively, in another embodiment, the inhibition of cytokine production can be measured in the culture media of secondary allo-stimulated T-cells (Larsen et al., 2005, Am. J. Transplant. 5:443-453). Aliquots of culture supernatants from T-cells allo-stimulated for 3 days as described in secondary allo-stimulation assay above are removed prior to addition of [$^3$H]-thymidine. The level of cytokine production (e.g., IFNγ, IL-2, IL-4) is measured using bead-based assays such as Luminex® (Invitrogen) or other methods known in the art (e.g., ELISA).

In certain embodiments, the activity assayed is cell adhesion. In particular, cells (e.g., CHO cells) recombinantly expressing CD80 or CD86 on the cells surface are diluted in medium, e.g., 10% FBS in RPMI, and seeded in 96-well plates and grown to confluence. When confluent, cells are incubated with a CTLA4 protein of the disclosure or abatacept or are used as a negative control. Unbound protein is removed from the cells by washing with warm medium. Purified T-cells that are either unstimulated or are prestimulated with 1 μg/ml anti-CD3 monoclonal antibody (30 min at 37° C.). T-cells (1x$10^5$ cells/well in 100 μl medium) are seeded onto the CD80 or CD86 expressing cells and allowed to adhere for 30 min at 37° C. Nonadherent cells are removed by washing each well three times with warm medium and counted (e.g., by trypan blue exclusion) in triplicate. Cell adherence to the CHO cells is calculated as (the number of nonadherent cells/total number of input cells)x100%. Alternatively, T-cells can be incubated with a fluorescent dye such as calcein AM (Molecular Probes, Eugene Oreg.) according to the manufacturer's instructions before being seeded into the wells. After incubation with T-cells, removal of medium containing non-adherent T-cells and washing, plates are read by a fluorescence multi-well plate reader. Percent of T-cell adhesion is derived from the formula: (specific adhesion in the presence of test fusion protein−background adhesion)/(specific adhesion in the presence of abatacept−background adhesion).

6.7. Kinetic Properties of CTLA4-Ig Fusion Proteins

In certain embodiments, the CTLA4 proteins of the disclosure have high affinity for CD80 and CD86. As used herein, variant proteins with "high affinity" for CD80 and/or CD86 have at least a 1.5-fold improvement in binding affinity as compared to abatacept. In other embodiments, the CTLA4 proteins of the disclosure have high affinity for CD80 and neutral affinity for CD86. In various embodiments, the CTLA4 proteins of the disclosure have high affinity for CD80 and low affinity for CD86. In still other embodiments, the CTLA4 proteins of the disclosure have high affinity for CD86 and neutral affinity for CD80. As used herein, variant proteins with "neutral affinity" for CD80 and/or CD86 have at least 0.5-fold but less than 1.5-fold improvement in binding affinity as compared to abatacept. In various embodiments, the CTLA4 proteins of the disclosure have low affinity for CD80 and high affinity for CD86. In still other embodiments, the CTLA4 proteins of the disclosure have neutral affinity for both CD80 and CD86. In some embodiments, the CTLA4 proteins of the disclosure have neutral affinity for CD80 and low affinity for CD86. In other embodiments, the CTLA4 proteins of the disclosure have low affinity for CD80 and neutral affinity for CD86. As used herein, a variant with "low affinity" for CD80 and/or CD86 has less than 0.5-fold improvement in binding affinity as compared to abatacept.

In specific embodiments, the CTLA4 proteins of the present disclosure have specific association rate constants ($k_{on}$ or $k_a$ values), dissociation rate constants ($k_{off}$ or $k_d$ values), affinity constants ($K_A$ values), dissociation constants ($K_D$ values) and/or $IC_{50}$ values. In various embodiments, binding constants for the interaction of the CTLA4 proteins with either CD80 or CD86 extracellular domain can be determined using surface plasmon resonance according to the method disclosed in Karlsson et al., 1991, J. Immunol. Methods 145:229-240. In certain aspects, such values are selected from the following embodiments.

In specific embodiments, the CTLA4 proteins of the disclosure bind to CD80 with a $k_{on}$ of at least $10^2$ $M^{-1}$ $s^{-1}$, at least 5x$10^2$ $M^{-1}$ $s^{-1}$, at least $10^3$ $M^{-1}$ $s^{-1}$, at least 5x$10^3$$M^{-1}$ $s^{-1}$, at least $10^4$ $M^{-1}$ $s^{-1}$ at least 5x$10^4$ $M^{-1}$ $s^{-1}$ at least $10^5$ $M^{-1}$ $s^{-1}$, at least 5x$10^5$ $M^{-1}$ $s^{-1}$ least $10^6$ $M^{-1}$ $s^{-1}$, at least 5x$10^6$ $M^{-1}$ $s^{-1}$ at least $10^7$ $M^{-1}$ $s^{-1}$, at least 5x$10^7$ $M^{-1}$ $s^{-1}$, at least $10^8$ $M^{-1}$ $s^{-1}$, at least 5x$10^8$ $M^{-1}$ $s^{-1}$, at least $10^9$ $M^{-1}$ $s^{-1}$, at least 5x$10^9$ $M^{-1}$ $s^{-1}$ or with a $k_{on}$ of any range between any pair of the foregoing values (e.g., 5x$10^4$ $M^{-1}$ $s^{-1}$ to $10^6$ $M^{-1}$ $s^{-1}$ or $10^2$ $M^{-1}$ $s^{-1}$ to 5x$10^5$ $M^{-1}$ $s^{-1}$).

In certain embodiments, the CTLA4 proteins of the disclosure bind to CD86 with a $k_{on}$ of at least $10^2$ $M^{-1}$ $s^{-1}$, at least 5x$10^2$ $M^{-1}$ $s^{-1}$ at least $10^3$ $M^{-1}$ $s^{-1}$, at least 5x$10^3$ $M^{-1}$ $s^{-1}$, at least $10^4$ $M^{-1}$ $s^{-1}$ at least 5x$10^4$ $M^{-1}$ $s^{-1}$ at least $10^5$ $M^{-1}$ $s^{1}$, at least 5x$10^5$ $M^{-1}$ $s^{-1}$ at least $10^6$ $M^{-1}$ $s^{-1}$ at least 5x$10^6$ $M^{-1}$ $s^{-1}$ at least $10^7$ $M^{-1}$ $s^{-1}$, at least 5x$10^7$ $M^{-1}$ $s^{-1}$, at least $10^8$$M^{-1}$ $s^{-1}$, at least 5x$10^8$ $M^{-1}$ $s^{1}$, at least $10^9$$M^{-1}$ $s^{1}$, at least 5x$10^9$ $M^{-1}$ $s^{-1}$ or with a $k_{on}$ of any range between any pair of the foregoing values (e.g., 5x$10^4$ $M^{-1}$ $s^{-1}$ to $10^6$ $M^{-1}$ $s^{-1}$ or $10^3$ $M^{-1}$ $s^{-1}$ to 5x$10^5$ $M^{-1}$ $s^{-1}$).

In certain embodiments, the CTLA4 proteins of the disclosure bind to CD80 with a $k_{off}$ of 2 $s^{-1}$ ore less, 1.5 $s^{-1}$ or less, 1 $s^{-1}$ or less, 0.5 $s^{-1}$ or less, 0.1 $s^{-1}$ or less, 5x$10^{-2}$ $s^{-1}$ or less, $10^{-2}$ $s^{-1}$ or less, 5x$10^{-3}$ $s^{-1}$ or less, $10^{-3}$ $s^{-1}$ or less, 5x$10^{-4}$ $s^{-1}$ or less, $10^{-4}$ $s^{-1}$ or less, 5x$10^{-5}$ $s^{-1}$ or less, $10^{-5}$ $s^{-1}$ or less, 5x$10^{-6}$ $s^{-1}$ or less, $10^{-6}$ $s^{-1}$ or less, 5x$10^{-7}$ $s^{-1}$ or less, $10^{-7}$ $s^{-1}$ or less, 5x$10^{-8}$ $s^{-1}$ or less, $10^{-8}$ $s^{-1}$ or less, or with a $k_{off}$ rate of any range between any pair of the foregoing values (e.g., 1 $s^{-1}$ to 5x$10^{-3}$ $s^{-1}$, or 5x$10^{-5}$ $s^{-1}$ to $10^{-8}$ $s^{-1}$).

In some embodiments, the CTLA4 proteins of the disclosure bind to CD86 with a $k_{off}$ of 10 $s^{-1}$ or less, 5 $S^{-1}$ or less, 1 $s^{-1}$ or less, 0.5 $s^{-1}$ or less, 0.1 $s^{-1}$ or less, 5x$10^{-2}$ $s^{-1}$ or less, $10^{-2}$ $s^{-1}$ or less, 5x$10^{-3}$ $s^{-1}$ or less, $10^{-3}$ $s^{-1}$ or less, 5x$10^{-4}$ $s^{-1}$ or less, $10^{-4}$ $s^{-1}$ or less, 5x$10^{-5}$ $s^{-1}$ or less, $10^{-5}$ $S^{-1}$ or less, 5x$10^{-6}$ $s^{-1}$ or less, $10^{-6}$ $s^{-1}$ or less, 5x$10^{-7}$ $s^{-1}$ or less, $10^{-7}$ $s^{-1}$ or less, 5x$10^{-8}$ $s^{-1}$ or less, $10^{-8}$ $s^{-1}$ or less, or with a $k_{off}$ rate of any range between any pair of the foregoing values (e.g., 1 $s^{-1}$ to 5x$10^{-3}$ $s^{-1}$, or 5x$10^{-5}$ $s^{-1}$ to $10^{-8}$ $s^{-1}$).

In some embodiments, a CTLA4 protein of the disclosure binds to CD80 with a $K_A$ (kon/koff) of at least at least 5x$10^5$ $M^{-1}$, at least $10^5$ $M^{-1}$, at least 5x$10^6$ $M^{-1}$, at least $10^6$ $M^{-1}$, at least 5x$10^7$ $M^{-1}$, at least $10^7$ $M^{-1}$, at least $10^8$$M^{-1}$, at least 5x$10^8$ $M^{-1}$, at least $10^9$ $M^{-1}$, at least 5x$10^9$ $M^{-1}$, at least 5x$10^{10}$ $M^{-1}$, at least $10^{10}$ $M^{-1}$, at least 5x$10^{11}$ $M^{-1}$, at least $10^{11}$ $M^{-1}$, at least 5x$10^{12}$ $M^{-1}$, at least $10^{12}$ $M^{-1}$, at least 5x$10^{13}$ $M^{-1}$, at least $10^{13}$ $M^{-1}$ at least 5x$10^{14}$ $M^{-1}$, at least $10^{14}$ $M^{-1}$, at least 5x$10^{15}$ $M^{-1}$, at least $10^{15}$ $M^{-1}$, or with a $K_A$ of any range between any pair of the foregoing values (e.g., 5x$10^5$ $M^{-1}$ to 5x$10^{13}$ $M^{-1}$ or 5x$10^8$ $M^{-1}$ to 5x$10^{15}$ $M^{-1}$).

In some embodiments, a CTLA4 protein of the disclosure binds to CD86 with a $K_A$ (kon/koff) of at least 5x$10^4$ $M^{-1}$, at least $10^4$ $M^{-1}$, at least 5x$10^5$ $M^{-1}$, at least $10^5$ $M^{-1}$, at least 5x$10^6$ $M^{-1}$, at least $10^6$ $M^{-1}$, at least $10^7$ $M^{-1}$, at least 5x$10^7$ $M^{-1}$, at least $10^8$ $M^{-1}$, at least $5\times10^8$ $M^{-1}$, at least $5\times10^9$ $M^{-1}$, at least $10^9$ $M^{-1}$, at least $5\times10^{10}$ $M^{-1}$, at least $10^{10}$ $M^{-1}$, at least $5\times10^{11}$ $M^{-1}$, at least $10^{11}$ $M^{-1}$, at least $5\times10^{12}$ $M^{-1}$, at least $10^{12}$ $M^{-1}$, at least $5\times10^{13}$ $M^{-1}$ at least $10^{13}$ $M^{-1}$, at least $5\times10^{14}$ $M^{-1}$, at least $10^{14}$ $M^{-1}$, or with a $K_A$ of any range between any pair of the foregoing values (e.g., $5\times10^4$ $M^{-1}$ to $10^{13}$ $M^{-1}$ or $5\times10^7$ $M^{-1}$ to $5\times10^{13}$ $M^{-1}$).

In various embodiments, a CTLA4 of the disclosure binds to CD80 with a $K_D$ ($k_{off}/k_{on}$) of $5\times10^{-6}$M or less, $10^{-6}$ M or less, $5\times10^{-7}$ M or less, $10^{-7}$ M or less, $5\times10^{-8}$ M or less, $10^{-8}$ M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $5\times10^{-13}$ M or less, $10^{-13}$M or less, $5\times10^{-14}$ M or less, $10^{-14}$ M or less, $5\times10^{-15}$M or less, $10^{-15}$ M or less, or with a $K_D$ of any range between any pair of the foregoing values (e.g., $10^{-7}$ M to $5\times10^{-13}$M, or $5\times10^{-9}$ M to $10^{-15}$ M).

In various embodiments, a CTLA4 protein of the disclosure binds to CD86 with a $K_D$ ($k_{off}/k_{on}$) of $10^{-5}$ M or less, $5\times10^{-6}$ M or less, $10^{-6}$ M or less, $5\times10^{-7}$ M or less, $10^{-7}$ M or less, $5\times10^{-8}$ M or less, $10^{-8}$ M or less, $5\times10^{-9}$ M or less, $10^{-9}$ M or less, $5\times10^{-10}$ M or less, $10^{-10}$ M or less, $5\times10^{-11}$ M or less, $10^{-11}$ M or less, $5\times10^{-12}$ M or less, $10^{-12}$ M or less, $5\times10^{-13}$ M or less, $10^{-13}$ M or less, $5\times10^{-14}$M or less, $10^{-14}$ M or less, $5\times10^{-15}$ M or less, $10^{-15}$ M or less, or with a $K_D$ of any range between any pair of the foregoing values (e.g., $10^{-6}$ M to $5\times10^{-10}$ M, or $5\times10^{-9}$ M to $10^{-15}$ M).

In some embodiments, the CTLA4 protein of the disclosure binds to CD80 and inhibits the binding of CD80 to abatacept in a binding assay (e.g., an AlphaLISA® competition assay) at an $IC_{50}$ value of less than 1000 nM, less than 750 nM, less than 500 nM, less than 100 nM, less than 50 nM, less than 10 nM, less than 5 nM, less than 1 nM, less than 0.75 nM, less than 0.5 nM, less than 0.25 nM, less than 0.1 nM, less than $5\times10^{-2}$ nM, less than $10^{-2}$ nM, less than $5\times10^{-3}$ nM, less than $10^{-3}$ nM, less than $5\times10^{-4}$ nM, or less than $10^{-4}$ nM, or with an $IC_{50}$ of any range between any pair of the foregoing values (e.g., 100 nM to $5\times10^{-2}$ nM or 0.5 nM and $5\times10^{-4}$ nM).

In some embodiments, the CTLA4 protein of the disclosure binds to CD86 and inhibits the binding of CD86 to abatacept in a binding assay (e.g., an AlphaLISA® competition assay) at an $IC_{50}$ value of less than 1000 nM, less than 500 nM, less than 100 nM, less than 50 nM, less than 10 nM, less than 5 nM, less than 1 nM, less than 0.75 nM, less than 0.5 nM, less than 0.25 nM, less than 0.1 nM, less than $5\times10^{-2}$ nM, less than $10^{-2}$ nM, less than $5\times10^{-3}$ nM, less than $10^{-3}$ nM, less than $5\times10^{-4}$ nM, or less than $10^{-4}$ nM, or with an $IC_{50}$ of any range between any pair of the foregoing values (e.g., 100 nM to $5\times10^{-2}$ nM or 0.5 nM and $5\times10^{-4}$ nM).

In certain embodiments, the kinetic properties of a fusion protein of the disclosure are comparable to, or improved relative to, abatacept in a comparable assay. For example, in certain embodiments, a CTLA4 protein of the disclosure binds to CD80 and/or CD86 with a $k_{on}$ rate ranging from approximately 0.05× to 1000× of the $k_{on}$ of abatacept, for example a $k_{on}$ of 0.06× of the $k_{on}$ of abatacept, a $k_{on}$ of 0.08× of the $k_{on}$ of abatacept, a $k_{on}$ of 0.1× of the $k_{on}$ of abatacept, a $k_{on}$ of 0.5× of the $k_{on}$ of abatacept, a $k_{on}$ of 1× of the $k_{on}$ of abatacept, a $k_{on}$ of 1.1× of the $k_{on}$ of abatacept, a $k_{on}$ of 1.2× of the $k_{on}$ of abatacept, a $k_{on}$ of 1.3× of the $k_{on}$ of abatacept, a $k_{on}$ of 1.4× of the $k_{on}$ of abatacept, a $k_{on}$ of 1.5× of the $k_{on}$ of abatacept, a $k_{on}$ of 1.6× of the $k_{on}$ of abatacept, a $k_{on}$ of 1.6× of the $k_{on}$ of abatacept, a $k_{on}$ of 1.7× of the $k_{on}$ of abatacept, a $k_{on}$ of 1.8× of the $k_{on}$ of abatacept, a $k_{on}$ of 1.9× of the $k_{on}$ of abatacept, a $k_{on}$ of 2× of the $k_{on}$ of abatacept, a $k_{on}$ of 2.25× of the $k_{on}$ of abatacept, a $k_{on}$ of 2.5× of the $k_{on}$ of abatacept, a $k_{on}$ of 2.75× of the $k_{on}$ of traztuzumab, a $k_{on}$ of 3× of the $k_{on}$ of abatacept, a $k_{on}$ of 4× of the $k_{on}$ of abatacept, a $k_{on}$ of 5× of the $k_{on}$ of abatacept, a $k_{on}$ of 6× of the $k_{on}$ of abatacept, a $k_{on}$ of 7× of the $k_{on}$ of abatacept, a $k_{on}$ of 8× of the $k_{on}$ of abatacept, a $k_{on}$ of 9× of the $k_{on}$ of abatacept, a $k_{on}$ of 10× of the $k_{on}$ of abatacept, a $k_{on}$ of 15× of the $k_{on}$ of abatacept, a $k_{on}$ of 20× of the $k_{on}$ of abatacept, a $k_{on}$ of 50× of the $k_{on}$ of abatacept, a $k_{on}$ of 75× of the $k_{on}$ of abatacept, a $k_{on}$ of 100× of the $k_{on}$ of abatacept, a $k_{on}$ of 150× of the $k_{on}$ of abatacept, a $k_{on}$ of 200× of the $k_{on}$ of abatacept, or a $k_{on}$ ranging between any pair of the foregoing values, e.g., a $k_{on}$ of 0.1×-75× of the $k_{on}$ of abatacept, a $k_{on}$ of 5×-100× of the $k_{on}$ of abatacept, a $k_{on}$ of 0.05×-1000× of the $k_{on}$ of abatacept, a $k_{on}$ of 0.75×-250× of the $k_{on}$ of abatacept, etc.

In various embodiments, a CTLA4 protein of the disclosure binds to CD80 and/or CD86 with a $k_{off}$ rate ranging from about 0.001× to about 3× of the $k_{off}$ of abatacept, for example a $k_{off}$ of 0.002× of the $k_{off}$ of abatacept, a $k_{off}$ of 0.003× of the $k_{off}$ of abatacept, a $k_{off}$ of 0.004× of the $k_{off}$ of abatacept, a $k_{off}$ of 0.005× of the $k_{off}$ of abatacept, a $k_{off}$ of 0.006× of the $k_{off}$ of abatacept, a $k_{off}$ of 0.0075× of the $k_{off}$ of abatacept, a $k_{off}$ of 0.01× of the $k_{off}$ of abatacept, a $k_{off}$ of 0.025× of the $k_{off}$ of abatacept, a $k_{off}$ of 0.05× of the $k_{off}$ of abatacept, a $k_{off}$ of 0.075× of the $k_{off}$ of abatacept, a $k_{off}$ of 0.1× of the $k_{off}$ of abatacept, a $k_{off}$ of 0.25× of the $k_{off}$ of abatacept, a $k_{off}$ of 0.5× of the $k_{off}$ of abatacept, a $k_{off}$ of 0.75× of the $k_{off}$ of abatacept, a $k_{off}$ of 1× of the $k_{off}$ of abatacept, a $k_{off}$ of 1.25× of the $k_{off}$ of abatacept, a $k_{off}$ of 1.5× of the $k_{off}$ of abatacept, a $k_{off}$ of 1.75× of the $k_{off}$ of abatacept, a $k_{off}$ of 2× of the $k_{off}$ of abatacept, a $k_{off}$ of 2.25× of the $k_{off}$ of abatacept, a $k_{off}$ of 2.5× of the $k_{off}$ of abatacept, a $k_{off}$ of 3× of the $k_{off}$ of abatacept, a $k_{off}$ of 4× of the $k_{off}$ of abatacept, a $k_{off}$ of 5× of the $k_{off}$ of abatacept, or a $k_{off}$ ranging between any pair of the foregoing values, e.g., a $k_{off}$ of 0.01× to 1.25× of the $k_{off}$ of abatacept, a $k_{off}$ of 0.05× to 2.5× of the $k_{off}$ of abatacept, or a $k_{off}$ of 0.006× to 0.1× of the $k_{off}$ of abatacept, etc.

In other embodiments, a CTLA4 protein of the disclosure binds to CD80 and/or CD86 with a $K_A$ ($k_{on}/k_{off}$) ranging from about 0.1× to about 1000× of the $K_A$ of abatacept, for example a $K_A$ of 0.2× of the $K_A$ of abatacept, a $K_A$ of 0.25× of the $K_A$ of abatacept, a $K_A$ of 0.5× of the $K_A$ of abatacept, a $K_A$ of 0.75 of the $K_A$ of abatacept, a $K_A$ of 1× of the $K_A$ of abatacept, a $K_A$ of 2× of the $K_A$ of abatacept, a $K_A$ of 3× of the $K_A$ of abatacept, a $K_A$ of 4× of the $K_A$ of abatacept, a $K_A$ of 5× of the $K_A$ of abatacept, a $K_A$ of 10× of the $K_A$ of abatacept, a $K_A$ of 15× of the $K_A$ of abatacept, a $K_A$ of 20× of the $K_A$ of abatacept, a $K_A$ of 30× of the $K_A$ of abatacept, a $K_A$ of 40× of the $K_A$ of abatacept, a $K_A$ of 50× of the $K_A$ of abatacept, a $K_A$ of 75× of the $K_A$ of abatacept, a $K_A$ of 100× of the $K_A$ of abatacept, a $K_A$ of 200× of the $K_A$ of abatacept, a $K_A$ of 250× of the $K_A$ of abatacept, a $K_A$ of 300× of the $K_A$ of abatacept, a $K_A$ of 350× of the $K_A$ of abatacept, a $K_A$ of 400× of the $K_A$ of abatacept, a $K_A$ of 500× of the $K_A$ of abatacept, a $K_A$ of 750× of the $K_A$ of abatacept, a $K_A$ of 1000× of the $K_A$ of abatacept, or a $K_A$ ranging between any pair of the foregoing values, e.g., a $K_A$ of 0.1× to 100× of the $K_A$ of abatacept, a $K_A$ of 10× to 50× of the $K_A$ of abatacept, or a $K_A$ of 5× to 50× of the $K_A$ of abatacept, etc.

In still other embodiments, a CTLA4 protein of the disclosure binds to CD80 and/or CD86 with a $K_D$ ($k_{off}/k_{on}$) ranging from about 0.001× to 10× of the $K_D$ of abatacept, or example a $K_D$ of 0.001× of the $K_D$ of abatacept, a $K_D$ of 0.002× of the $K_D$ of abatacept, a $K_D$ of 0.003× of the $K_D$ of abatacept, a $K_D$ of 0.004× of the $K_D$ of abatacept, a $K_D$ of 0.005× of the $K_D$ of abatacept, a $K_D$ of 0.0075× of the $K_D$ of abatacept, a $K_D$ of 0.01× of the $K_D$ of abatacept, a $K_D$ of 0.025× of the $K_D$ of abatacept, a $K_D$ of 0.05× of the $K_D$ of abatacept, a $K_D$ of 0.075× of the $K_D$ of abatacept, a $K_D$ of 0.1× of the $K_D$ of abatacept, a $K_D$ of 0.2× of the $K_D$ of abatacept, a $K_D$ of 0.3× of the $K_D$ of abatacept, a $K_D$ of 0.4× of the $K_D$ of abatacept, a $K_D$ of 0.5× of the $K_D$ of abatacept, a $K_D$ of 0.75× of the $K_D$ of abatacept, a $K_D$ of 1× of the $K_D$ of abatacept, a $K_D$ of 1.5× of the $K_D$ of abatacept, a $K_D$ of 2× of the $K_D$ of abatacept, a $K_D$ of 3× of the $K_D$ of abatacept, a $K_D$ of 4× of the $K_D$ of abatacept, a $K_D$ of 5× of the $K_D$ of abatacept, a $K_D$ of 6× of the $K_D$ of abatacept, a $K_D$ of 7× of the $K_D$ of abatacept, a $K_D$ of 8× of the $K_D$ of abatacept, a $K_D$ of 9× of the $K_D$ of abatacept, a $K_D$ of 10× of the $K_D$ of abatacept, or a $K_D$ ranging between any pair of the foregoing values, e.g., a $K_D$ of 0.001× of 0.5× of the $K_D$ of abatacept, a $K_D$ of 0.1× to 4× of the $K_D$ of abatacept, a $K_D$ of 0.05 to 1× of the $K_D$ of abatacept, etc.

In certain embodiments, a CTLA4 protein of the disclosure binds to CD80 and/or CD86 and inhibits cell growth or IL2 production at a $IC_{50}$ value ranging from about 0.001× to 10× of the $IC_{50}$ of abatacept, for example at an $IC_{50}$ of 0.005 of the $IC_{50}$ of abatacept, at an $IC_{50}$ of 0.01× of the $IC_{50}$ of abatacept, at an $IC_{50}$ of 0.05× of the $IC_{50}$ of abatacept, at an $IC_{50}$ of 0.1× of the $IC_{50}$ of abatacept, at an $IC_{50}$ of 0.2× of the $IC_{50}$ of abatacept, at an $IC_{50}$ of 0.3× of the $IC_{50}$ of abatacept, at an $IC_{50}$ of 0.4× of the $IC_{50}$ of abatacept, at an $IC_{50}$ of 0.5× of the $IC_{50}$ of abatacept, at an $IC_{50}$ of 0.6× of the $IC_{50}$ of abatacept, at an $IC_{50}$ of 0.7× of the $IC_{50}$ of abatacept, at an $IC_{50}$ of 0.8× of the $IC_{50}$ of abatacept, at an $IC_{50}$ of 0.9× of the $IC_{50}$ of abatacept, at an $IC_{50}$ of 1× of the $IC_{50}$ of abatacept, at an $IC_{50}$ of 1.5× of the $IC_{50}$ of abatacept, at an $IC_{50}$ of 2× of the $IC_{50}$ of abatacept, at an $IC_{50}$ of 3× of the $IC_{50}$ of abatacept, at an $IC_{50}$ of 4× of the $IC_{50}$ of abatacept, at an $IC_{50}$ of 5× of the $IC_{50}$ of abatacept, at an $IC_{50}$ of 6× of the $IC_{50}$ of abatacept, at an $IC_{50}$ of 7× of the $IC_{50}$ of abatacept, at an $IC_{50}$ of 8× of the $IC_{50}$ of abatacept, at an $IC_{50}$ of 9× of the $IC_{50}$ of abatacept, at an $IC_{50}$ of 10× of the $IC_{50}$ of abatacept, at an $IC_{50}$ of 100× of the $IC_{50}$ of the $IC_{50}$ of abatacept, at an $IC_{50}$ of 500× of the $IC_{50}$ of abatacept, at an $IC_{50}$ of 1000× of the $IC_{50}$ of abatacept, or an $IC_{50}$ ranging between any pair of the foregoing values, e.g., an $IC_{50}$ of 0.005 to 0.2 of the $IC_{50}$ of abatacept, an $IC_{50}$ of 0.1× to 1.5× of the $IC_{50}$ of abatacept, an $IC_{50}$ of 0.2× to 2× of the $IC_{50}$ of abatacept, etc. In certain embodiments, a single substitution in the CDR-like loops can result in the foregoing differences in $IC_{50}$ as compared to abatacept, wherein a CTLA4-Ig fusion protein of the disclosure can comprise such substitution and up to 5 additional substitutions, up to 10 additional substitutions, up to 15 additional substitutions or up to 20 additional substitutions in the CDR-like loops as compared to abatacept.

6.8. CTLA4 Protein Conjugates

The CTLA4 proteins of the disclosure include conjugates that are modified, e.g., by the covalent attachment of any type of molecule to the protein, such that covalent attachment does not interfere with binding to CD80 or CD86.

In certain aspects, a CTLA4 protein of the disclosure can be conjugated to an effector moiety or a label. The term "effector moiety" as used herein includes, for example, antineoplastic agents, drugs, toxins, biologically active proteins, for example enzymes, antibody or antibody fragments, synthetic or naturally occurring polymers, nucleic acids (e.g., DNA and RNA), radionuclides, particularly radioiodide, radioisotopes, chelated metals, nanoparticles and reporter groups such as fluorescent compounds or compounds which can be detected by NMR or ESR spectroscopy.

In one example, CTLA4 proteins can be conjugated to an effector moiety, such as a cytotoxic agent, a radionuclide or drug moiety to modify a given biological response. The effector moiety can be a protein or polypeptide, such as, for example and without limitation, a toxin (such as abrin, ricin A, *Pseudomonas* exotoxin, or Diphtheria toxin), a signaling molecule (such as α-interferon, β-interferon, nerve growth factor, platelet derived growth factor or tissue plasminogen activator), an immunosuppressant (such as cyclosporine A, tacrolimus, Campath-1H or a glucocorticoid) or anti-inflammatory agent (such as aspirin or naproxen) or a biological response modifier such as an antibody, anti-lymphocyte globulin, protein or cytokine (e.g., an anti-TNFα antibody or an antibody that affects cell migration, such as natalizumab).

In another example the effector moieties can be cytotoxins or cytotoxic agents. Examples of cytotoxins and cytotoxic agents include taxol, cytochalasin B, gramicidin D, ethidium bromide, emetine, mitomycin, etoposide, tenoposide, vincristine, vinblastine, colchicin, doxorubicin, daunorabicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector moieties also include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C5 and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, anthramycin (AMC), calicheamicins or duocarmycins), and anti-mitotic agents (e.g., vincristine and vinblastine).

Other effector moieties can include radionuclides such as, but not limited to, $^{111}In$ and $^{90}Y$, $Lu^{177}$, $Bismuth^{213}$, $Californium^{252}$, $Iridium^{192}$ and $Tungsten^{18s}$/$Rhenium^{188}$ and drugs such as, but not limited to, alkylphosphocholines, topoisomerase I inhibitors, taxoids and suramin.

Techniques for conjugating such effector moieties to proteins are well known in the art (see, e.g., Hellstrom et al., Controlled Drug Delivery, 2nd Ed., at pp. 623-53 (Robinson et al., eds., 1987)); Thorpe et al., 1982, Immunol. Rev. 62:119-58 and Dubowchik et al., 1999, Pharmacology and Therapeutics 83:67-123).

In certain aspects, a CTLA4 protein is conjugated to a small molecule toxin. In certain exemplary embodiments, a CTLA4 protein of the disclosure is conjugated to a dolastatin or dolostatin peptidic analog or derivative, e.g., an auristatin (U.S. Pat. Nos. 5,635,483 and 5,780,588). The dolastatin or auristatin drug moiety may be attached to the antibody through its N (amino) terminus, C (carboxyl) terminus or internally (WO 02/088172). Exemplary auristatin embodiments include the N-terminus linked monomethylauristatin drug moieties DE and DF, as disclosed in U.S. Pat. No. 7,498,298, which is hereby incorporated by reference in its entirety (disclosing, e.g., linkers and methods of preparing monomethylvaline compounds such as MMAE and MMAF conjugated to linkers).

In other exemplary embodiments, small molecule toxins include but are not limited to calicheamicin, maytansine (U.S. Pat. No. 5,208,020), trichothene, and CC1065. In one embodiment of the disclosure, the CTLA4 protein is conjugated to one or more maytansine molecules (e.g., about 1 to about 10 maytansine molecules per protein molecule). Maytansine may, for example, be converted to May-SS-Me which may be reduced to May-SH3 and reacted with a protein (Chari et al., 1992, Cancer Research 52: 127-131) to generate a maytansinoid-protein or maytansinoid-Fc fusion conjugate. Structural analogues of calicheamicin that can also be used include but are not limited to γ11, γ31, γ31, N-acetyl-γ11, PSAG, and θ11, (Hinman et al., 1993, Cancer Research 53:3336-3342; Lode et al., 1998, Cancer Research 58:2925-2928; U.S. Pat. Nos. 5,714,586; 5,712,374; 5,264,586; 5,773,001).

In certain aspects, a CTLA4 protein of the disclosure can be attached to an immunosuppressant agent. Such agents include glucocorticoids, cytostatic agents, antibodies, drugs that act on immunophilins, statins and other agents such as interferons (e.g., INF-β and INF-γ), opioids, TNF binding agents (e.g., infliximab, etanercept, adalimumab, curcumin and catechins), mycophenolate, IL-1 receptor antagonists, and other small molecule agents (e.g., fingolimod, myriocin). Exemplary glucocorticoids include, but are not limited to, hydrocortisone, prednisone, prednisolone, methylprednisone, dexamethasone, betamethasone, triamcinolone, beclometasone, fludrocortisone acetate, deoxycorticosterone acetate, and aldosterone. Exemplary cytostatic agents include but are not limited to cyclophosphamide, nitrosoureas, platinum compounds, methotrexate, azathioprine, mercaptopurine, pyrimidine analogs, protein synthesis inhibitors, and antibiotics such as dactinomycin, anthracyclines, mitomycin C, bleomycin and mithramycin. Exemplary immunosuppressant antibodies include, but are not limited to, anti-$CD_{20}$ antibodies, anti-IL2 receptor antibodies (daclizumab, basiliximab), Campath-1H, anti-$\alpha_4\beta_1$ integrin antibodies, anti-IL-15 antibodies, anti-IL-6 receptor antibodies, and anti-CD3 antibodies (muromonab). Exemplary agents that act on immunophilins include but are not limited to cyclosporin, tacrolimus, and sirolimus.

In certain embodiments, CTLA4 proteins of the present disclosure can be attached to an anti-inflammatory agent. Exemplary anti-inflammatory agents include, but are not limited to, non-steroidal anti-inflammatories such as ibuprofen, aspirin, naproxen, diflunisal, ketoprofen, nabumetone, piroxicam, diclofenac, indomethacin, sulindac, tolmetin, etodolac, ketorolac, oxaprozin, and celecoxib, and glucocorticoids, which also have immunosuppressive activity.

In one example CTLA4 proteins of the present disclosure can be attached to poly(ethyleneglycol) (PEG) moieties. In one particular example the PEG moieties can be attached through any available amino acid side-chain or terminal amino acid functional group located in the protein, for example any free amino, imino, thiol, hydroxyl or carboxyl group. Such amino acids can occur naturally in the protein or can be engineered into the protein using recombinant DNA methods. See for example U.S. Pat. No. 5,219,996. Multiple sites can be used to attach two or more PEG molecules. PEG moieties can be covalently linked through a thiol group of at least one cysteine residue located in the CTLA4 protein. Where a thiol group is used as the point of attachment, appropriately activated effector moieties, for example thiol selective derivatives such as maleimides and cysteine derivatives, can be used. The CTLA4 proteins can be attached to PEG or other hydrophilic synthetic polymers, such as polypropylene glycol or polyoxyalkylene, using techniques well known in the art, such as those described in U.S. Pat. Nos. 4,179,337, 4,301,144, 4,496,689, 4,640,835, 4,670,417, and 4,791,192, or to a polymer such as polyvinylalcohol or polyvinylpyrrolidone (PVP).

The word "label" when used herein refers to a detectable compound or composition which can be conjugated directly or indirectly to a CTLA4 protein of the disclosure. The label can itself be detectable (e.g., radioisotope labels or fluorescent labels) or, in the case of an enzymatic label, can catalyze chemical alteration of a substrate compound or composition which is detectable. Useful fluorescent moieties include, but are not limited to, fluorescein, fluorescein isothiocyanate, rhodamine, 5-dimethylamine-1-napthalenesulfonyl chloride, phycoerythrin and the like. Useful enzymatic labels include, but are not limited to, alkaline phosphatase, horseradish peroxidase, glucose oxidase and the like.

Additional CTLA4 protein conjugates that are useful for, inter alia, diagnostic purposes, are described in Section 5.7 below.

6.9. Diagnostic Uses of CTLA4 Proteins

The CTLA4 proteins of the disclosure, including those proteins that have been modified, e.g., by biotinylation, horseradish peroxidase, or any other detectable moiety (including those described in Section 5.6), can be advantageously used for diagnostic purposes.

In particular, the CTLA4 proteins can be used, for example, but not limited to, to bind to CD80 and/or CD86 for leukocyte typing in vitro to define B-cell maturational stages, for detecting B-cell associated diseases, for isolation of CD80- and/or CD86-positive cells, and for in vitro and in vivo diagnostic methods. (See, e.g., Yokochi et al., 1982, J. Immunol. 128(2): 823-27.) For example, the proteins can be used in immunoassays for qualitatively and quantitatively measuring levels of CD80- and/or CD86-positive cells in biological samples. General guidance for performing such diagnostic techniques are found in, for example, Harlow et al., Antibodies: A Laboratory Manual, Second Edition (Cold Spring Harbor Laboratory Press, 1988) and Hampton R et al., Serological Methods A Laboratory Manual, (APS Press, 1990), each of which is incorporated by reference herein in its entirety.

In certain embodiments, the CTLA4 proteins of the disclosure can be used in assays to identify other agents, e.g., anti-CTLA4 antibodies or fragments thereof, that are capable of regulating T-cell/B-cell interactions. In particular, the assays identify agents capable of inhibiting the binding of a protein of the disclosure to CD80 and/or CD86. Assays useful for screening agents that regulate T-cell/B-cell interactions are known in the art and include, but are not limited to, competition ELISA assays.

The present disclosure further encompasses CTLA4 proteins or fragments thereof conjugated to a diagnostic agent. The proteins can be used diagnostically, for example, to detect expression of a target of interest in specific cells, tissues, or serum; or to monitor the development or progression of an immunologic response as part of a clinical testing procedure to, e.g., determine the efficacy of a given treatment regimen. Detection can be facilitated by coupling the protein to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the protein (or fragment thereof) or indirectly, through an intermediate (such as, for example, a linker known in the art) using techniques known in the art. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, acetylcholinesterase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, $^{131}I$, $^{111}In$ or $^{99}Tc$.

The disclosure provides for the detection of expression of CD80 and/or CD86 comprising contacting a biological sample (e.g., cells, tissues or bodily fluids) using one or more CTLA4 proteins of the disclosure (optionally conjugated to a detectable moiety), and detecting whether or not the sample is positive for CD80- and/or CD86-expressing cells, or whether the sample has altered (e.g., reduced or increased) numbers of cells expressing CD80 and/or CD86 as compared to a control sample.

Diseases that can be diagnosed using the present methods include, but are not limited to, the diseases described herein. In certain embodiments, the tissue or body fluid is peripheral blood, peripheral blood leukocytes, biopsy tissues such as breast or lymph node biopsies, and tissue.

6.10. Therapeutic Methods Using CTLA4 Proteins 6.10.1. Clinical Benefits

The CTLA4 proteins of the disclosure interact with CD80 and/or CD86 on antigen presenting cells and regulate the interaction of T-cells with CD80/CD86-positive cells. Accordingly, the proteins of the disclosure are useful for treating pathological conditions involving dysregulated T-cell interactions with CD80/CD86-positive cells, including antigen presenting cells.

As described above in Section 5.1, in certain embodiments, the variant CTLA4 polypeptides of the disclosure have different binding affinities for CD80 and CD86. In other embodiments, the variant CTLA4 polypeptides of the disclosure have comparable binding affinities for both CD80 and CD86. CD80 and CD86 bind to T-cell surface proteins (e.g., CD28 and CTLA4) and elicit different biological effects. For example, the binding of CD86 to CD28 on naive T-cells initiates T-cell responses. Thus, inhibiting or reducing CD86 binding to CD28, for example, by administering a variant CTLA4 polypeptide of the disclosure with high or neutral binding affinity for CD86, can inhibit the initiation of the T-cell response and lead to T-cell anergy. Furthermore, binding of CD80 to CTLA4 terminates the T-cell response. Therefore, inhibiting or reducing CD80 binding to CTLA4 on T-cells, for example, by administering a variant CTLA4 polypeptide of the disclosure for high or neutral binding affinity for CD80, can block the termination of responses and prolong T-cell responses.

Accordingly, in certain embodiments, variant CTLA4 polypeptides with high binding affinity for CD80 and with low binding affinity for CD86, or variant CTLA4 polypeptides with neutral binding affinity for CD80 and with low binding affinity for CD86 are useful for treating conditions requiring enhanced T-cell mediated killing of cells, such as cancer. In other embodiments, variant CTLA4 proteins with high affinity or neutral binding affinity for CD86 and low affinity for CD80, or variant CTLA4 proteins with high binding affinity for both CD80 and CD86 are useful for treating conditions resulting from enhanced T-cell mediated killing of cells, such as autoimmune diseases, or tissue, organ or cell transplant rejection.

In certain embodiments, the proteins of the disclosure are useful for treating neoplasms. The proteins of the disclosure are useful in the treatment of tumors, including cancers and benign tumors. Examples of cancer to be treated herein include, but are not limited to, melanoma, breast cancer, prostate cancer, bladder cancer and colorectal cancer. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as multiple myeloma, B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

More particularly, cancers that are amenable to treatment with the CTLA4 proteins of the disclosure include those that are CD80 and/or CD86 positive. In some embodiments, the variant proteins of the disclosure useful for cancer treatment have high affinity for CD80 and low affinity for CD86. In other embodiments, the variant proteins of the disclosure useful for cancer treatment have neutral affinity for CD80 and low affinity for CD86.

In certain aspects, the cancer treatment methods include before the step of administering to the patient a CTLA4 protein of the disclosure, a step of detecting CD80 and/or CD86 on cancer cells. Said detecting step can be accomplished by any method known in the art, including, but not limited to, an immunohistochemistry assay to measure CD80 and/or CD86 protein levels on cancer cells. In certain embodiments, immunohistochemistry assays can be performed using a labeled anti-CD80 and/or anti-CD86 antibodies.

In various embodiments, the proteins of the disclosure are useful for treating autoimmune diseases. In some embodiments, the proteins of the disclosure are useful for treating patients with an autoimmune disease who have not been previously treated for the disease. In other embodiments, the proteins of the disclosure are useful for treating patients with an autoimmune disease who had an inadequate response to treatment with methotrexate, a disease-modifying antirheumatic drug, or an anti-TNFα antagonist. In various embodiments, the CTLA4 proteins of the disclosure are useful for treating an autoimmune disease selected from rheumatoid arthritis and juvenile idiopathic arthritis. In some embodiments, the proteins of the disclosure are useful for treating an autoimmune disease selected from ankylosing spondilitis, scleroderma, multiple sclerosis, and systemic lupus erythematosus.

More particularly, the CTLA4 proteins of the disclosure are useful for treating an autoimmune disease selected from acute disseminated encephalomyelitis (ADEM), acute necrotizing hemorrhagic leukoencephalitis, Addison's disease, agammaglobulinemia, allergic asthma, allergic rhinitis, alopecia greata, amyloidosis, ankylosing spondylitis, anti-GBM/anti-TBM nephritis, antiphospholipid syndrome (APS), autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune pancreatitis, autoimmune retinopathy, autoimmune thrombocytopenic purpura (ATP), autoimmune thyroid disease, axonal & neuronal neuropathies, Balo disease, Behcet's disease, bullous pemphigoid, cardiomyopathy, Castleman disease, celiac sprue (nontropical), Chagas disease, autoimmune conditions associated with chronic fatigue syndrome or fibromyalgia, chronic inflammatory demyelinating polyneuropathy (CIDP), chronic recurrent multifocal ostomyelitis (CRMO), Churg-Strauss syndrome, icatricial pemphigoid/benign mucosal pemphigoid, Crohn's disease, Cogans syndrome, cold agglutinin disease, congenital heart block, coxsackie myocarditis, CREST disease, essential mixed cryoglobulinemia, demyelinating neuropathies, dermatomyositis, Devic's disease (neuromyelitis optica), discoid lupus, Dressler's syndrome, endometriosis, eosinophilic fasciitis, erythema nodosum, experimental allergic encephalomyelitis, Evans syndrome, fibrosing alveolitis, giant cell arteritis (temporal arteritis), glomerulonephritis, Goodpasture's syndrome, Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, immunoregulatory lipoproteins, inclusion body myositis, insulin-dependent diabetes (typel), interstitial cystitis, juvenile arthritis, juvenile diabetes, Kawasaki syndrome, Lambert-Eaton syndrome, leukocytoclastic vasculitis, lichen planus, lichen sclerosus, ligneous conjunctivitis, linear IgA disease (LAD), lupus (SLE), Lyme disease, Meniere's disease, microscopic polyangiitis, mixed connective tissue disease (MCTD), Mooren's ulcer, Mucha-Habermann disease, multiple sclerosis, myasthenia gravis, myositis, narcolepsy, neuromyelitis optica (see Devic's), neutropenia, ocular cicatricial pemphigoid, optic neuritis, palindromic rheumatism, PANDAS (Pediatric Autoimmune Neuropsychiatric Disorders Associated with *Streptococcus*), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatica, polymyositis, postmyocardial infarction syndrome, postpericardiotomy syndrome, progesterone dermatitis, primary biliary cirrhosis, primary sclerosing cholangitis, psoriasis, psoriatic arthritis, idiopathic pulmonary fibrosis, pyoderma gangrenosum, pure red cell aplasia, Raynauds phenomenon, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjogren's syndrome, sperm & testicular autoimmunity, stiff person syndrome, subacute bacterial endocarditis (SBE), sympathetic ophthalmia, Takayasu's arteritis, temporal arteritis/Giant cell arteritis, thrombocytopenic purpura (TTP), Tolosa-Hunt syndrome, transverse myelitis, ulcerative colitis, undifferentiated connective tissue disease (UCTD), uveitis, vasculitis, vesiculobullous dermatosis, vitiligo, and Wegener's granulomatosis.

In certain embodiments, the variant proteins of the disclosure useful for treating an autoimmune disease have high affinity for CD86 and low affinity for CD80. In other embodiments, the variant proteins of the disclosure useful for treating an autoimmune disease have neutral affinity for CD86 and low affinity for CD80. In other embodiments, the variant proteins of the disclosure have high affinity for both CD86 and CD80.

In various embodiments, the CLTA4 proteins of the disclosure are useful for treating rejection of cell, organ and tissue graft transplants, graft versus host disease and/or for inducing xenograft tolerance, e.g., islet xenograft tolerance in patients with type 1 diabetes mellitus. In some embodiments, the variant proteins of the disclosure have high affinity for CD86 and low affinity for CD80. In other embodiments, the variant proteins of the disclosure have neutral affinity for CD86 and low affinity for CD80. In still other embodiments, the variant proteins of the disclosure have high affinity for both CD86 and CD80.

In some embodiments, the proteins of the disclosure are useful for treating infections caused by the proliferation of viruses that depend on T-cell activation. Such viruses include, but are not limited to, HTLV-1, HIV-1 and HIV2 viruses.

Accordingly, the present disclosure provides methods of treating any of the foregoing diseases in a patient in need thereof, comprising: administering to the patient a CTLA4 protein of the disclosure. Optionally, said administration is repeated, e.g., after one day, two days, three days, five days, one week, two weeks, three weeks, one month, five weeks, six weeks, seven weeks, eight weeks, two months or three months. The repeated administration can be at the same dose or at a different dose. The administration can be repeated once, twice, three times, four times, five times, six times, seven times, eight times, nine times, ten times, or more. For example, according to certain dosage regimens a patient receives CTLA4 therapy for a prolonged period of time, e.g., 6 months, 1 year or more. In various embodiments, periods of CTLA4 therapy are alternated with periods of no CTLA4 therapy. The amount of protein administered to the patient is in certain embodiments a therapeutically effective amount. As used herein, a "therapeutically effective" amount of a CTLA4 protein can be administered as a single dose or over the course of a therapeutic regimen, e.g., over the course of a week, two weeks, three weeks, one month, three months, six months, one year, or longer. Exemplary therapeutic regimens are described in Section 5.8.4 below.

In certain embodiments, the CTLA4 therapy is commenced at or near the onset of disease, such as from 1 day to 6 months after onset of the disease. In some embodiments, CTLA4 therapy is commenced after the disease has progressed, such as from 6 months to 1 year, 2 years, or 3 years or more after the onset of disease. In other embodiments, CTLA4 therapy is administered during periods of disease remission. In still other embodiments, CTLA4 therapy is administered during periods of active disease. The timing of administration of CTLA4 therapy will depend upon factors known to the skilled artisan, such as the nature of the disease and the role of the CD28-CD80/CD86 costimulatory pathway in the disease being treated.

According to the present disclosure, treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom the CTLA4 proteins of the disclosure is administered is preferably a mammal such as a non-primate (e.g., cow, pig, horse, cat, dog, rat, etc.) or a primate (e.g., monkey or human). In certain embodiments, the subject or patient is a human. In certain aspects, the human is an adult patient. In other aspects, the human is a pediatric patient.

6.10.2. Pharmaceutical Compositions and Routes of Administration

Compositions comprising a CTLA4 protein of the disclosure and, optionally one or more additional therapeutic agents, such as the combination therapeutic agents described in Section 5.8.3 below, are provided herein. The compositions will usually be supplied as part of a sterile, pharmaceutical composition that will normally include a pharmaceutically acceptable carrier. This composition can be in any suitable form (depending upon the desired method of administering it to a patient).

The CTLA4 proteins of the disclosure can be administered to a patient by a variety of routes such as orally, transdermally, subcutaneously, intranasally, intravenously, intramuscularly, intraocularly, topically, intrathecally and intracerebroventricularly. The most suitable route for administration in any given case will depend on the particular protein, the subject, and the nature and severity of the disease and the physical condition of the subject.

For treatment of indications described herein, the effective dose of CTLA4 protein of the disclosure can range from about 0.1 to about 75 mg/kg per single (e.g., bolus) administration, multiple administrations or continuous administration, or to achieve a serum concentration of 0.01-5000 μg/ml serum concentration per single (e.g., bolus) administration, multiple administrations or continuous administration, or any effective range or value therein depending on the condition being treated, the route of administration and the age, weight and condition of the subject. In certain embodiments, e.g., for the treatment of rheumatoid arthritis, each dose can range from about 0.2 mg to about 50 mg per kilogram of body weight, for example from about 0.5 mg to about 20 mg per kilogram body weight. The CTLA4 protein can be formulated as an aqueous solution and administered by infusion.

Pharmaceutical compositions can be conveniently presented in unit dose forms containing a predetermined amount of a CTLA4 protein of the disclosure per dose. Such a unit can contain for example but without limitation 0.1 mg to 5 g, for example 1 mg to 1 g, 100 mg to 500 mg, or 10 mg to 50 mg. Pharmaceutically acceptable carriers for use in the disclosure can take a wide variety of forms depending, e.g., on the condition to be treated or route of administration.

Therapeutic formulations of the CTLA4 proteins of the disclosure can be prepared for storage as lyophilized formulations or aqueous solutions by mixing the protein having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can be present at concentration ranging from about 2 mM to about 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid monosodium succinate mixture, succinic acid-sodium hydroxide mixture, succinic acid disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives for use with the present disclosure include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions of the present disclosure and include polhydric sugar alcohols, for example trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Nonionic surfactants can be present in a range of about 0.05 mg/ml to about 1.0 mg/ml, for example about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a combination therapeutic agent in addition to the CTLA4 protein of the disclosure. Examples of suitable combination therapeutic agents are provided in Section 5.8.3 below.

The dosing schedule for administration by infusion can vary from once every six months to daily depending on a number of clinical factors, including the type of disease, severity of disease, and the patient's sensitivity to the CTLA4 protein.

The dosage of a CTLA4 protein of the disclosure to be administered will vary according to the particular antibody, the type of disease, the subject, and the severity of the disease, the physical condition of the subject, the therapeutic regimen (e.g., whether a combination therapeutic agent is used), and the selected route of administration; the appropriate dosage can be readily determined by a person skilled in the art.

It will be recognized by one of skill in the art that the optimal quantity and spacing of individual dosages of a CTLA4 protein of the disclosure will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop, the amount and/or frequency of the dosage can be altered or reduced, in accordance with normal clinical practice.

6.10.3. Combination Therapy

Described below are combinatorial methods in which the CTLA4 proteins of the disclosure can be utilized. The combinatorial methods of the disclosure involve the administration of at least two agents to a patient, the first of which is a CTLA4 protein of the disclosure, and the second of which is a combination therapeutic agent. The CTLA4 protein and the combination therapeutic agent can be administered simultaneously, sequentially or separately.

The combinatorial therapy methods of the present disclosure can result in a greater than additive effect, providing therapeutic benefits where neither the CTLA4 protein nor the combination therapeutic agent is administered in an amount that is alone therapeutically effective.

In the present methods, the CTLA4 protein of the disclosure and the combination therapeutic agent can be administered concurrently, either simultaneously or successively. As used herein, the CTLA4 protein of the disclosure and the combination therapeutic agent are said to be administered successively if they are administered to the patient on the same day, for example during the same patient visit. Successive administration can occur 1, 2, 3, 4, 5, 6, 7 or 8 hours apart. In contrast, the CTLA4 antibody of the disclosure and the combination therapeutic agent are said to be administered separately if they are administered to the patient on the different days, for example, the CTLA4 protein of the disclosure and the combination therapeutic agent can be administered at a 1-day, 2-day or 3-day, one-week, 2-week or monthly intervals. In the methods of the present disclosure, administration of the CTLA4 protein of the disclosure can precede or follow administration of the combination therapeutic agent.

As a non-limiting example, the CTLA4 protein of the disclosure and combination therapeutic agent can be administered concurrently for a period of time, followed by a second period of time in which the administration of the CTLA4 protein of the disclosure and the combination therapeutic agent is alternated.

Because of the potentially synergistic effects of administering a CTLA4 protein of the disclosure and a combination therapeutic agent, such agents can be administered in amounts that, if one or both of the agents is administered alone, is/are not therapeutically effective.

In certain aspects, the combination therapeutic agent is a chemotherapeutic agent, an anti-rheumatic, an anti-inflammatory agent, a radiotherapeutic, an immunosuppressive agent, or a cytotoxic drug.

Anti-rheumatic drugs for use in the combination therapies described herein include, but are not limited to, anakinra, auranofin, azathioprine, chloroquine, D-penicillamine, gold sodium thiomalate, hydroxychloroquine, Myocrisin, sulfasalazine methotrexate, cyclophosphamide, leflunomide, and minocycline.

In certain embodiments, the anti-rheumatic drug is a TNF-$\alpha$ antagonist including, but not limited to, agents such as infliximab (REMICADE®; Centocor) or a derivative, analog or antigen-binding fragment thereof, adalimumab (HUMIRA®; Abbott) or a derivative, analog or antigen-binding fragment thereof, golimumab (SIMPONI™; Centocor), or a derivative, analog or antigen-binding fragment thereof, certolizumab pegol (CIMZIA®, UCB) or a derivative, analog or antigen-binding fragment thereof, etanercept (ENBREL®, Amgen) or a fragment, derivative or analog thereof, IL-10, thalidomide, xanthine derivatives such as pentoxifylline, and Bupropion (WELLBUTRIN®, GlaxoSmithKline).

For treatment of cancer, a cancer vaccine can be used in combination with a CTLA4 protein of the disclosure. Suitable cancer vaccines include those that are targeted to cancer-causing viruses, such as the hepatitis B vaccine for liver cancer and the human papilloma virus vaccine for cervical cancer (Gardasil® and Cervarix®). Other cancer vaccines that can be used in the combination with the methods of the disclosure include, but are not limited to, Provenge® (Dendreon, Seattle Wash.) and GVAX® for prostate cancer, OncoVex$^{GM\text{-}CSF}$ for melanoma (BioVex, Woburn Mass.), Lucanix™ for non-small cell lung cancer, Stimuvax® for breast cancer, and Oncophage® for kidney cancer (Antigenics, Lexington Mass.). In certain embodiments, a cancer vaccine is administered prior to administration of a CTLA4 polypeptide of the disclosure.

For treatment of cancer, autoimmune diseases, or transplant rejection an anti-inflammatory agent can be used in combination with the CTLA4 proteins of the disclosure. Suitable anti-inflammatory agents for use in the methods described herein include, but are not limited to, ibuprofen, aspirin, naproxen, diflunisal, ketoprofen, nabumetone, piroxicam, diclofenac, indomethacin, sulindac, tolmetin, etodolac, ketorolac, oxaprozin, celecoxib, acetaminophen, diphenhydramine, meperidine, dexamethasone, pentasa, mesalazine, asacol, codeine phosphate, benorylate, and fenbufen.

For treatment of autoimmune diseases or transplant rejection, an immunosuppressant can be used in combination with the CTLA4 proteins of the disclosure. Suitable immunosuppressants for use in the methods described herein include, but are not limited to, hydrocortisone, prednisone, prednisolone, methylprednisone, dexamethasone, betamethasone, triamcinolone, beclometasone, fludrocortisone acetate, deoxycorticosterone acetate, aldosterone, cyclophosphamide, nitrosoureas, platinum compounds, methotrexate, azathioprine, mercaptopurine, pyrimidine analogs, protein synthesis inhibitors, dactinomycin, anthracyclines, mitomycin C, bleomycin, mithramycin, rapamycin, cyclosporin, tacrolimus, sirolimus, mycophenolic acid, mizoribine, 15-deoxyspergualin, mycophenolate mofetil (MMF), anti-thymocyte globulin, an anti-CD20 antibody or derivative, analog or antigen binding fragment thereof, an anti-IL2 receptor antibody (daclizumab, basiliximab) or a derivative, analog or antigen binding fragment thereof, Campath-1H, an anti-$\alpha_4\beta_1$ integrin antibody or a derivative, analog or antigen binding fragment thereof, an anti-IL-15 antibody or a derivative, analog or antigen binding fragment thereof, an anti-IL-6 receptor antibody or a derivative, analog or antigen binding fragment thereof, an anti-CD3 antibody(muromonab) or a derivative, analog or antigen binding fragment thereof, an anti-MHC antibody, or a derivative, analog or antigen binding fragment thereof, an anti-CD2 antibody, or a derivative, analog or antigen binding fragment thereof, an anti-CD4 antibody, or a derivative, analog or antigen binding fragment thereof, an anti-CD11a/CD18 antibody, or a derivative, analog or antigen binding fragment thereof, an anti-CD7 antibody, or a derivative, analog or antigen binding fragment thereof, an anti-CD27 antibody, or a derivative, analog or antigen binding fragment thereof, an anti-CD80 and/or anti-CD86 antibody (e.g., ATCC HB-253, ATCC CRL-2223, ATCC CRL-2226, ATCC HB-301, ATCC HB-11341, etc), or a derivative, analog or antigen binding fragment thereof, an anti-CD40 antibody (e.g., ATCC HB-9110), or a derivative, analog or antigen binding fragment thereof, or a derivative, analog or antigen binding fragment thereof, an anti-CD45 antibody, or a derivative, analog or antigen binding fragment thereof, an anti-CD58 antibody, or a derivative, analog or antigen binding fragment thereof, an anti-CD137 antibody, or a derivative, analog or antigen binding fragment thereof, an anti-ICOS antibody, or a derivative, analog or antigen binding fragment thereof, an anti-CD150 antibody, or a derivative, analog or antigen binding fragment thereof, an anti-OX40 antibody, or a derivative, analog or antigen binding fragment thereof, an anti-4-1BB antibody, or a derivative, analog or antigen binding fragment thereof, and low molecular weight adhesion antagonists such as LFA-1 antagonists, selectin antagonists and VLA-4 antagonists.

Other immunomodulatory compounds for use in the combination methods described herein include, but are not limited to, soluble gp39 (also known as CD40 ligand (CD40L), CD154, T-BAM, TRAP), soluble CD29, soluble CD40, soluble CD80 (e.g., ATCC 68627), soluble CD86, soluble CD28 (e.g., 68628), soluble CD56, soluble Thy-1, soluble CD3, soluble TCR, soluble VLA-4, soluble VCAM-1, soluble LECAM-1, soluble ELAM-1, soluble CD44, antibodies reactive with gp39 (e.g., ATCC HB-10916, ATCC HB-12055 and ATCC HB-12056), antibodies reactive with CD28 (e.g., ATCC HB-11944 or mAb 9.3 as described by Martin et al. (J. Clin. Immun. 4(1):18-22, 1980), antibodies reactive with LFA-1 (e.g., ATCC HB-9579 and ATCC TIB-213), antibodies reactive with LFA-2, antibodies reactive with IL-12, antibodies reactive with IFN-γ, antibodies reactive with CD48, antibodies reactive with any ICAM (e.g., ICAM-1 (ATCC CRL-2252), ICAM-2 and ICAM-3), antibodies reactive with CTLA4 (e.g., ATCC HB-304), antibodies reactive with Thy-1, antibodies reactive with CD56, antibodies reactive with CD29, antibodies reactive with TCR, antibodies reactive with VLA-4, antibodies reactive with VCAM-1, antibodies reactive with LECAM-1, antibodies reactive with ELAM-1, antibodies reactive with CD44.

For treatment of cancers, chemotherapeutic agents can suitably be used in combination with the CTLA4 proteins of the disclosure. Chemotherapeutic agents include, but are not limited to, radioactive molecules, toxins, also referred to as cytotoxins or cytotoxic agents, which includes any agent that is detrimental to the viability of cells, agents, and liposomes or other vesicles containing chemotherapeutic compounds. Examples of suitable chemotherapeutic agents include but are not limited to 1-dehydrotestosterone, 5-fluorouracil decarbazine, 6-mercaptopurine, 6-thioguanine, actinomycin D, adriamycin, aldesleukin, an anti-α5β1 integrin antibody, alkylating agents, allopurinol sodium, altretamine, amifostine, anastrozole, anthramycin (AMC)), anti-mitotic agents, cisdichlorodiamine platinum (II) (DDP) cisplatin), diamino dichloro platinum, anthracyclines, antibiotics, antimetabolites, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, *E. coli* L-asparaginase, eolociximab, emetine, epoetin-α, *Erwinia* L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, tretinoin, valrubicin, vinblastine sulfate, vincristine sulfate, and vinorelbine tartrate.

Sometimes, for treatment of cancers it may be beneficial to also administer one or more cytokines to the patient. In a preferred embodiment, the CTLA4 protein is co-administered with a growth inhibitory agent. Suitable dosages for the growth inhibitory agent are those presently used and may be lowered due to the combined action (synergy) of the growth inhibitory agent and CTLA4 protein.

6.10.4. Therapeutic Regimens

The present disclosure provides therapeutic regimens involving the administration of the CTLA4-Ig fusion proteins of the disclosure. The therapeutic regimen will vary depending on the patient's age, weight, and disease condition. The therapeutic regimen can continue for 2 weeks to indefinitely. In specific embodiments, the therapeutic regimen is continued for 2 weeks to 6 months, from 3 months to 5 years, from 6 months to 1 or 2 years, from 8 months to 18 months, or the like. The therapeutic regimen can be a non-variable dose regimen or a multiple-variable dose regimen.

For the dosage exemplary regimens described below, the CTLA4-Ig fusion proteins can be administered as a sterile, preservative-free solution for intravenous infusion.

For treatment of rheumatoid arthritis in adults weighing less than 60 kg, a CTLA4-Ig fusion protein of the disclosure is administered intravenously at an initial dose of 50 mg to 750 mg. In specific embodiments, the initial dose is 100-600 mg, 250-500 mg, 300-550 mg, 350-500 mg, 50-250 mg, or 400-600 mg. Following the initial dose, a CTLA4-Ig fusion protein of the disclosure is administered intravenously at 2 weeks and 4 weeks after the first infusion and every 4 weeks thereafter at a dose of 50-750 mg, such as 100-600 mg, such as 250-500 mg, such as 300-550 mg, such as 50-250 mg or at a dose of 400-600 mg.

For treatment of rheumatoid arthritis in adults weighing between 60 kg and 100 kg, a CTLA4-Ig fusion protein of the disclosure is administered intravenously at an initial dose of 75 mg to 1000 mg. In specific embodiments, the initial dose is 100-850 mg, 250-800 mg, 300-750 mg, 400-700 mg, 75-500 mg, 500-1000 mg or 600-800 mg. Following the initial dose, a CTLA4-Ig fusion protein of the disclosure is administered intravenously at 2 weeks and 4 weeks after the first infusion and every 4 weeks thereafter at a dose of 75-900 mg, such as 100-850 mg, such as 250-800 mg, such as 300-750 mg, such as 400-700 mg, such as 75-500 mg, such as 500-1000 mg or such as 600-800 mg.

For treatment of rheumatoid arthritis in adults weight more than 100 kg, a CTLA4-Ig fusion protein of the disclosure is administered intravenously at an initial dose of 100 mg to 1500 mg. In specific embodiments, the initial dose is 250-1250 mg, 500-1100 mg, 750-1000 mg, 100-800 mg, 250-900 mg or 700-1200 mg. Following the initial dose, a CTLA4-Ig fusion protein of the disclosure is administered intravenously at 2 weeks and 4 weeks after the first infusion and every 4 weeks thereafter at a dose of 100 mg to 1500 mg, such as 250-1250 mg, such as 500-1100 mg, such as 750-1000 mg, such as 100-800 mg, such as 250-900 mg or such as 700-1200 mg.

For treatment of juvenile idiopathic arthritis in patients between the ages of 6 and 17 who weigh less than 75 kg, a CTLA4-Ig fusion protein of the disclosure is administered intravenously at an initial dose of 0.1 to 15 mg/kg. In specific embodiments, the initial dose is 0.2-12.5 mg/kg, 0.5-12 mg/kg, 1-10.5 mg/kg, 2-10 mg/kg, 3-9 mg/kg, or 4-8.5 mg/kg. Following the initial dose, a CTLA4-Ig fusion protein of the disclosure is administered intravenously at 2 weeks and 4 weeks after the first infusion and every 4 weeks thereafter at a dose of 0.1 to 15 mg/kg, such as 0.2-12.5 mg/kg, 0.5-12 mg/kg, 1-10.5 mg/kg, 2-10 mg/kg, 3-9 mg/kg, or 4-8.5 mg/kg.

For treatment of juvenile idiopathic arthritis in patients aged 6 to 17 years who weigh more than 75 kg, a CTLA4-Ig fusion protein of the disclosure is administered intravenously at an initial dose of 75 mg to 1000 mg. In specific embodiments, the initial dose is 100-850 mg, 250-800 mg, 300-750 mg, 400-700 mg, 75-500 mg, 500-1000 or 600-800 mg. Following the initial dose, a CTLA4-Ig fusion protein of the disclosure is administered intravenously at 2 weeks and 4 weeks after the first infusion and every 4 weeks thereafter at a dose of 75-900 mg, such as 100-850 mg, such as 250-800 mg, such as 300-750 mg, such as 400-700 mg, such as 75-500 mg, such as 500-1000 mg or such as 600-800 mg. In these embodiments, the maximum does should not exceed 1000 mg.

In certain embodiments, the CTLA4-Ig fusion proteins of the disclosure are used to treat patients with rheumatoid arthritis who have had an inadequate response to methotrexate therapy or to therapy with an anti-TNFα agent (e.g., etanercept (Enbrel®), infliximab (Remicade®), adalimumab (Humira®), certolizumab pegol (Cimzia®), or sTNFR-IgG (lenercept)).

6.10.5. Diagnostic and Pharmaceutical Kits

Encompassed by the present disclosure are pharmaceutical kits containing the CTLA4 proteins (including conjugates of CTLA4 proteins) of the disclosure. The pharmaceutical kit is a package comprising the CTLA4 protein of the disclosure (e.g., either in lyophilized form or as an aqueous solution) and one or more of the following:

- A combination therapeutic agent, for example as described in Section 5.8.3 above;
- A device for administering the CTLA4 protein, for example a pen, needle and/or syringe; and
- Pharmaceutical grade water or buffer to resuspend the antibody if the protein is in lyophilized form.

In certain aspects, each unit dose of the CTLA4 protein is packaged separately, and a kit can contain one or more unit doses (e.g., two unit doses, three unit doses, four unit doses, five unit doses, eight unit doses, ten unit doses, or more). In a specific embodiment, the one or more unit doses are each housed in a syringe or pen.

Diagnostic kits containing the CTLA4 proteins (including protein conjugates) of the disclosure are also encompassed herein. The diagnostic kit is a package comprising the CTLA4 protein of the disclosure (e.g., either in lyophilized form or as an aqueous solution) and one or more reagents useful for performing a diagnostic assay. Where the CTLA4 protein is labeled with an enzyme, the kit can include substrates and cofactors required by the enzyme (e.g., a substrate precursor which provides the detectable chromophore or fluorophore). In addition, other additives can be included, such as stabilizers, buffers (e.g., a block buffer or lysis buffer), and the like. In certain embodiments, the CTLA4 protein included in a diagnostic kit is immobilized on a solid surface, or a solid surface (e.g., a slide) on which the protein can be immobilized is included in the kit. The relative amounts of the various reagents can be varied widely to provide for concentrations in solution of the reagents which substantially optimize the sensitivity of the assay. In a specific embodiment, the protein and one or more reagents can be provided (individually or combined) as dry powders, usually lyophilized, including excipients which on dissolution will provide a reagent solution having the appropriate concentration.

7. EXAMPLE 1

Identification of Variants of CTLA4-Ig with Affinity to CD80 and CD86

7.1. Materials and Methods 7.1.1. Production of CD80 and CD86 Proteins

CD80 and CD86 protein were expressed as monomeric secreted fusion proteins. The extracellular domain of either CD80 or CD86 was fused with human lambda constant region containing a Cys to Ser mutation to disrupt the intermolecular disulfide bond (Akamatsu et al., 2007, J. Immunol. Methods 327:40). The CD80-Cλ or CD86-Cλ fusion protein was expressed transiently in the culture supernatant of 293T cells. The production levels of these fusion proteins were estimated by ELISA, using goat anti-human lambda light chain antibody (Biosource, Camarillo, Calif.) for capturing and horseradish peroxidase (HRP)-conjugated goat anti-human lambda chain antibody (Southern Biotech, Birmingham, Ala.) for detection.

7.1.2. Binding of CTLA4-Ig Variants to CD80 and CD86

CD80 or CD86 fused with a Cλ-HA tag was bound to AlphaLISA® acceptor beads conjugated with goat anti-human Cλ antibody and biotinylated abatacept was bound to AlphaScreen® strepavidin-coated donor beads (Perkin Elmer, Waltham, Mass.). Abatacept was biotinylated with Sulfo-NHS-Biotin using standard methods and dialyzed in PBS. Conjugation of AlphaLISA® acceptor beads was performed by following the manufacturer's instructions ("AlphaLISA® Assay Development Guide", Perkin Elmer). The binding assay was performed in a 384-well AlphaPlate (Perkin Elmer) in assay buffer (1% BSA, 0.01% Tween20 in PBS (pH 7.1)). Each well contained 0.5 nM biotinylated abatacept, 1:4 serially diluted unlabeled CTLA4-Ig variant protein starting from 40 nM, 0.078 μg/ml CD80, and 5 μg/ml goat anti-human Cλ-conjugated acceptor beads. The plate was incubated in the dark for 1 h at room temperature. Streptavidin donor beads were subsequently added to each well at 5 μg/ml. The plate was incubated in the dark at room temperature for an additional 30 min, after which it was read on an EnVision reader (Perkin Elmer). Data were fit using nonlinear regression with the software GRAPHPAD PRISM (GraphPad, San Diego). For the CD86 binding assays, 8 nM biotinylated abatacept, 1:4 serially diluted unlabeled CTLA4-Ig variant protein starting from 100 nM, 0.1 μg/mlCD86 and 10 μg/ml goat anti-human CX-conjugated acceptor beads were incubated in the AlphaPlate as described above, followed by addition of 10 μg/ml streptavidin donor beads.

7.1.3. Production Of Cell Lines Expressing Cell-Surface CD800r CD86

Genes encoding full-length human CD80 and CD86 were subcloned into appropriate mammalian expression vectors. Each plasmid containing cDNA of CD80 or CD86 was transfected into CHO-K1 (ATCC) cells by Lipofectamine 2000 (Invitrogen) and selected for stable transfection in F12K media (45% DMEM, 45% F12K, 10% FBS) containing 0.5 mg/ml G418. The 1% of single clones with the highest expression of CD80 or CD86 on the cell surface were sorted by FACS and cultured to establish stable cell lines. The expression levels between two cell lines were confirmed to be roughly equivalent to each other.

7.1.4. Potency Of CTLA4-Ig Variants In The Inhibition Of IL-2 Production Of Jurkat T Cells Jurkat cells ($3.0\times10^5$/well) and CHO-K1 that stably expressed CD80 or CD86 ($1.0\times10^4$/well) were incubated in the presence of 10 μg/ml PHA-P with titrating amounts of abatacept or CTLA4 proteins of the disclosure. After 24 hours, supernatants were assayed using an AlphaLISA® Human IL-2 kit to measure the amount of secreted IL-2.

7.2. Results

A total of 27 high affinity variants and 4 neutral affinity variants for binding of either CD80 or CD86 were confirmed by AlphaLISA®. The CTLA4-Ig variant having the mutation K28H showed the highest affinity among 19 high affinity CTLA4-Ig variants for CD80, with a binding affinity that was 11.9-fold greater than the binding affinity of wild-type CTLA4-Ig for CD80 (FIG. 2A). The CTLA4-Ig variant having the mutation A29H showed the highest affinity among 18 high affinity CTLA4-Ig variants for CD86, with a binding affinity that was 14.2-fold greater than the binding affinity of wild-type CTLA4-Ig for CD86 (FIG. 2A).

Figure 3:
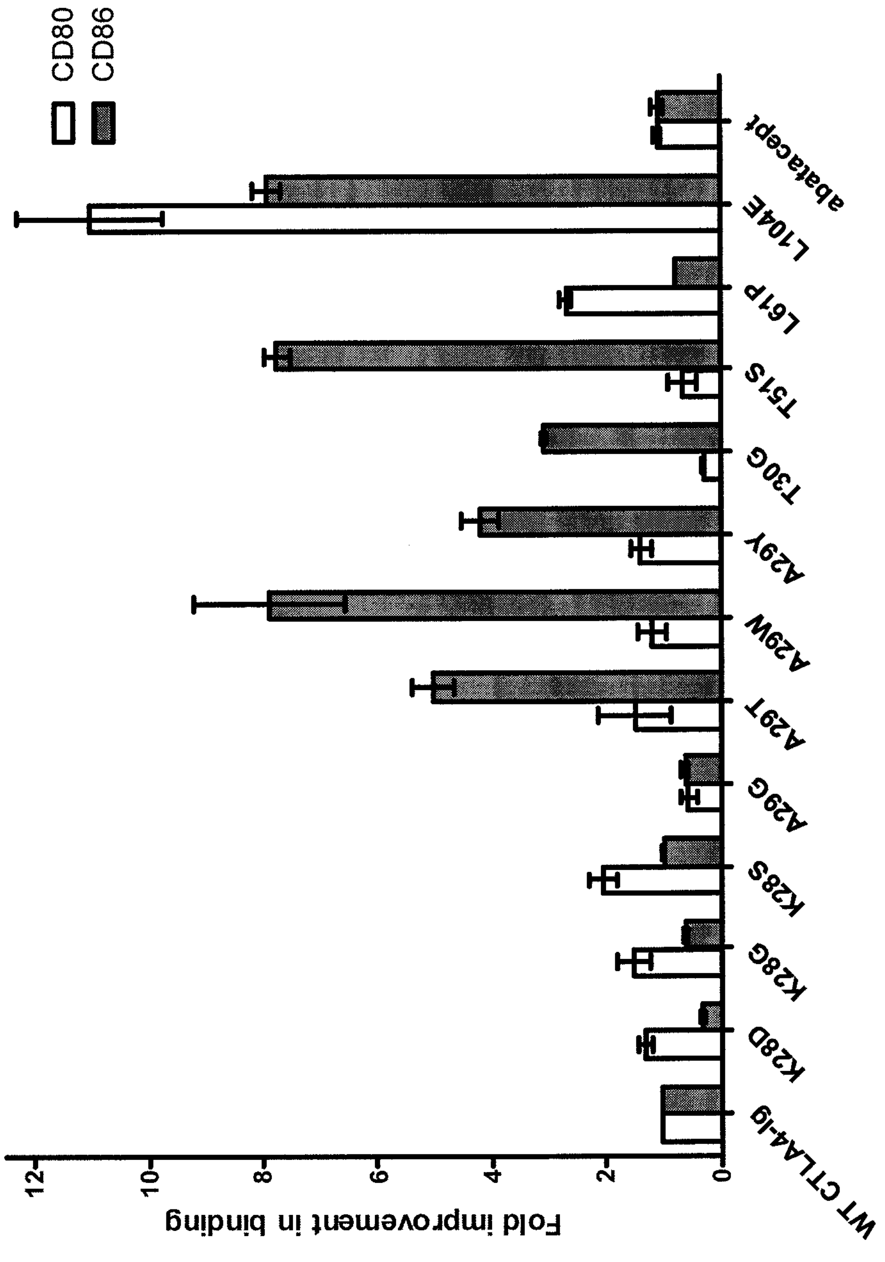

The mutations A29Y and L104E are those incorporated into belatacept (LEA29, Bristol-Myers Squibb) and were re-identified as high affinity variants in the present analysis (FIG. 3). Belatacept showed 22-fold and 32-fold improvement over wild-type CTLA4-Ig in binding to CD80 and CD86, respectively, in the AlphaLISA® assay (data not shown).

Figure 4A:
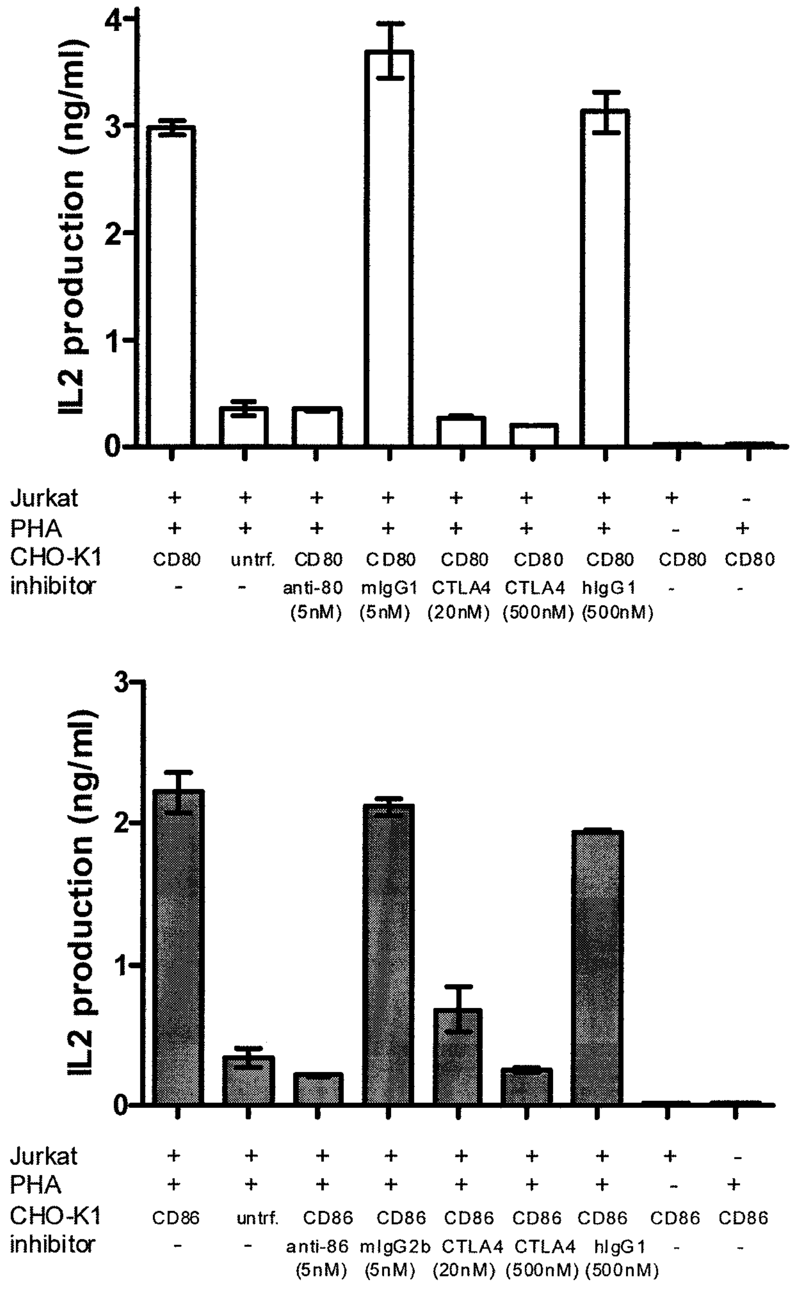

In a typical 24 hour assay without blocking agent, 2.1-3.5 ng/ml of IL-2 was produced in the culture supernatant of Jurkat T-cells stimulated by PMA and CHO-K1 cells stably expressing CD80 or CD86. In the presence of blocking agents such as CTLA4-Ig proteins or anti-CD80 or anti-CD86 antibodies, the production of IL-2 was inhibited through blocking of the costimulatory signal. No IL-2 was produced by Jurkat cells in the absence of PHA-P or CHO-K1 negative for CD80 or CD86 expression. Similarly, no IL-2 was detected in the culture supernatant of CHO-K1 cultured in the absence of Jurkat cells (FIG. 4A).

Figure 4B:
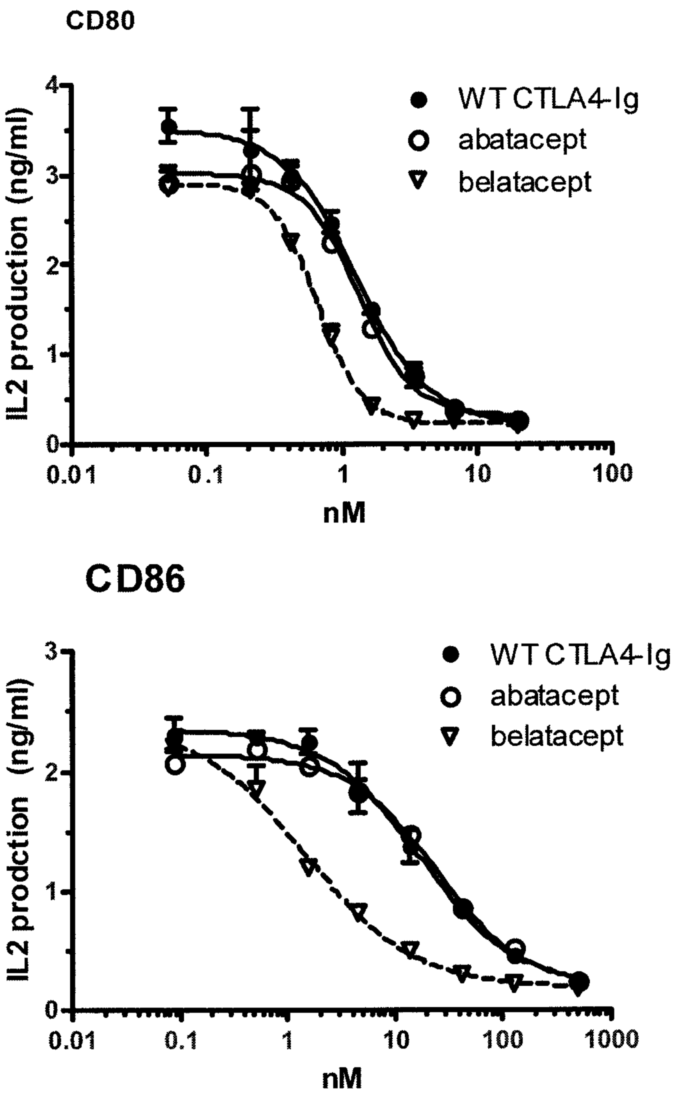

Inhibition curves of wild-type CTLA4-Ig and abatacept were found to overlap substantially when Jurkat T-cells were stimulated by PMA and CHO-K1 cells expressing either CD80 or CD86 (FIG. 4B). This result indicates that wild-type CTLA4-Ig and abatacept inhibit IL-2 production by Jurkat cells to the same extent (i.e., have similar potency). The average $IC_{50}$ value of wild-type CTLA4-Ig was determined to be 1.2 nM and 17.2 nM for CD80 and CD86, respectively. Although the two amino acid mutations in belatacept as compared to wild-type CTLA4-Ig resulted in a 22-fold improvement in binding toward CD80, belatacept showed only a 2.0-fold improvement in potency for inhibition of CD80-mediated T-cell activation over wild-type CTLA4-Ig or abatacept. In contrast, the resulting 32-fold improvement in binding of CD86 in belatacept produced an 11.5-fold improvement in potency for inhibition of CD86-mediated T-cell activation.

The 7.2-fold to 11.9-fold improvement in affinity toward CD80 of the CTLA4 variants of disclosure resulted in from 1.1-fold to 2.2-fold improvement in potency for inhibition of CD80-mediated T-cell activation. In contrast, the 7.0-fold to 14.2-fold improvement in affinity toward CD86 of the CTLA4 variants of the disclosure resulted in from 2.4-fold to 6.2-fold improvement in potency for inhibition of CD86-mediated T-cell activation. The K28H and A29H CTLA4-Ig variants respectively showed the highest affinity for CD80 and CD86 as well as the highest potency for inhibition of T-cell activation. Accordingly, a mutation that confers higher affinity binding to a ligand typically results in improved potency in inhibition of T-cell activation. Likewise, a variant with neutral affinity resulted in no significant difference in biological activity (Y52F).

Figure 4C:
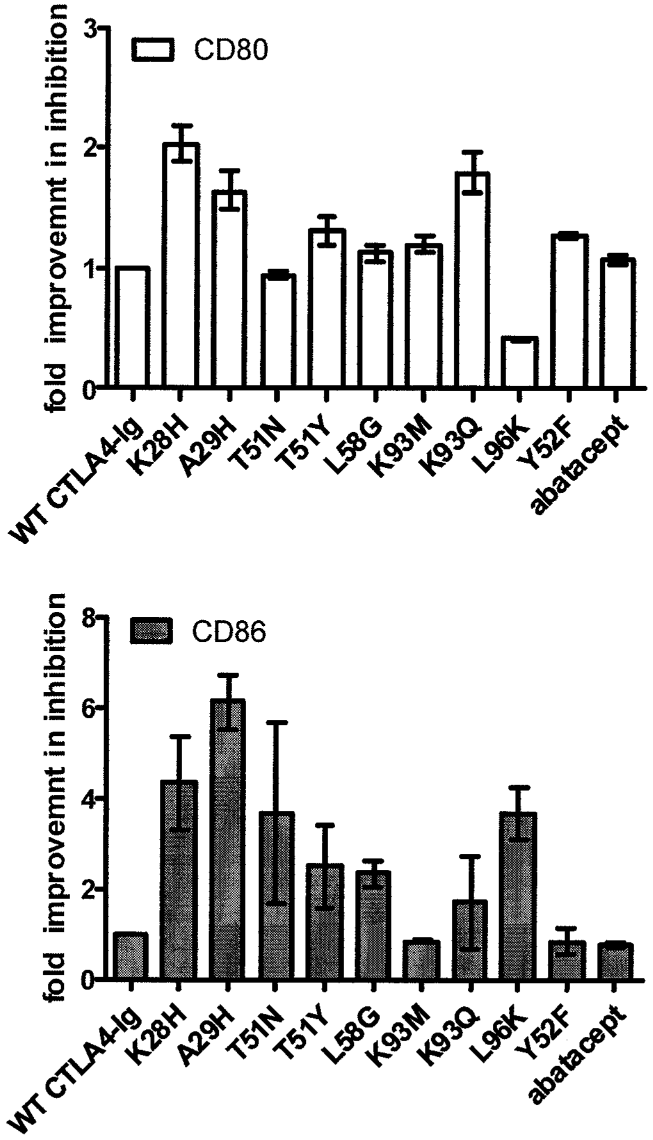
Figure 5A:
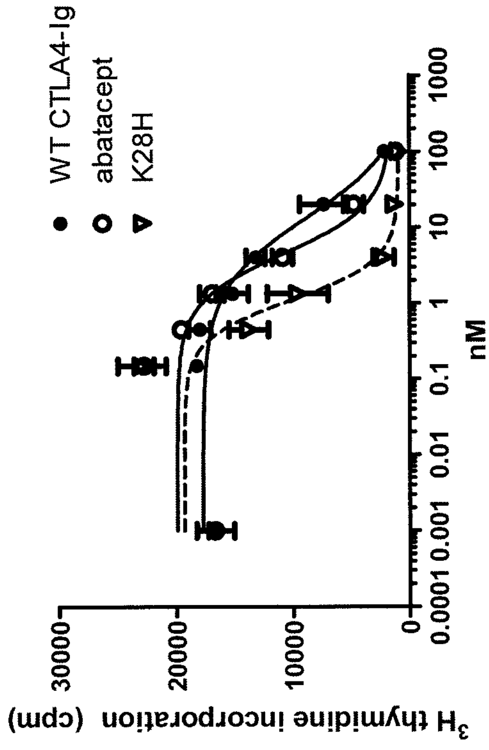
Figure 5B:
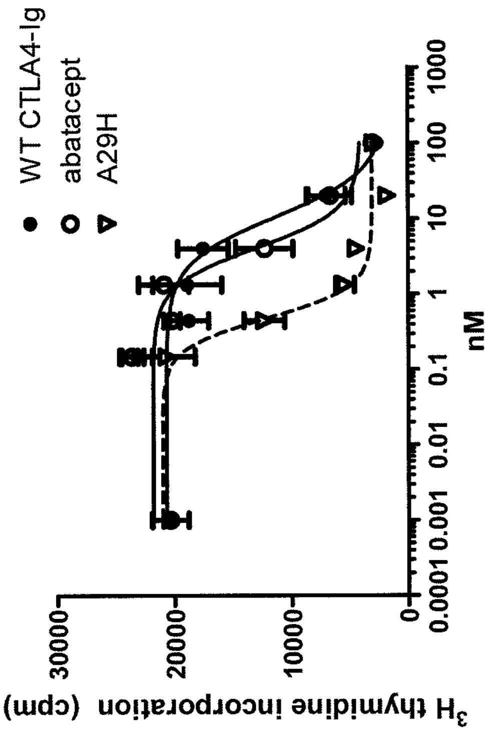
Figure 5C:
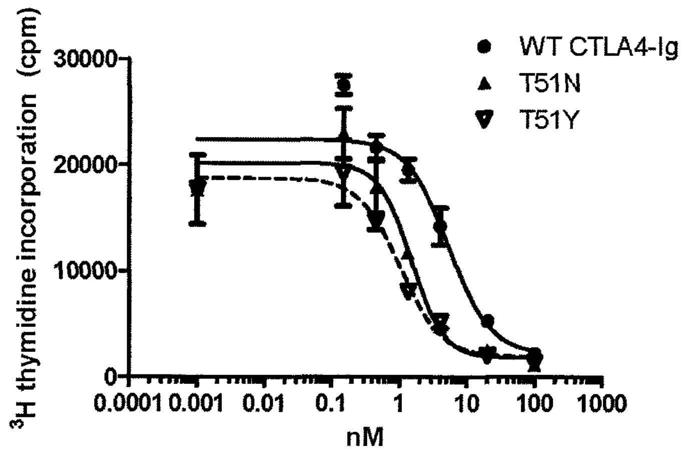
Figure 5D:
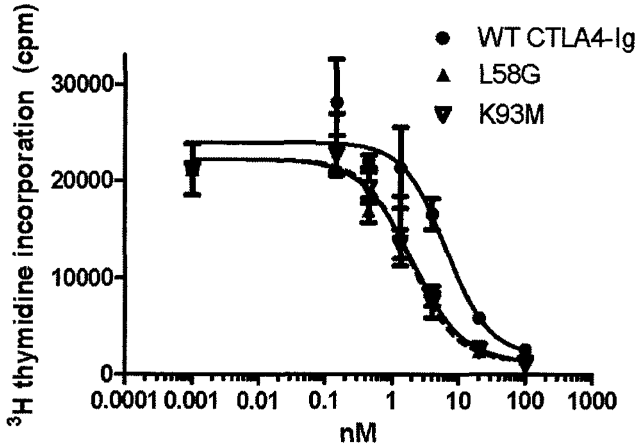
Figure 5E:
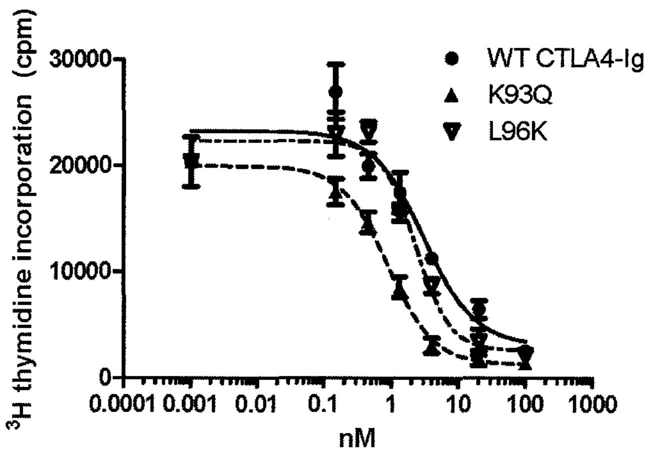
Figure 6A:
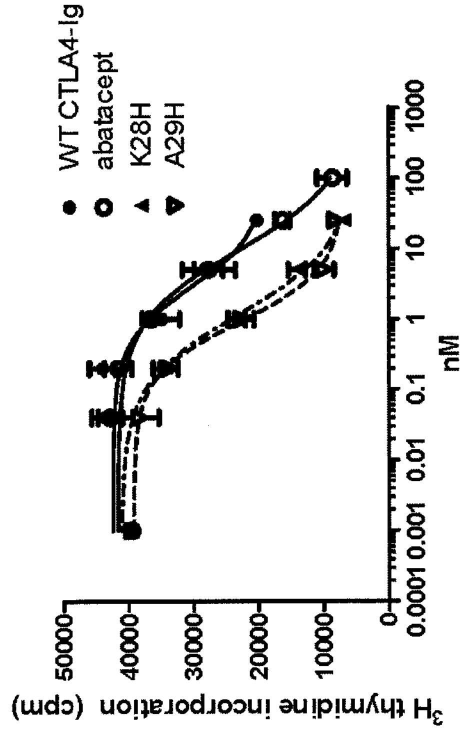
Figure 6B:
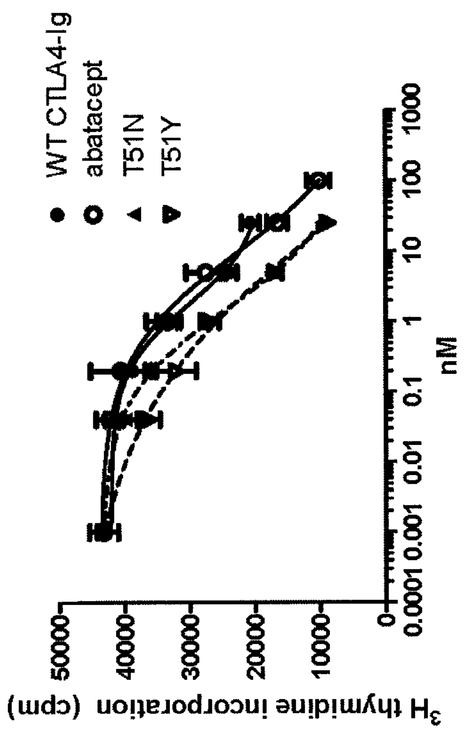
Figure 6C:
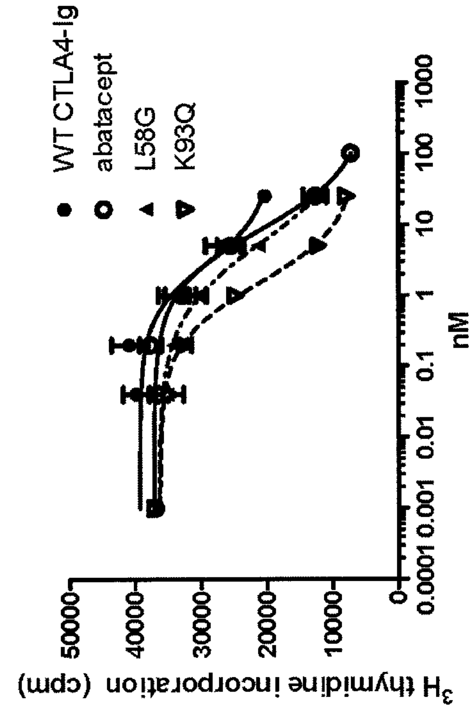
Figure 6D:
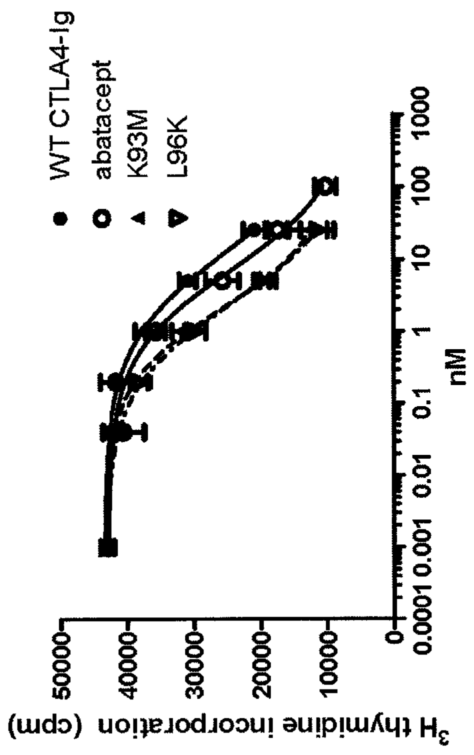

These results indicate that variants having higher binding affinity for CD86 as compared to wild-type protein show better potency as compared to variants having higher binding affinity for CD80, which is similar to the results obtained for belatacept. This can be explained by the avidity effect, which has a greater impact on biological activity when the base-line binding affinity is lower. The binding affinity of wild-type CTLA4-Ig to CD80 is likely to be too high to gain further improvement through avidity. In contrast, wild-type CTLA4-Ig has a 13-fold lower affinity for CD86 than for CD80 (Collins et al, 2002, Immunity 17: 201-210), which means that the affinity of CTLA4-Ig variants for CD86 can be improved. The avidity effect can be seen in the results obtained with the CTLA4-Ig variant having the mutation L96K (FIG. 4C). Although this variant showed significant reduction in CD80 binding affinity (10-fold lower as compared to wild-type CTLA4-Ig), the potency of this variant was only 2.4-fold lower than that of wild-type CTLA4-Ig due to the increased impact of avidity on biological activity of this low affinity variant.

8. EXAMPLE 2

Evaluation of Potency of CTLA4-Ig Variants to Inhibit T-Cell Proliferation 8.1. Materials and Methods: Potency of CTLA4-Ig Variants for Inhibiting T-cell Proliferative Responses In Vitro The human diffuse large B cell lymphoma cell line SU-DHL-6 (ATCC CRL-2959) expresses both CD80 and CD86 on the cell surface. SU-DHL-6 cells were maintained in RPMI 1640 containing 10% FBS. Peripheral blood mononuclear cells (PBMC) were isolated from human whole blood or buffy coat by Ficoll-Paque Plus (GE Healthcare, Piscataway, N.J.) density gradient centrifugation as described in the instruction manual of Leucosep Greiner Bio-One, Germany). Human peripheral $CD4^+$ T cells were isolated from PBMC using EasySep Negative Selection Human $CD4^+$ T cell Enrichment Kit (STEMCELL Technologies, Canada). T-cells were cultured in RPMI 1640 medium containing 10% heat-inactivated FBS, β-mercaptoethanol and 100 U/ml Penicillin-Streptomycin. The resulting culture contained $CD4^+$ above 90% in purity.

To set up the assays, varying concentrations of CTLA4-Ig or its variants diluted in 50 μL of media were added to each well of round-bottom 96-well microtiter plates in triplicate. $CD4^+$ T cells ($1\times10^5$) were then mixed with freshly irradiated (10,000 rad) B lymphoma cell line ($2\times10^4$) in a 5:1 responder-stimulator ratio in 150 μL of culture media. The cells were added to CTLA4-Ig or variant-containing wells resulting in a final volume of 200 μL per well. The primary allogenic stimulation assays were incubated at 37° C. in 5% $CO_2$ for 5 days. tritiated thymidine at 0.5 μCi/well were added for additional 18 hr of culture. Cells were harvested with a cell harvester (Filtermate Omnifilter-96 Harvester, Perkin Elmer) using the manufacturer's recommended conditions and [$^3$H] thymidine incorporation was measured using a scintillation counter (Wallac Trilux). For secondary allogenic stimulation assays, 6-day primary allo-stimulated T cells were harvested, isolated by Ficoll-Paque Plus density gradient centrifugation and rested in complete medium for 24 hr. T cells were then restimulated for 3 days with freshly irradiated B lymphoma cells at the same ratio as above in the presence of CTLA4-Ig and its mutants. The secondary stimulation assays were incubated at 37° C. for 2 days before addition of 0.5 μCi/well of [$^3$H]-thymidine for the final 18 hr of culture. Cell harvesting was performed as indicated above. Cell proliferation data are analyzed with GraphPad Prism 5 software using a non-linear regression curve fit method.

To evaluate the potency of CTLA4-Ig variants for inhibiting alloantigen-stimulated T-cell proliferation, purified $CD4^+$ T-cells were stimulated with an allogenic B-cell line, SU-DHL-6, positive for both CD80 and CD86 (confirmed by FACS, data not shown) Inhibition curves of wild-type CTLA4-Ig and commercial abatacept closely overlap each other, indicating equivalent potency in inhibition of proliferative response in $CD4^+$ T-cells. All variants with improved binding to CD80 and/or CD86 showed greater inhibition of proliferative responses of $CD4^+$ T-cells in both primary and secondary responses. Improvement in $IC_{50}$ was observed in a range of 1.5 to 20-fold and 1.5 to 10-fold for primary and secondary responses, respectively (FIGS. 5 and 6). Overall, affinity improvement to CD80 and/or CD86 inhibits primary proliferative responses of $CD4^+$ T-cells greater than secondary responses, reflecting the reduced dependency of memory T-cells on costimulatory molecules for secondary responses (Croft et al., 1997, Crit. Rev. Immunol. 17: 89).

Among the eight variants tested, the A29H mutation resulted in the maximum potency for inhibition of both primary and secondary proliferative responses, approximately 20-fold and 10-fold, respectively. The K28H mutation was the second best in potency with approximately 12-fold and 8-fold improvement in inhibiting primary and secondary responses, respectively (FIGS. 5 and 6 The A29H mutation showed a 14-fold improvement in binding activity toward CD86, but only a 3.0-fold improvement in binding to CD80. On the other hand, the K28H mutant showed more balanced improvement to both ligands, being 12-fold and 9.5-fold for CD80 and CD86, respectively (FIG. 2A). Since the A29H mutation resulted in the best improvement in inhibition of both primary and secondary proliferative response, increased affinity for in CD86 may have more impact on potency, assuming that the binding kinetics and protein stability of the A29H and K28H mutations are equivalent.

The L96K mutation resulted in ~11-fold reduction in CD80 binding while improving CD86-binding for ~11-fold. Another example of higher CD86 binding with reduced binding toward CD80 is T51N (10-fold to CD86 and 0.25-fold to CD80). Because both variants did not show reduction in potency in inhibiting primary or secondary responses, loss of binding toward CD80 at least up to 11-fold seems to be well compensated by the improved binding to CD86. Another possible explanation is that, since CD80 is known to form dimers (Ikemuzu et al., 2000, Immunity 12:51), loss of affinity of at least up to 11-fold may have minimal impact on the avidity provided by CD80.

In conclusion, higher affinity to either ligand results in improved potency in inhibition of proliferative response in alloantigenic stimulation, consistent with the results from 24 hr assay using Jurkat and CHO cell lines expressing CD80 or CD86 (FIG. 4). Both CD80 and CD86 can contribute to primary and secondary allo-responses, however, it is possible to contribute at different levels under the condition where differential levels of ligand expression and other costimulatory/adhesion molecules are involved.

9. Specific Embodiments, Citation Of References

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A pharmaceutical composition suitable for administration to a human patient comprising a therapeutically effective amount of a variant CTLA4 polypeptide or a polypeptide-drug conjugate comprising said variant CTLA4 polypeptide and a pharmaceutically acceptable carrier, wherein said variant CTLA4 polypeptide comprises an amino acid sequence having at least 90% sequence identity to amino acids 21 to 112 of SEQ ID NO:1 and comprises the amino acid substitution A29H as compared to a polypeptide of sequence SEQ ID NO:1.

2. The pharmaceutical composition of claim 1, wherein the variant CTLA4 polypeptide comprises one or more of the amino acid substitutions selected from K28H, K28T, T51N, T51Y, L58G, K93M, and L96K as compared to a polypeptide of sequence SEQ ID NO:1.

3. The pharmaceutical composition of claim 2 wherein the variant CTLA4 polypeptide comprises the amino acid substitution K28H.

4. The pharmaceutical composition of claim 3 where the variant CTLA4 polypeptide comprises the amino acid substitution K93Q as compared to a polypeptide of SEQ ID NO:1.

5. The pharmaceutical composition of claim 3 where the variant CTLA4 polypeptide comprises the amino acid substitution L61H as compared to a polypeptide of SEQ ID NO:1.

6. The pharmaceutical composition of claim 2 where the variant CTLA4 polypeptide comprises the amino acid substitution K28T.

7. The pharmaceutical composition of claim 6 where the variant CTLA4 polypeptide comprises the amino acid substitution L61A as compared to a polypeptide of SEQ ID NO:1.

8. The pharmaceutical composition of claim 7 where the variant CTLA4 polypeptide comprises the amino acid substitution K93Q as compared to a polypeptide of SEQ ID NO:1.

9. The pharmaceutical composition of claim 1, wherein the variant CTLA4 polypeptide comprises one or more of the amino acid substitutions selected from M53F, M54W, M54Y, L58A, L58N, L58Q, L61A, L61H, L61Y, K93I, K93V, L96R, L104H, L104M, and L104Y as compared to a polypeptide of sequence SEQ ID NO:1.

10. The pharmaceutical composition of claim 1, wherein the variant CTLA4 polypeptide comprises the amino acid substitution L104E as compared to a polypeptide of sequence SEQ ID NO:1.

11. The pharmaceutical composition of claim 1, wherein the variant CTLA4 polypeptide comprises an amino acid sequence having at least 95% sequence identity to amino acids 21 to 112 of SEQ ID NO:1.

12. The pharmaceutical composition of claim 1, wherein the variant CTLA4 polypeptide comprises an amino acid sequence having at least 97% sequence identity to amino acids 21 to 112 of SEQ ID NO:1.

13. The pharmaceutical composition of claim 1, wherein the variant CTLA4 polypeptide comprises an amino acid sequence having up to 8 substitutions as compared to amino acids 21 to 112 of SEQ ID NO:1.

14. The pharmaceutical composition of claim 1, wherein the variant CTLA4 polypeptide comprises an amino acid sequence having up to 5 substitutions as compared to amino acids 21 to 112 of SEQ ID NO:1.

15. The pharmaceutical composition of claim 1, wherein the variant CTLA4 polypeptide is a fusion protein.

16. The pharmaceutical composition of claim 15, wherein the fusion protein comprises an amino acid sequence having at least 90% sequence identity to amino acids 1 to 124 of SEQ ID NO:1 operably linked to an immunoglobulin constant region and optionally a signal sequence.

17. The pharmaceutical composition of claim 16, wherein the amino acid sequence having at least 90% sequence identity to amino acids 1 to 124 of SEQ ID NO:1 and the immunoglobulin constant region are linked by way of a hinge region in the immunoglobulin.

18. The pharmaceutical composition of claim 16, wherein the immunoglobulin constant region is an IgG1.

19. The pharmaceutical composition of claim 1, in which the CTLA4 variant polypeptide is not conjugated to a drug.

20. The pharmaceutical composition of claim 1, which comprises said polypeptide-drug conjugate.

21. A variant CTLA4 polypeptide comprising an amino acid sequence having at least 90% sequence identity to amino acids 21 to 112 of SEQ ID NO:1, wherein the variant polypeptide comprises the amino acid substitution A29H and one or more of the amino acid substitutions K28H, K28T and L96K as compared to the polypeptide of SEQ ID NO:1.

22. The variant CTLA4 polypeptide of claim 21, which comprises the amino acid substitution K28H as compared to a polypeptide of sequence SEQ ID NO:1.

23. The variant CTLA4 polypeptide of claim 22, which comprises the amino acid substitution K93Q as compared to a polypeptide of sequence SEQ ID NO:1.

24. The variant CTLA4 polypeptide of claim 21, which comprises the amino acid substitution K28T as compared to a polypeptide of sequence SEQ ID NO:1.

25. The variant CTLA4 polypeptide of claim 24, which comprises the amino acid substitution K93Q as compared to a polypeptide of sequence SEQ ID NO:1.

26. The variant CTLA4 polypeptide of claim 21, which comprises the amino acid substitution L96K as compared to a polypeptide of sequence SEQ ID NO:1.

27. The variant CTLA4 polypeptide of claim 26, which comprises the amino acid substitution K93Q as compared to a polypeptide of sequence SEQ ID NO:1.

28. The variant CTLA4 polypeptide of claim 21, which comprises the amino acid substitution L104E as compared to a polypeptide of SEQ ID NO:1.

29. The variant CTLA4 polypeptide of claim 21, which comprises the amino acid substitution L61H as compared to a polypeptide of SEQ ID NO:1.

30. The variant CTLA4 polypeptide of claim 21, which comprises the amino acid substitution L61A as compared to a polypeptide of SEQ ID NO:1.

31. The variant CTLA4 polypeptide of claim 22, which comprises the amino acid substitution L61H as compared to a polypeptide of SEQ ID NO:1.

32. The variant CTLA4 polypeptide of claim 22, which comprises the amino acid substitution L61A as compared to a polypeptide of SEQ ID NO:1.

33. The variant polypeptide of claim 21, which comprises an amino acid sequence having at least 95% sequence identity to amino acids 21 to 112 of SEQ ID NO:1.

34. The variant CTLA4 polypeptide of claim 21, which comprises an amino acid sequence having up to 8 substitutions as compared to amino acids 21 to 112 of SEQ ID NO:1.

35. The variant CTLA4 polypeptide of claim 21, which comprises an amino acid sequence having up to 5 substitutions as compared to amino acids 21 to 112 of SEQ ID NO:1.

36. The variant CTLA4 polypeptide of claim 21 which is a fusion protein.

37. The variant CTLA4 polypeptide of claim 36, wherein the fusion protein comprises an amino acid sequence having at least 90% sequence identity to amino acids 1 to 124 of SEQ ID NO:1 operably linked to an immunoglobulin constant region and optionally a signal sequence.

38. The variant CTLA4 polypeptide of claim 37, wherein the amino acid sequence having at least 90% sequence identity to amino acids 1 to 124 of SEQ ID NO:1 and the immunoglobulin constant region are linked by way of a hinge region in the immunoglobulin.

39. The CTLA4 protein of claim 38, wherein the immunoglobulin constant region is an IgG 1.

40. A polypeptide-drug conjugate comprising a variant CTLA4 polypeptide according to claim 21.

41. A method of treating an autoimmune disease comprising administering to a human in need thereof a therapeutically effective amount of a pharmaceutical composition according to claim 1, a CTLA4 polypeptide according to claim 21, or a CTLA4 polypeptide-drug conjugate according to claim 40.

42. The pharmaceutical composition of claim 2, wherein the variant CTLA4 polypeptide further comprises the amino acid substitution T51N.

43. The pharmaceutical composition of claim 1, wherein said therapeutically effective amount is suitable for treatment of an autoimmune disease.

* * * * *

SEQUENCE LISTING

```
<160> NUMBER OF SEQ ID NOS: 761

<210> SEQ ID NO 1
<211> LENGTH: 124
<212> TYPE: PRT
<213> ORGANISM: Homo sapiens

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
```

-continued

```
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 2
<211> LENGTH: 8
<212> TYPE: PRT
<213> ORGANISM: Homo sapiens

<400> SEQUENCE: 2

Pro Gly Lys Ala Thr Glu Val Arg
1               5


<210> SEQ ID NO 3
<211> LENGTH: 13
<212> TYPE: PRT
<213> ORGANISM: Homo sapiens

<400> SEQUENCE: 3

Thr Tyr Met Met Gly Asn Glu Leu Thr Phe Leu Asp Asp
1               5                   10


<210> SEQ ID NO 4
<211> LENGTH: 12
<212> TYPE: PRT
<213> ORGANISM: Homo sapiens

<400> SEQUENCE: 4

Lys Val Glu Leu Met Tyr Pro Pro Pro Tyr Tyr Leu
1               5                   10


<210> SEQ ID NO 5
<211> LENGTH: 186
<212> TYPE: PRT
<213> ORGANISM: Homo sapiens

<400> SEQUENCE: 5

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
```

```
            100                 105                 110

Tyr Val Ile Asp Pro Glu Pro Cys Pro Asp Ser Asp Phe Leu Leu Trp
        115                 120                 125

Ile Leu Ala Ala Val Ser Ser Gly Leu Phe Phe Tyr Ser Phe Leu Leu
    130                 135                 140

Thr Ala Val Ser Leu Ser Lys Met Leu Lys Lys Arg Ser Pro Leu Thr
145                 150                 155                 160

Thr Gly Val Tyr Val Lys Met Pro Pro Thr Glu Pro Glu Cys Glu Lys
                165                 170                 175

Gln Phe Gln Pro Tyr Phe Ile Pro Ile Asn
            180                 185


<210> SEQ ID NO 6
<211> LENGTH: 357
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
```

```
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355


<210> SEQ ID NO 7
<211> LENGTH: 233
<212> TYPE: PRT
<213> ORGANISM: Homo sapiens

<400> SEQUENCE: 7

Val Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230


<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8
```

Pro Gly His Ala Thr Glu Val Arg
1 5

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Pro Gly Thr Ala Thr Glu Val Arg
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Pro Gly Lys His Thr Glu Val Arg
1 5

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Tyr Tyr Met Met Gly Asn Glu Leu Thr Phe Leu Asp Asp
1 5 10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Thr Tyr Phe Met Gly Asn Glu Leu Thr Phe Leu Asp Asp
1 5 10

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Thr Tyr Tyr Met Gly Asn Glu Leu Thr Phe Leu Asp Asp
1 5 10

<210> SEQ ID NO 14
<211> LENGTH: 13
<212> TYPE: PRT
<213> ORGANISM: Artificial Sequence
<220> FEATURE:

<223> OTHER INFORMATION: Description of Artificial Sequence: Synthetic peptide

<400> SEQUENCE: 14

Thr Tyr Met Met Gly Asn Glu Gly Thr Phe Leu Asp Asp
1 5 10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Thr Tyr Met Met Gly Asn Glu Leu Thr Phe His Asp Asp
1 5 10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Thr Tyr Met Met Gly Asn Glu Leu Thr Phe Tyr Asp Asp
1 5 10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Met Val Glu Leu Met Tyr Pro Pro Pro Tyr Tyr Leu
1 5 10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gln Val Glu Leu Met Tyr Pro Pro Pro Tyr Tyr Leu
1 5 10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Thr Tyr Met Met Gly Asn Glu Ala Thr Phe Leu Asp Asp
1 5 10

<210> SEQ ID NO 20

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Tyr Met Met Gly Asn Glu Asn Thr Phe Leu Asp Asp
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Tyr Met Met Gly Asn Glu Gln Thr Phe Leu Asp Asp
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Tyr Met Met Gly Asn Glu Leu Thr Phe Ala Asp Asp
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Val Val Glu Leu Met Tyr Pro Pro Pro Tyr Tyr Leu
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Lys Val Glu Leu Met Tyr Pro Pro Pro Tyr Tyr His
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Val Glu Leu Met Tyr Pro Pro Pro Tyr Tyr Tyr

-continued 1 5 10

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Pro Gly Lys Ala Glu Glu Val Arg
1 5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Thr Tyr Met Arg Gly Asn Glu Leu Thr Phe Leu Asp Asp
1 5 10

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Thr Tyr Met Met Pro Asn Glu Leu Thr Phe Leu Asp Asp
1 5 10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Thr Tyr Met Met Gly Asn Pro Leu Thr Phe Leu Asp Asp
1 5 10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Thr Tyr Met Met Gly Asn Glu Glu Thr Phe Leu Asp Asp
1 5 10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 31

Thr Tyr Met Met Gly Asn Glu Pro Thr Phe Leu Asp Asp
1 5 10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Thr Tyr Met Met Gly Asn Glu Tyr Thr Phe Leu Asp Asp
1 5 10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Thr Tyr Met Met Gly Asn Glu Leu Thr Phe Phe Asp Asp
1 5 10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Lys Val Glu Leu Met Tyr Pro Pro Pro Tyr Tyr Ile
1 5 10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Ile Val Glu Leu Met Tyr Pro Pro Pro Tyr Tyr Leu
1 5 10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Thr Tyr Met Met Gly Asn Glu His Thr Phe Leu Asp Asp
1 5 10

<210> SEQ ID NO 37
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 37

Thr Tyr Met Met Gly Asn Glu Lys Thr Phe Leu Asp Asp
1 5 10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Thr Tyr Met Met Gly Asn Glu Leu Thr Phe Leu His Asp
1 5 10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 39

Thr Tyr Met Trp Gly Asn Glu Leu Thr Phe Leu Asp Asp
1 5 10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 40

Thr Tyr Met Tyr Gly Asn Glu Leu Thr Phe Leu Asp Asp
1 5 10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 41

Pro Gly Lys Ala Thr Glu Val Asp
1 5

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Thr Tyr Met Met Gly Asn Glu Leu Thr Phe Trp Asp Asp
1 5 10

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 43

Pro Gly Lys Lys Thr Glu Val Arg
1 5

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 44

Asn Tyr Met Met Gly Asn Glu Leu Thr Phe Leu Asp Asp
1 5 10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 45

Thr Tyr Trp Met Gly Asn Glu Leu Thr Phe Leu Asp Asp
1 5 10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 46

Lys Val Glu Lys Met Tyr Pro Pro Pro Tyr Tyr Leu
1 5 10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 47

Lys Val Glu Arg Met Tyr Pro Pro Pro Tyr Tyr Leu
1 5 10

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 48

Pro Ala Lys Ala Thr Glu Val Arg
1 5

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 49

Thr Phe Met Met Gly Asn Glu Leu Thr Phe Leu Asp Asp
1 5 10

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 50

Thr Tyr Met Met Gly Thr Glu Leu Thr Phe Leu Asp Asp
1 5 10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 51

Lys Val Glu Leu Met Tyr Pro Pro Pro Tyr Tyr Met
1 5 10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Ile Gly Lys Ala Thr Glu Val Arg
1 5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Leu Gly Lys Ala Thr Glu Val Arg
1 5

<210> SEQ ID NO 54
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 54

Met Gly Lys Ala Thr Glu Val Arg
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gln Gly Lys Ala Thr Glu Val Arg
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Thr Gly Lys Ala Thr Glu Val Arg
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Val Gly Lys Ala Thr Glu Val Arg
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Pro Gly Arg Ala Thr Glu Val Arg
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Gly Lys Pro Thr Glu Val Arg
1               5

<210> SEQ ID NO 60

-continued

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Pro Gly Lys Ser Thr Glu Val Arg
1 5

<210> SEQ ID NO 61
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Pro Gly Lys Ala His Glu Val Arg
1 5

<210> SEQ ID NO 62
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Pro Gly Lys Ala Met Glu Val Arg
1 5

<210> SEQ ID NO 63
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Pro Gly Lys Ala Ser Glu Val Arg
1 5

<210> SEQ ID NO 64
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Pro Gly Lys Ala Thr Glu Glu Arg
1 5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Pro Gly Lys Ala Thr Glu Val Pro

-continued 1 5

<210> SEQ ID NO 66
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 66

Ala Tyr Met Met Gly Asn Glu Leu Thr Phe Leu Asp Asp
1 5 10

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 67

Thr His Met Met Gly Asn Glu Leu Thr Phe Leu Asp Asp
1 5 10

<210> SEQ ID NO 68
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Thr Met Met Met Gly Asn Glu Leu Thr Phe Leu Asp Asp
1 5 10

<210> SEQ ID NO 69
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Thr Trp Met Met Gly Asn Glu Leu Thr Phe Leu Asp Asp
1 5 10

<210> SEQ ID NO 70
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Thr Tyr Asp Met Gly Asn Glu Leu Thr Phe Leu Asp Asp
1 5 10

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Thr Tyr Met Asp Gly Asn Glu Leu Thr Phe Leu Asp Asp
1 5 10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Thr Tyr Met Gly Gly Asn Glu Leu Thr Phe Leu Asp Asp
1 5 10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Thr Tyr Met His Gly Asn Glu Leu Thr Phe Leu Asp Asp
1 5 10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Thr Tyr Met Leu Gly Asn Glu Leu Thr Phe Leu Asp Asp
1 5 10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Thr Tyr Met Met Asp Asn Glu Leu Thr Phe Leu Asp Asp
1 5 10

<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Thr Tyr Met Met His Asn Glu Leu Thr Phe Leu Asp Asp
1 5 10

<210> SEQ ID NO 77
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 77

Thr Tyr Met Met Thr Asn Glu Leu Thr Phe Leu Asp Asp
1 5 10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 78

Thr Tyr Met Met Gly Ala Glu Leu Thr Phe Leu Asp Asp
1 5 10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 79

Thr Tyr Met Met Gly Phe Glu Leu Thr Phe Leu Asp Asp
1 5 10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 80

Thr Tyr Met Met Gly Gly Glu Leu Thr Phe Leu Asp Asp
1 5 10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Thr Tyr Met Met Gly His Glu Leu Thr Phe Leu Asp Asp
1 5 10

<210> SEQ ID NO 82
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Thr Tyr Met Met Gly Ile Glu Leu Thr Phe Leu Asp Asp
1 5 10

<210> SEQ ID NO 83
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Thr Tyr Met Met Gly Lys Glu Leu Thr Phe Leu Asp Asp
1 5 10

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Thr Tyr Met Met Gly Leu Glu Leu Thr Phe Leu Asp Asp
1 5 10

<210> SEQ ID NO 85
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Thr Tyr Met Met Gly Met Glu Leu Thr Phe Leu Asp Asp
1 5 10

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Thr Tyr Met Met Gly Gln Glu Leu Thr Phe Leu Asp Asp
1 5 10

<210> SEQ ID NO 87
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 87

Thr Tyr Met Met Gly Arg Glu Leu Thr Phe Leu Asp Asp
1 5 10

<210> SEQ ID NO 88
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 88

Thr Tyr Met Met Gly Ser Glu Leu Thr Phe Leu Asp Asp
1 5 10

<210> SEQ ID NO 89
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 89

Thr Tyr Met Met Gly Val Glu Leu Thr Phe Leu Asp Asp
1 5 10

<210> SEQ ID NO 90
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 90

Thr Tyr Met Met Gly Tyr Glu Leu Thr Phe Leu Asp Asp
1 5 10

<210> SEQ ID NO 91
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

Thr Tyr Met Met Gly Asn Ala Leu Thr Phe Leu Asp Asp
1 5 10

<210> SEQ ID NO 92
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

Thr Tyr Met Met Gly Asn Asp Leu Thr Phe Leu Asp Asp
1 5 10

<210> SEQ ID NO 93
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

Thr Tyr Met Met Gly Asn His Leu Thr Phe Leu Asp Asp
1 5 10

<210> SEQ ID NO 94
<211> LENGTH: 13
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 94

Thr Tyr Met Met Gly Asn Lys Leu Thr Phe Leu Asp Asp
1 5 10

<210> SEQ ID NO 95
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 95

Thr Tyr Met Met Gly Asn Met Leu Thr Phe Leu Asp Asp
1 5 10

<210> SEQ ID NO 96
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 96

Thr Tyr Met Met Gly Asn Asn Leu Thr Phe Leu Asp Asp
1 5 10

<210> SEQ ID NO 97
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 97

Thr Tyr Met Met Gly Asn Gln Leu Thr Phe Leu Asp Asp
1 5 10

<210> SEQ ID NO 98
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 98

Thr Tyr Met Met Gly Asn Arg Leu Thr Phe Leu Asp Asp
1 5 10

<210> SEQ ID NO 99
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 99

Thr Tyr Met Met Gly Asn Ser Leu Thr Phe Leu Asp Asp
1 5 10

<210> SEQ ID NO 100

<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 100

Thr Tyr Met Met Gly Asn Thr Leu Thr Phe Leu Asp Asp
1 5 10

<210> SEQ ID NO 101
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 101

Thr Tyr Met Met Gly Asn Val Leu Thr Phe Leu Asp Asp
1 5 10

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 102

Thr Tyr Met Met Gly Asn Glu Ile Thr Phe Leu Asp Asp
1 5 10

<210> SEQ ID NO 103
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 103

Thr Tyr Met Met Gly Asn Glu Arg Thr Phe Leu Asp Asp
1 5 10

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 104

Thr Tyr Met Met Gly Asn Glu Thr Thr Phe Leu Asp Asp
1 5 10

<210> SEQ ID NO 105
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 105

Thr Tyr Met Met Gly Asn Glu Leu Ile Phe Leu Asp Asp

-continued 1 5 10

<210> SEQ ID NO 106
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 106

Thr Tyr Met Met Gly Asn Glu Leu Met Phe Leu Asp Asp
1 5 10

<210> SEQ ID NO 107
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 107

Thr Tyr Met Met Gly Asn Glu Leu Asn Phe Leu Asp Asp
1 5 10

<210> SEQ ID NO 108
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 108

Thr Tyr Met Met Gly Asn Glu Leu Gln Phe Leu Asp Asp
1 5 10

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

Thr Tyr Met Met Gly Asn Glu Leu Arg Phe Leu Asp Asp
1 5 10

<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 110

Thr Tyr Met Met Gly Asn Glu Leu Ser Phe Leu Asp Asp
1 5 10

<210> SEQ ID NO 111
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 111

Thr Tyr Met Met Gly Asn Glu Leu Val Phe Leu Asp Asp
1 5 10

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Thr Tyr Met Met Gly Asn Glu Leu Thr Phe Glu Asp Asp
1 5 10

<210> SEQ ID NO 113
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Thr Tyr Met Met Gly Asn Glu Leu Thr Phe Ile Asp Asp
1 5 10

<210> SEQ ID NO 114
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Thr Tyr Met Met Gly Asn Glu Leu Thr Phe Met Asp Asp
1 5 10

<210> SEQ ID NO 115
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Thr Tyr Met Met Gly Asn Glu Leu Thr Phe Thr Asp Asp
1 5 10

<210> SEQ ID NO 116
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Thr Tyr Met Met Gly Asn Glu Leu Thr Phe Val Asp Asp
1 5 10

<210> SEQ ID NO 117
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 117

Thr Tyr Met Met Gly Asn Glu Leu Thr Phe Leu Arg Asp
1 5 10

<210> SEQ ID NO 118
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 118

Thr Tyr Met Met Gly Asn Glu Leu Thr Phe Leu Asp Glu
1 5 10

<210> SEQ ID NO 119
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 119

Thr Tyr Met Met Gly Asn Glu Leu Thr Phe Leu Asp Gly
1 5 10

<210> SEQ ID NO 120
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 120

Thr Tyr Met Met Gly Asn Glu Leu Thr Phe Leu Asp His
1 5 10

<210> SEQ ID NO 121
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 121

Thr Tyr Met Met Gly Asn Glu Leu Thr Phe Leu Asp Thr
1 5 10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 122

Gly Val Glu Leu Met Tyr Pro Pro Pro Tyr Tyr Leu
1 5 10

-continued

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 123

Lys Gly Glu Leu Met Tyr Pro Pro Pro Tyr Tyr Leu
1 5 10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 124

Lys Ile Glu Leu Met Tyr Pro Pro Pro Tyr Tyr Leu
1 5 10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 125

Lys Val Trp Leu Met Tyr Pro Pro Pro Tyr Tyr Leu
1 5 10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 126

Lys Val Glu Leu Met Tyr His Pro Pro Tyr Tyr Leu
1 5 10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 127

Lys Val Glu Leu Met Tyr Thr Pro Pro Tyr Tyr Leu
1 5 10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 128

Lys Val Glu Leu Met Tyr Leu Pro Pro Tyr Tyr Leu
1 5 10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Lys Val Glu Leu Met Tyr Pro Pro Pro Thr Tyr Leu
1 5 10

<210> SEQ ID NO 130
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 130

Pro Gly Tyr Ala Thr Glu Val Arg
1 5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 131

Asn Gly Lys Ala Thr Glu Val Arg
1 5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 132

Pro Ile Lys Ala Thr Glu Val Arg
1 5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 133

Pro Gln Lys Ala Thr Glu Val Arg
1 5

<210> SEQ ID NO 134
<211> LENGTH: 8
<212> TYPE: PRT
<213> ORGANISM: Artificial Sequence
<220> FEATURE:

<223> OTHER INFORMATION: Description of Artificial Sequence: Synthetic peptide

<400> SEQUENCE: 134

Pro Trp Lys Ala Thr Glu Val Arg
1 5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 135

Pro Gly Glu Ala Thr Glu Val Arg
1 5

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 136

Pro Gly Ile Ala Thr Glu Val Arg
1 5

<210> SEQ ID NO 137
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 137

Pro Gly Met Ala Thr Glu Val Arg
1 5

<210> SEQ ID NO 138
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 138

Pro Gly Pro Ala Thr Glu Val Arg
1 5

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 139

Pro Gly Gln Ala Thr Glu Val Arg
1 5

<210> SEQ ID NO 140

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 140

Pro Gly Val Ala Thr Glu Val Arg
1 5

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 141

Pro Gly Lys Ala Ile Glu Val Arg
1 5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 142

Pro Gly Lys Ala Leu Glu Val Arg
1 5

<210> SEQ ID NO 143
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 143

Thr Tyr Glu Met Gly Asn Glu Leu Thr Phe Leu Asp Asp
1 5 10

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 144

Thr Tyr Leu Met Gly Asn Glu Leu Thr Phe Leu Asp Asp
1 5 10

<210> SEQ ID NO 145
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 145

Thr Tyr Asn Met Gly Asn Glu Leu Thr Phe Leu Asp Asp 1 5 10

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 146

Thr Tyr Met Ala Gly Asn Glu Leu Thr Phe Leu Asp Asp
1 5 10

<210> SEQ ID NO 147
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 147

Thr Tyr Met Gln Gly Asn Glu Leu Thr Phe Leu Asp Asp
1 5 10

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 148

Thr Tyr Met Ser Gly Asn Glu Leu Thr Phe Leu Asp Asp
1 5 10

<210> SEQ ID NO 149
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 149

Thr Tyr Met Met Gly Asn Glu Asp Thr Phe Leu Asp Asp
1 5 10

<210> SEQ ID NO 150
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 150

Thr Tyr Met Met Gly Asn Glu Val Thr Phe Leu Asp Asp
1 5 10

<210> SEQ ID NO 151
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Thr Tyr Met Met Gly Asn Glu Leu His Phe Leu Asp Asp
1 5 10

<210> SEQ ID NO 152
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Thr Tyr Met Met Gly Asn Glu Leu Lys Phe Leu Asp Asp
1 5 10

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 153

Thr Tyr Met Met Gly Asn Glu Leu Leu Phe Leu Asp Asp
1 5 10

<210> SEQ ID NO 154
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 154

Thr Tyr Met Met Gly Asn Glu Leu Pro Phe Leu Asp Asp
1 5 10

<210> SEQ ID NO 155
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 155

Thr Tyr Met Met Gly Asn Glu Leu Thr Phe Asp Asp Asp
1 5 10

<210> SEQ ID NO 156
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 156

Thr Tyr Met Met Gly Asn Glu Leu Thr Phe Gly Asp Asp
1 5 10

<210> SEQ ID NO 157
<211> LENGTH: 13
<212> TYPE: PRT

<213> ORGANISM: Artificial Sequence
<220> FEATURE:
<223> OTHER INFORMATION: Description of Artificial Sequence: Synthetic peptide

<400> SEQUENCE: 157

Thr Tyr Met Met Gly Asn Glu Leu Thr Phe Gln Asp Asp
1 5 10

<210> SEQ ID NO 158
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 158

Thr Tyr Met Met Gly Asn Glu Leu Thr Phe Arg Asp Asp
1 5 10

<210> SEQ ID NO 159
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Thr Tyr Met Met Gly Asn Glu Leu Thr Phe Leu Ala Asp
1 5 10

<210> SEQ ID NO 160
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 160

Thr Tyr Met Met Gly Asn Glu Leu Thr Phe Leu Glu Asp
1 5 10

<210> SEQ ID NO 161
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 161

Thr Tyr Met Met Gly Asn Glu Leu Thr Phe Leu Ser Asp
1 5 10

<210> SEQ ID NO 162
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 162

Thr Tyr Met Met Gly Asn Glu Leu Thr Phe Leu Asp Gln
1 5 10

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 163

Thr Tyr Met Met Gly Asn Glu Leu Thr Phe Leu Asp Ser
1 5 10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 164

Arg Val Glu Leu Met Tyr Pro Pro Pro Tyr Tyr Leu
1 5 10

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 165

Arg Gly Lys Ala Thr Glu Val Arg
1 5

<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 166

Pro Asp Lys Ala Thr Glu Val Arg
1 5

<210> SEQ ID NO 167
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 167

Pro Pro Lys Ala Thr Glu Val Arg
1 5

<210> SEQ ID NO 168
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 168

Pro Gly Lys Asn Thr Glu Val Arg
1 5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 169

Pro Gly Lys Ala Lys Glu Val Arg
1 5

<210> SEQ ID NO 170
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 170

Pro Gly Lys Ala Thr Asp Val Arg
1 5

<210> SEQ ID NO 171
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 171

Pro Gly Lys Ala Thr Gly Val Arg
1 5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 172

Pro Gly Lys Ala Thr Pro Val Arg
1 5

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 173

Pro Gly Lys Ala Thr Arg Val Arg
1 5

<210> SEQ ID NO 174
<211> LENGTH: 8
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 174

Pro Gly Lys Ala Thr Thr Val Arg
1 5

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Pro Gly Lys Ala Thr Glu Gly Arg
1 5

<210> SEQ ID NO 176
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 176

Pro Gly Lys Ala Thr Glu His Arg
1 5

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 177

Pro Gly Lys Ala Thr Glu Thr Arg
1 5

<210> SEQ ID NO 178
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 178

Pro Gly Lys Ala Thr Glu Val Glu
1 5

<210> SEQ ID NO 179
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 179

Pro Gly Lys Ala Thr Glu Val Gly
1 5

<210> SEQ ID NO 180

<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 180

Pro Gly Lys Ala Thr Glu Val Ile
1 5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 181

Pro Gly Lys Ala Thr Glu Val Met
1 5

<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 182

Pro Gly Lys Ala Thr Glu Val Asn
1 5

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 183

Pro Gly Lys Ala Thr Glu Val Gln
1 5

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 184

Pro Gly Lys Ala Thr Glu Val Trp
1 5

<210> SEQ ID NO 185
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 185

Pro Gly Lys Ala Thr Glu Val Tyr 1 5

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 186

Glu Tyr Met Met Gly Asn Glu Leu Thr Phe Leu Asp Asp
1 5 10

<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 187

Gly Tyr Met Met Gly Asn Glu Leu Thr Phe Leu Asp Asp
1 5 10

<210> SEQ ID NO 188
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 188

Ile Tyr Met Met Gly Asn Glu Leu Thr Phe Leu Asp Asp
1 5 10

<210> SEQ ID NO 189
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 189

Val Tyr Met Met Gly Asn Glu Leu Thr Phe Leu Asp Asp
1 5 10

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 190

Thr Ala Met Met Gly Asn Glu Leu Thr Phe Leu Asp Asp
1 5 10

<210> SEQ ID NO 191
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 191

Thr Asp Met Met Gly Asn Glu Leu Thr Phe Leu Asp Asp
1 5 10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 192

Thr Ile Met Met Gly Asn Glu Leu Thr Phe Leu Asp Asp
1 5 10

<210> SEQ ID NO 193
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 193

Thr Lys Met Met Gly Asn Glu Leu Thr Phe Leu Asp Asp
1 5 10

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 194

Thr Leu Met Met Gly Asn Glu Leu Thr Phe Leu Asp Asp
1 5 10

<210> SEQ ID NO 195
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 195

Thr Gln Met Met Gly Asn Glu Leu Thr Phe Leu Asp Asp
1 5 10

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 196

Thr Arg Met Met Gly Asn Glu Leu Thr Phe Leu Asp Asp
1 5 10

<210> SEQ ID NO 197
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 197

Thr Ser Met Met Gly Asn Glu Leu Thr Phe Leu Asp Asp
1 5 10

<210> SEQ ID NO 198
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 198

Thr Thr Met Met Gly Asn Glu Leu Thr Phe Leu Asp Asp
1 5 10

<210> SEQ ID NO 199
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 199

Thr Tyr His Met Gly Asn Glu Leu Thr Phe Leu Asp Asp
1 5 10

<210> SEQ ID NO 200
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 200

Thr Tyr Pro Met Gly Asn Glu Leu Thr Phe Leu Asp Asp
1 5 10

<210> SEQ ID NO 201
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 201

Thr Tyr Ser Met Gly Asn Glu Leu Thr Phe Leu Asp Asp
1 5 10

<210> SEQ ID NO 202
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 202

Thr Tyr Met Met Ala Asn Glu Leu Thr Phe Leu Asp Asp
1 5 10

<210> SEQ ID NO 203
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 203

Thr Tyr Met Met Ile Asn Glu Leu Thr Phe Leu Asp Asp
1 5 10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 204

Thr Tyr Met Met Leu Asn Glu Leu Thr Phe Leu Asp Asp
1 5 10

<210> SEQ ID NO 205
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 205

Thr Tyr Met Met Asn Asn Glu Leu Thr Phe Leu Asp Asp
1 5 10

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 206

Thr Tyr Met Met Gln Asn Glu Leu Thr Phe Leu Asp Asp
1 5 10

<210> SEQ ID NO 207
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 207

Thr Tyr Met Met Arg Asn Glu Leu Thr Phe Leu Asp Asp
1 5 10

<210> SEQ ID NO 208
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 208

Thr Tyr Met Met Tyr Asn Glu Leu Thr Phe Leu Asp Asp
1 5 10

<210> SEQ ID NO 209
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 209

Thr Tyr Met Met Gly Asn Gly Leu Thr Phe Leu Asp Asp
1 5 10

<210> SEQ ID NO 210
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 210

Thr Tyr Met Met Gly Asn Ile Leu Thr Phe Leu Asp Asp
1 5 10

<210> SEQ ID NO 211
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 211

Thr Tyr Met Met Gly Asn Trp Leu Thr Phe Leu Asp Asp
1 5 10

<210> SEQ ID NO 212
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 212

Thr Tyr Met Met Gly Asn Tyr Leu Thr Phe Leu Asp Asp
1 5 10

<210> SEQ ID NO 213
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 213

Thr Tyr Met Met Gly Asn Glu Leu Asp Phe Leu Asp Asp
1 5 10

<210> SEQ ID NO 214
<211> LENGTH: 13
<212> TYPE: PRT
<213> ORGANISM: Artificial Sequence
<220> FEATURE:

<223> OTHER INFORMATION: Description of Artificial Sequence: Synthetic peptide

<400> SEQUENCE: 214

Thr Tyr Met Met Gly Asn Glu Leu Gly Phe Leu Asp Asp
1 5 10

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 215

Thr Tyr Met Met Gly Asn Glu Leu Tyr Phe Leu Asp Asp
1 5 10

<210> SEQ ID NO 216
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 216

Thr Tyr Met Met Gly Asn Glu Leu Thr Asp Leu Asp Asp
1 5 10

<210> SEQ ID NO 217
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Thr Tyr Met Met Gly Asn Glu Leu Thr Gly Leu Asp Asp
1 5 10

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Thr Tyr Met Met Gly Asn Glu Leu Thr His Leu Asp Asp
1 5 10

<210> SEQ ID NO 219
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Thr Tyr Met Met Gly Asn Glu Leu Thr Leu Leu Asp Asp
1 5 10

<210> SEQ ID NO 220

<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Tyr Met Met Gly Asn Glu Leu Thr Phe Leu Gly Asp
1               5                   10

<210> SEQ ID NO 221
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Tyr Met Met Gly Asn Glu Leu Thr Phe Leu Ile Asp
1               5                   10

<210> SEQ ID NO 222
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Thr Tyr Met Met Gly Asn Glu Leu Thr Phe Leu Trp Asp
1               5                   10

<210> SEQ ID NO 223
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Thr Tyr Met Met Gly Asn Glu Leu Thr Phe Leu Asp Ala
1               5                   10

<210> SEQ ID NO 224
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Thr Tyr Met Met Gly Asn Glu Leu Thr Phe Leu Asp Tyr
1               5                   10

<210> SEQ ID NO 225
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Asp Val Glu Leu Met Tyr Pro Pro Pro Tyr Tyr Leu

-continued 1 5 10

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 226

His Val Glu Leu Met Tyr Pro Pro Pro Tyr Tyr Leu
1 5 10

<210> SEQ ID NO 227
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Asn Val Glu Leu Met Tyr Pro Pro Pro Tyr Tyr Leu
1 5 10

<210> SEQ ID NO 228
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 228

Pro Val Glu Leu Met Tyr Pro Pro Pro Tyr Tyr Leu
1 5 10

<210> SEQ ID NO 229
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 229

Trp Val Glu Leu Met Tyr Pro Pro Pro Tyr Tyr Leu
1 5 10

<210> SEQ ID NO 230
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Lys Ala Glu Leu Met Tyr Pro Pro Pro Tyr Tyr Leu
1 5 10

<210> SEQ ID NO 231
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Lys Asp Glu Leu Met Tyr Pro Pro Pro Tyr Tyr Leu
1 5 10

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Lys His Glu Leu Met Tyr Pro Pro Pro Tyr Tyr Leu
1 5 10

<210> SEQ ID NO 233
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 233

Lys Asn Glu Leu Met Tyr Pro Pro Pro Tyr Tyr Leu
1 5 10

<210> SEQ ID NO 234
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 234

Lys Pro Glu Leu Met Tyr Pro Pro Pro Tyr Tyr Leu
1 5 10

<210> SEQ ID NO 235
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 235

Lys Arg Glu Leu Met Tyr Pro Pro Pro Tyr Tyr Leu
1 5 10

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Lys Thr Glu Leu Met Tyr Pro Pro Pro Tyr Tyr Leu
1 5 10

<210> SEQ ID NO 237
<211> LENGTH: 12
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 237

Lys Trp Glu Leu Met Tyr Pro Pro Pro Tyr Tyr Leu
1 5 10

<210> SEQ ID NO 238
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 238

Lys Val Gly Leu Met Tyr Pro Pro Pro Tyr Tyr Leu
1 5 10

<210> SEQ ID NO 239
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 239

Lys Val Ile Leu Met Tyr Pro Pro Pro Tyr Tyr Leu
1 5 10

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 240

Lys Val Lys Leu Met Tyr Pro Pro Pro Tyr Tyr Leu
1 5 10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 241

Lys Val Pro Leu Met Tyr Pro Pro Pro Tyr Tyr Leu
1 5 10

<210> SEQ ID NO 242
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 242

Lys Val Gln Leu Met Tyr Pro Pro Pro Tyr Tyr Leu
1 5 10

<210> SEQ ID NO 243
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 243

Lys Val Arg Leu Met Tyr Pro Pro Pro Tyr Tyr Leu
1 5 10

<210> SEQ ID NO 244
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 244

Lys Val Ser Leu Met Tyr Pro Pro Pro Tyr Tyr Leu
1 5 10

<210> SEQ ID NO 245
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 245

Lys Val Thr Leu Met Tyr Pro Pro Pro Tyr Tyr Leu
1 5 10

<210> SEQ ID NO 246
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 246

Lys Val Val Leu Met Tyr Pro Pro Pro Tyr Tyr Leu
1 5 10

<210> SEQ ID NO 247
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 247

Lys Val Tyr Leu Met Tyr Pro Pro Pro Tyr Tyr Leu
1 5 10

<210> SEQ ID NO 248
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 248

Lys Val Glu Ala Met Tyr Pro Pro Pro Tyr Tyr Leu
1 5 10

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Lys Val Glu Gly Met Tyr Pro Pro Pro Tyr Tyr Leu
1 5 10

<210> SEQ ID NO 250
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 250

Lys Val Glu His Met Tyr Pro Pro Pro Tyr Tyr Leu
1 5 10

<210> SEQ ID NO 251
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

Lys Val Glu Met Met Tyr Pro Pro Pro Tyr Tyr Leu
1 5 10

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 252

Lys Val Glu Pro Met Tyr Pro Pro Pro Tyr Tyr Leu
1 5 10

<210> SEQ ID NO 253
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 253

Lys Val Glu Gln Met Tyr Pro Pro Pro Tyr Tyr Leu
1 5 10

<210> SEQ ID NO 254
<211> LENGTH: 12
<212> TYPE: PRT
<213> ORGANISM: Artificial Sequence
<220> FEATURE:

<223> OTHER INFORMATION: Description of Artificial Sequence: Synthetic peptide

<400> SEQUENCE: 254

Lys Val Glu Leu Asp Tyr Pro Pro Pro Tyr Tyr Leu
1 5 10

<210> SEQ ID NO 255
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 255

Lys Val Glu Leu Gly Tyr Pro Pro Pro Tyr Tyr Leu
1 5 10

<210> SEQ ID NO 256
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 256

Lys Val Glu Leu Ile Tyr Pro Pro Pro Tyr Tyr Leu
1 5 10

<210> SEQ ID NO 257
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Lys Val Glu Leu Asn Tyr Pro Pro Pro Tyr Tyr Leu
1 5 10

<210> SEQ ID NO 258
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 258

Lys Val Glu Leu Ser Tyr Pro Pro Pro Tyr Tyr Leu
1 5 10

<210> SEQ ID NO 259
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 259

Lys Val Glu Leu Val Tyr Pro Pro Pro Tyr Tyr Leu
1 5 10

<210> SEQ ID NO 260

-continued

<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Lys Val Glu Leu Met Tyr Ile Pro Pro Tyr Tyr Leu
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Lys Val Glu Leu Met Tyr Met Pro Pro Tyr Tyr Leu
1               5                   10

<210> SEQ ID NO 262
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Lys Val Glu Leu Met Tyr Trp Pro Pro Tyr Tyr Leu
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Val Glu Leu Met Tyr Tyr Pro Pro Tyr Tyr Leu
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Lys Val Glu Leu Met Tyr Pro His Pro Tyr Tyr Leu
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Lys Val Glu Leu Met Tyr Pro Leu Pro Tyr Tyr Leu 1 5 10

<210> SEQ ID NO 266
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 266

Lys Val Glu Leu Met Tyr Pro Thr Pro Tyr Tyr Leu
1 5 10

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 267

Lys Val Glu Leu Met Tyr Pro Val Pro Tyr Tyr Leu
1 5 10

<210> SEQ ID NO 268
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 268

Lys Val Glu Leu Met Tyr Pro Trp Pro Tyr Tyr Leu
1 5 10

<210> SEQ ID NO 269
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 269

Lys Val Glu Leu Met Tyr Pro Pro Leu Tyr Tyr Leu
1 5 10

<210> SEQ ID NO 270
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 270

Lys Val Glu Leu Met Tyr Pro Pro Pro His Tyr Leu
1 5 10

<210> SEQ ID NO 271
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 271

Lys Val Glu Leu Met Tyr Pro Pro Pro Tyr His Leu
1 5 10

<210> SEQ ID NO 272
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 272

Lys Val Glu Leu Met Tyr Pro Pro Pro Tyr Leu Leu
1 5 10

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 273

Lys Val Glu Leu Met Tyr Pro Pro Pro Tyr Pro Leu
1 5 10

<210> SEQ ID NO 274
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 274

Lys Val Glu Leu Met Tyr Pro Pro Pro Tyr Thr Leu
1 5 10

<210> SEQ ID NO 275
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 275

Lys Val Glu Leu Met Tyr Pro Pro Pro Tyr Tyr Pro
1 5 10

<210> SEQ ID NO 276
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 276

Lys Val Glu Leu Met Tyr Pro Pro Pro Tyr Tyr Glu
1 5 10

<210> SEQ ID NO 277
<211> LENGTH: 8
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 277

Pro His Lys Ala Thr Glu Val Arg
1 5

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 278

Pro Thr Lys Ala Thr Glu Val Arg
1 5

<210> SEQ ID NO 279
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 279

Pro Gly Gly Ala Thr Glu Val Arg
1 5

<210> SEQ ID NO 280
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 280

Pro Gly Asn Ala Thr Glu Val Arg
1 5

<210> SEQ ID NO 281
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 281

Pro Gly Ser Ala Thr Glu Val Arg
1 5

<210> SEQ ID NO 282
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 282

Thr Tyr Met Lys Gly Asn Glu Leu Thr Phe Leu Asp Asp
1 5 10

<210> SEQ ID NO 283
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 283

Thr Tyr Met Met Gly Asn Glu Leu Thr Phe Pro Asp Asp
1 5 10

<210> SEQ ID NO 284
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 284

Pro Ser Lys Ala Thr Glu Val Arg
1 5

<210> SEQ ID NO 285
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 285

Pro Gly Lys Thr Thr Glu Val Arg
1 5

<210> SEQ ID NO 286
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 286

Pro Gly Lys Trp Thr Glu Val Arg
1 5

<210> SEQ ID NO 287
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 287

Pro Gly Lys Tyr Thr Glu Val Arg
1 5

<210> SEQ ID NO 288
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 288

Ser Tyr Met Met Gly Asn Glu Leu Thr Phe Leu Asp Asp
1 5 10

<210> SEQ ID NO 289
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 289

Pro Gly Lys Ala Gly Glu Val Arg
1 5

<210> SEQ ID NO 290
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 290

His Gly Lys Ala Thr Glu Val Arg
1 5

<210> SEQ ID NO 291
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 291

Lys Gly Lys Ala Thr Glu Val Arg
1 5

<210> SEQ ID NO 292
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 292

Ser Gly Lys Ala Thr Glu Val Arg
1 5

<210> SEQ ID NO 293
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 293

Pro Gly Lys Gly Thr Glu Val Arg
1 5

<210> SEQ ID NO 294
<211> LENGTH: 8
<212> TYPE: PRT
<213> ORGANISM: Artificial Sequence
<220> FEATURE:

<223> OTHER INFORMATION: Description of Artificial Sequence: Synthetic peptide

<400> SEQUENCE: 294

Pro Gly Lys Val Thr Glu Val Arg
1 5

<210> SEQ ID NO 295
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 295

Pro Gly Lys Ala Ala Glu Val Arg
1 5

<210> SEQ ID NO 296
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 296

Pro Gly Lys Ala Asp Glu Val Arg
1 5

<210> SEQ ID NO 297
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 297

Pro Gly Lys Ala Asn Glu Val Arg
1 5

<210> SEQ ID NO 298
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Pro Gly Lys Ala Gln Glu Val Arg
1 5

<210> SEQ ID NO 299
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

Pro Gly Lys Ala Tyr Glu Val Arg
1 5

<210> SEQ ID NO 300

<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 300

Thr Tyr Val Met Gly Asn Glu Leu Thr Phe Leu Asp Asp
1 5 10

<210> SEQ ID NO 301
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 301

Thr Tyr Ile Met Gly Asn Glu Leu Thr Phe Leu Asp Asp
1 5 10

<210> SEQ ID NO 302
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 302

Thr Tyr Met Val Gly Asn Glu Leu Thr Phe Leu Asp Asp
1 5 10

<210> SEQ ID NO 303
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 303

Thr Tyr Met Met Glu Asn Glu Leu Thr Phe Leu Asp Asp
1 5 10

<210> SEQ ID NO 304
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 304

Thr Tyr Met Met Gly Asp Glu Leu Thr Phe Leu Asp Asp
1 5 10

<210> SEQ ID NO 305
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 305

Thr Tyr Met Met Gly Asn Glu Ser Thr Phe Leu Asp Asp 1 5 10

<210> SEQ ID NO 306
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Thr Tyr Met Met Gly Asn Glu Leu Ala Phe Leu Asp Asp
1 5 10

<210> SEQ ID NO 307
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 307

Thr Tyr Met Met Gly Asn Glu Leu Thr Phe Leu Asn Asp
1 5 10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 308

Glu Val Glu Leu Met Tyr Pro Pro Pro Tyr Tyr Leu
1 5 10

<210> SEQ ID NO 309
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Lys Val Glu Leu Met Ile Pro Pro Pro Tyr Tyr Leu
1 5 10

<210> SEQ ID NO 310
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 310

Lys Val Glu Leu Met Tyr Pro Pro Pro Tyr Tyr Gln
1 5 10

<210> SEQ ID NO 311
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 311

Lys Val Glu Leu Met Tyr Pro Pro Pro Tyr Tyr Trp
1 5 10

<210> SEQ ID NO 312
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 312

Ala Gly Lys Ala Thr Glu Val Arg
1 5

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 313

Pro Val Lys Ala Thr Glu Val Arg
1 5

<210> SEQ ID NO 314
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 314

Pro Gly Ala Ala Thr Glu Val Arg
1 5

<210> SEQ ID NO 315
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 315

Pro Gly Asp Ala Thr Glu Val Arg
1 5

<210> SEQ ID NO 316
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Pro Gly Lys Ala Thr Glu Ile Arg
1 5

<210> SEQ ID NO 317
<211> LENGTH: 8
<212> TYPE: PRT

<213> ORGANISM: Artificial Sequence
<220> FEATURE:
<223> OTHER INFORMATION: Description of Artificial Sequence: Synthetic peptide

<400> SEQUENCE: 317

Pro Arg Lys Ala Thr Glu Val Arg
1 5

<210> SEQ ID NO 318
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Pro Gly Lys Gln Thr Glu Val Arg
1 5

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 319

Pro Gly Lys Ala Arg Glu Val Arg
1 5

<210> SEQ ID NO 320
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Thr Tyr Met Met Gly Asn Glu Leu Thr Phe Leu Asp Lys
1 5 10

<210> SEQ ID NO 321
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 321

Ser Val Glu Leu Met Tyr Pro Pro Pro Tyr Tyr Leu
1 5 10

<210> SEQ ID NO 322
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 322

Lys Val Glu Leu Met Pro Pro Pro Pro Tyr Tyr Leu
1 5 10

<210> SEQ ID NO 323
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 323

Lys Val Glu Leu Met Tyr Pro Ala Pro Tyr Tyr Leu
1 5 10

<210> SEQ ID NO 324
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 324

Lys Val Glu Leu Met Tyr Pro Pro Pro Tyr Tyr Asp
1 5 10

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 325

Lys Val Glu Leu Met Tyr Pro Pro Pro Tyr Tyr Ser
1 5 10

<210> SEQ ID NO 326
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 326

Lys Val Glu Leu Met Tyr Pro Pro Pro Tyr Tyr Val
1 5 10

<210> SEQ ID NO 327
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 327

Pro Gly Lys Ala Thr Ser Val Arg
1 5

<210> SEQ ID NO 328
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 328

Pro Gly Lys Ala Thr Glu Val Ser
1 5

<210> SEQ ID NO 329
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 329

Pro Gly Ala Ala Thr Ala Val Ala
1 5

<210> SEQ ID NO 330
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 330

Pro Gly Lys Tyr Thr Glu Val Arg
1 5

<210> SEQ ID NO 331
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 331

Ser Tyr Met Met Gly Asn Glu Leu Thr Phe Leu Asp Asp
1 5 10

<210> SEQ ID NO 332
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 332

Thr Tyr Ile Met Gly Asn Glu Leu Thr Phe Leu Asp Asp
1 5 10

<210> SEQ ID NO 333
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 333

Ser Val Glu Leu Met Tyr Pro Pro Pro Tyr Tyr Leu
1 5 10

<210> SEQ ID NO 334
<211> LENGTH: 12
<212> TYPE: PRT
<213> ORGANISM: Artificial Sequence
<220> FEATURE:

<223> OTHER INFORMATION: Description of Artificial Sequence: Synthetic peptide

<400> SEQUENCE: 334

Lys Val Glu Leu Met Pro Pro Pro Pro Tyr Tyr Leu
1 5 10

<210> SEQ ID NO 335
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 335

Lys Val Glu Leu Met Tyr Pro Pro Pro Pro Tyr Leu
1 5 10

<210> SEQ ID NO 336
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 336

Ala Val Ala Leu Met Tyr Pro Pro Pro Tyr Tyr Leu
1 5 10

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 337

Lys Val Glu Leu Ala Tyr Pro Pro Pro Tyr Tyr Leu
1 5 10

<210> SEQ ID NO 338
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 338

Lys Val Glu Leu Met Ala Pro Pro Pro Tyr Tyr Leu
1 5 10

<210> SEQ ID NO 339
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 339

Lys Val Glu Leu Met Tyr Ala Pro Pro Tyr Tyr Leu
1 5 10

<210> SEQ ID NO 340

<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Lys Val Glu Leu Met Tyr Pro Ala Pro Tyr Tyr Leu
1 5 10

<210> SEQ ID NO 341
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Lys Val Glu Leu Met Tyr Pro Pro Ala Tyr Tyr Leu
1 5 10

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Lys Val Glu Leu Met Tyr Pro Pro Pro Ala Tyr Leu
1 5 10

<210> SEQ ID NO 343
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Lys Val Glu Leu Ala Ala Ala Ala Ala Ala Tyr Leu
1 5 10

<210> SEQ ID NO 344
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Lys Val Glu Leu Met Tyr Pro Pro Pro Tyr Tyr Glu
1 5 10

<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Lys Val Glu Leu Met Phe Pro Pro Pro Tyr Tyr Leu

-continued 1 5 10

<210> SEQ ID NO 346
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Pro Gly Lys Ala Gly Glu Val Arg
1 5

<210> SEQ ID NO 347
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Pro Gly Lys Ala Asn Glu Val Arg
1 5

<210> SEQ ID NO 348
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Pro Gly Lys Tyr Thr Glu Val Arg
1 5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Pro Gly Lys Leu Thr Glu Val Arg
1 5

<210> SEQ ID NO 350
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Pro Gly Lys Trp Thr Glu Val Arg
1 5

<210> SEQ ID NO 351
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Pro Gly Lys Thr Thr Glu Val Arg
1 5

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Lys Arg Gly Val Gln Glu Val Arg
1 5

<210> SEQ ID NO 353
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Tyr Thr Gly Tyr Gly Glu Val Arg
1 5

<210> SEQ ID NO 354
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Tyr Arg Asn Gln Gln Glu Val Arg
1 5

<210> SEQ ID NO 355
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

Lys Val Glu Leu Met Tyr Pro Pro Pro Tyr Tyr Glu
1 5 10

<210> SEQ ID NO 356
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Lys Val Glu Leu Met Tyr Pro Pro Pro Tyr Tyr Ser
1 5 10

<210> SEQ ID NO 357
<211> LENGTH: 12
<212> TYPE: PRT

<213> ORGANISM: Artificial Sequence
<220> FEATURE:
<223> OTHER INFORMATION: Description of Artificial Sequence: Synthetic peptide

<400> SEQUENCE: 357

Lys Val Glu Leu Met Tyr Pro Pro Pro Tyr Tyr Thr
1 5 10

<210> SEQ ID NO 358
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 358

Lys Val Glu Leu Met Tyr Pro Pro Pro Tyr Tyr Ala
1 5 10

<210> SEQ ID NO 359
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 359

Lys Val Glu Leu Met Tyr Pro Pro Pro Tyr Tyr Trp
1 5 10

<210> SEQ ID NO 360
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 360

Lys Val Glu Leu Met Tyr Pro Pro Pro Tyr Tyr Gln
1 5 10

<210> SEQ ID NO 361
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 361

Lys Val Glu Leu Met Tyr Pro Pro Pro Tyr Tyr Lys
1 5 10

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 362

Lys Val Glu Leu Met Tyr Pro Pro Pro Tyr Tyr Arg
1 5 10

<210> SEQ ID NO 363
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Lys Val Glu Leu Met Tyr Pro Pro Pro Tyr Tyr Gly
1               5                   10

<210> SEQ ID NO 364
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 364

Lys Val Glu Leu Met Tyr Pro Pro Pro Tyr Tyr Asp
1               5                   10

<210> SEQ ID NO 365
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 365

Lys Val Glu Leu Met Tyr Pro Pro Pro Tyr Tyr Glu
1               5                   10

<210> SEQ ID NO 366
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 366

Pro Tyr Asp Gly Gln Glu Val Arg
1               5

<210> SEQ ID NO 367
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 367

His Val Ser Arg Arg Glu Val Arg
1               5

<210> SEQ ID NO 368
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 368

Lys Val Glu Leu Ala Tyr Pro Pro Pro Tyr Tyr Leu
1 5 10

<210> SEQ ID NO 369
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 369

Lys Val Glu Leu Met Ala Pro Pro Pro Tyr Tyr Leu
1 5 10

<210> SEQ ID NO 370
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 370

Lys Val Glu Leu Met Tyr Ala Pro Pro Tyr Tyr Leu
1 5 10

<210> SEQ ID NO 371
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 371

Lys Val Glu Leu Met Tyr Pro Ala Pro Tyr Tyr Leu
1 5 10

<210> SEQ ID NO 372
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 372

Lys Val Glu Leu Met Tyr Pro Pro Ala Tyr Tyr Leu
1 5 10

<210> SEQ ID NO 373
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 373

Lys Val Glu Leu Met Tyr Pro Pro Pro Ala Tyr Leu
1 5 10

<210> SEQ ID NO 374
<211> LENGTH: 12
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 374

Lys Val Glu Leu Met Asp Pro Pro Pro Tyr Tyr Leu
1 5 10

<210> SEQ ID NO 375
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 375

Lys Val Glu Leu Met Glu Pro Pro Pro Tyr Tyr Leu
1 5 10

<210> SEQ ID NO 376
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 376

Lys Val Glu Leu Met Phe Pro Pro Pro Tyr Tyr Leu
1 5 10

<210> SEQ ID NO 377
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 377

Lys Val Glu Leu Met Gly Pro Pro Pro Tyr Tyr Leu
1 5 10

<210> SEQ ID NO 378
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 378

Lys Val Glu Leu Met His Pro Pro Pro Tyr Tyr Leu
1 5 10

<210> SEQ ID NO 379
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 379

Lys Val Glu Leu Met Ile Pro Pro Pro Tyr Tyr Leu
1 5 10

<210> SEQ ID NO 380

<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 380

Lys Val Glu Leu Met Lys Pro Pro Pro Tyr Tyr Leu
1 5 10

<210> SEQ ID NO 381
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 381

Lys Val Glu Leu Met Leu Pro Pro Pro Tyr Tyr Leu
1 5 10

<210> SEQ ID NO 382
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 382

Lys Val Glu Leu Met Met Pro Pro Pro Tyr Tyr Leu
1 5 10

<210> SEQ ID NO 383
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 383

Lys Val Glu Leu Met Asn Pro Pro Pro Tyr Tyr Leu
1 5 10

<210> SEQ ID NO 384
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 384

Lys Val Glu Leu Met Pro Pro Pro Pro Tyr Tyr Leu
1 5 10

<210> SEQ ID NO 385
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 385

Pro Gly Lys Tyr Thr Glu Val Arg 1 5

<210> SEQ ID NO 386
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 386

Ala Gly Lys Ala Ala Glu Val Arg
1 5

<210> SEQ ID NO 387
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Ser Gly Lys Ala Asp Glu Val Arg
1 5

<210> SEQ ID NO 388
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

Ser Gly Asn Ala Ala Lys Phe Arg
1 5

<210> SEQ ID NO 389
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 389

Pro Gly Lys Ala Tyr Glu Val Arg
1 5

<210> SEQ ID NO 390
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

Ser Gly Asn Ala Ala Glu Val Arg
1 5

<210> SEQ ID NO 391
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Pro Ser Lys Ala Thr Glu Val Arg
1 5

<210> SEQ ID NO 392
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 392

Thr Tyr Met Thr Gly Asn Glu Leu Thr Phe Leu Asp Asp
1 5 10

<210> SEQ ID NO 393
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 393

Thr Tyr Thr Val Glu Asp Glu Leu Thr Phe Leu Asp Asp
1 5 10

<210> SEQ ID NO 394
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 394

Thr Tyr Met Val Glu Asp Glu Leu Thr Phe Leu Asp Asp
1 5 10

<210> SEQ ID NO 395
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 395

Thr Tyr Thr Val Glu Asn Glu Leu Thr Ala Leu Asn Asp
1 5 10

<210> SEQ ID NO 396
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 396

Thr Tyr Met Thr Gly Asn Glu Leu Thr Phe Leu Asp Asp
1 5 10

<210> SEQ ID NO 397
<211> LENGTH: 13
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 397

Thr Tyr Thr Val Glu Asp Glu Leu Ala Phe Leu Asp Asp
1 5 10

<210> SEQ ID NO 398
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 398

Thr Tyr Thr Val Glu Asn Glu Leu Ala Phe Leu Asp Asp
1 5 10

<210> SEQ ID NO 399
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 399

Thr Tyr Val Met Gly Asn Glu Ser Thr Phe Leu Asp Asp
1 5 10

<210> SEQ ID NO 400
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 400

Thr Tyr Met Met Gly Asn Glu Ser Thr Phe Leu Asp Asp
1 5 10

<210> SEQ ID NO 401
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 401

Lys Val Glu Leu Met Gln Pro Pro Pro Tyr Tyr Leu
1 5 10

<210> SEQ ID NO 402
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 402

Lys Val Glu Leu Met Arg Pro Pro Pro Tyr Tyr Leu
1 5 10

<210> SEQ ID NO 403
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

Lys Val Glu Leu Met Ser Pro Pro Pro Tyr Tyr Leu
1 5 10

<210> SEQ ID NO 404
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Lys Val Glu Leu Met Thr Pro Pro Pro Tyr Tyr Leu
1 5 10

<210> SEQ ID NO 405
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Lys Val Glu Leu Met Val Pro Pro Pro Tyr Tyr Leu
1 5 10

<210> SEQ ID NO 406
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 406

Lys Val Glu Leu Met Trp Pro Pro Pro Tyr Tyr Leu
1 5 10

<210> SEQ ID NO 407
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 407

Lys Val Glu Leu Leu Tyr Pro Pro Pro Tyr Tyr Val
1 5 10

<210> SEQ ID NO 408
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 408

Lys Val Glu Leu Met Tyr Pro Pro Pro Tyr Tyr Val
1 5 10

<210> SEQ ID NO 409
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 409

Lys Val Glu Leu Met Tyr Pro Pro Pro Tyr Tyr Ala
1 5 10

<210> SEQ ID NO 410
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 410

Glu Val Glu Leu Met Tyr Pro Pro Pro Tyr Tyr Leu
1 5 10

<210> SEQ ID NO 411
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 411

Pro Gly Asn Ala Thr Glu Val Arg
1 5

<210> SEQ ID NO 412
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 412

Pro Gly Lys Ala Asn Glu Val Arg
1 5

<210> SEQ ID NO 413
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 413

Pro Gly Lys Ala Asn Glu Ile Arg
1 5

<210> SEQ ID NO 414
<211> LENGTH: 13
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 414

Thr Tyr Met Met Gly Asn Glu Ser Thr Phe Pro Asp Asp
1               5                   10


<210> SEQ ID NO 415
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Thr Tyr Met Met Gly Asn Glu Ser Thr Phe Leu Asp Asp
1               5                   10


<210> SEQ ID NO 416
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Thr Tyr Met Met Gly Asp Glu Leu Thr Phe Leu Asp Asp
1               5                   10


<210> SEQ ID NO 417
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Thr Tyr Met Met Glu Asn Glu Leu Thr Phe Leu Asp Asp
1               5                   10


<210> SEQ ID NO 418
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Thr Tyr Met Lys Glu Asn Glu Leu Thr Phe Leu Asp Asp
1               5                   10


<210> SEQ ID NO 419
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Thr Tyr Met Lys Glu Asp Glu Leu Thr Phe Leu Asp Asp
1               5                   10


<210> SEQ ID NO 420
```

<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 420

Thr Tyr Met Val Glu Asp Glu Leu Thr Phe Leu Asp Asp
1 5 10

<210> SEQ ID NO 421
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 421

Thr Tyr Met Lys Gly Asp Glu Leu Thr Phe Leu Asp Asp
1 5 10

<210> SEQ ID NO 422
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 422

Thr Tyr Met Lys Gly Asn Glu Leu Thr Phe Leu Asp Asp
1 5 10

<210> SEQ ID NO 423
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 423

Glu Val Glu Leu Met Tyr Pro Pro Pro Tyr Tyr Leu
1 5 10

<210> SEQ ID NO 424
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 424

Lys Val Glu Leu Met Tyr Pro Pro Pro Tyr Tyr Glu
1 5 10

<210> SEQ ID NO 425
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

Pro Gly Lys Ala Asn Glu Ile Arg 1 5

<210> SEQ ID NO 426
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 426

Pro Gly Lys Ala Thr Glu Ile Arg
1 5

<210> SEQ ID NO 427
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

Pro His Lys Ala Thr Glu Ile Arg
1 5

<210> SEQ ID NO 428
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

Pro Gly Lys Ala Asp Glu Ile Arg
1 5

<210> SEQ ID NO 429
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 429

Pro His Lys Ala Asp Glu Ile Arg
1 5

<210> SEQ ID NO 430
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 430

Pro His Lys Ala Asn Glu Ile Arg
1 5

<210> SEQ ID NO 431
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 431

Pro His Lys Ala Asn Glu Val Arg
1 5

<210> SEQ ID NO 432
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 432

Pro His Asn Ala Ala Glu Ile Arg
1 5

<210> SEQ ID NO 433
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 433

Pro His Asn Ala Asp Glu Ile Arg
1 5

<210> SEQ ID NO 434
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 434

Pro Gly Lys Ile Thr Glu Val Arg
1 5

<210> SEQ ID NO 435
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 435

Pro Gly Lys Ala Thr Glu Val Phe
1 5

<210> SEQ ID NO 436
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 436

Pro Gly Lys Tyr Thr Glu Val Arg
1 5

<210> SEQ ID NO 437
<211> LENGTH: 13
<212> TYPE: PRT

<213> ORGANISM: Artificial Sequence
<220> FEATURE:
<223> OTHER INFORMATION: Description of Artificial Sequence: Synthetic peptide

<400> SEQUENCE: 437

Thr Tyr Met Lys Gly Asp Glu Leu Thr Phe Leu Asp Asp
1               5                   10

<210> SEQ ID NO 438
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 438

Thr Tyr Met Met Gly Asp Glu Leu Thr Phe Leu Asp Asp
1               5                   10

<210> SEQ ID NO 439
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 439

Thr Tyr Met Met Glu Asp Glu Leu Thr Phe Leu Asp Asp
1               5                   10

<210> SEQ ID NO 440
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 440

Thr Tyr Met Glu Gly Asp Glu Leu Thr Phe Leu Asp Asp
1               5                   10

<210> SEQ ID NO 441
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 441

Thr Tyr Met Val Glu Asp Glu Leu Thr Phe Leu Asp Asp
1               5                   10

<210> SEQ ID NO 442
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 442

Thr Tyr Met Lys Glu Asp Glu Leu Thr Phe Leu Asp Asp
1               5                   10

<210> SEQ ID NO 443
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 443

Thr Tyr Met Glu Glu Asp Glu Leu Thr Phe Leu Asp Asp
1 5 10

<210> SEQ ID NO 444
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 444

Thr Tyr Met Val Glu Asp Glu Leu Thr Phe Leu Asp Lys
1 5 10

<210> SEQ ID NO 445
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 445

Thr Tyr Met Met Gly Asn Glu Leu Thr Phe Lys Asp Asp
1 5 10

<210> SEQ ID NO 446
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 446

Cys Tyr Met Met Gly Asn Glu Leu Thr Phe Leu Asp Asp
1 5 10

<210> SEQ ID NO 447
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 447

Lys Tyr Met Met Gly Asn Glu Leu Thr Phe Leu Asp Asp
1 5 10

<210> SEQ ID NO 448
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 448

```
Thr Tyr Met Met Gly Asn Glu Leu Thr Phe Tyr Asp Asp
1               5                   10


<210> SEQ ID NO 449
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 449

Lys Val Glu Leu Met Tyr Pro Pro Pro Tyr Tyr Glu
1               5                   10


<210> SEQ ID NO 450
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 450

Lys Val Phe Leu Met Tyr Pro Pro Pro Tyr Tyr Leu
1               5                   10


<210> SEQ ID NO 451
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 451

Lys Val Met Leu Met Tyr Pro Pro Pro Tyr Tyr Leu
1               5                   10


<210> SEQ ID NO 452
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Met His Val Ala Gln Pro Ala Val Val Leu Ala Ser Ser Arg Gly Ile
1               5                   10                  15

Ala Ser Phe Val Cys Glu Tyr Ala Ser Pro Gly His Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 453
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 453

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Thr Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 454
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 454

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys His Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 455
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 455

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Tyr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 456
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 456

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Phe Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 457
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 457

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

```
Ala Ala Thr Tyr Tyr Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 458
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Gly Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 459
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe His Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 460
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Tyr Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 461
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Met Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 462
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 462

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Gln Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 463
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 463

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ala Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 464
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 464

```
Met His Val Ala Gln Pro Ala Val Val Leu Ala Ser Ser Arg Gly Ile
1               5                   10                  15
```

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Asn Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 465
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 465

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Gln Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 466
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 466

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Ala Asp Asp Ser
    50                  55                  60

Ile Cys Thr Gly Thr Ser Ser Gly Asn Gln Val Asn Leu Thr Ile Gln
```

-continued 65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 467
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 467

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Val Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 468
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 468

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr His Gly Ile Gly Asn Gly Thr Gln Ile
100 105 110

Tyr Val Ile Asp Pro Glu Pro Cys Pro Asp Ser Asp
115 120

<210> SEQ ID NO 469
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 469

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Tyr Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 470
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 470

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Glu Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 471
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 471

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Arg Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 472
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 472

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Pro Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 473
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 473

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

```
Ala Ala Thr Tyr Met Met Gly Asn Pro Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 474
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Glu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 475
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Pro Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 476
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Tyr Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 477
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Phe Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 478
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 478

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Ile Gly Ile Gly Asn Gly Thr Gln Ile
            100                 105                 110

Tyr Val Ile Asp Pro Glu Pro Cys Pro Asp Ser Asp
        115                 120

<210> SEQ ID NO 479
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 479

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Ile Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 480
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 480

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu His Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 481
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 481

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Lys Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 482
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 482

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu His Asp Ser
50 55 60

Ile Cys Thr Gly Thr Ser Ser Gly Asn Gln Val Asn Leu Thr Ile Gln

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 483
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 483

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Trp Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 484
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 484

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Tyr Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 485
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 485

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Asp Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 486
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 486

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Trp Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 487
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 487

Met His Val Ala Gln Pro Ala Val Val Leu Ala Ser Ser Arg Gly Ile
1 5 10 15

Ala Ser Phe Val Cys Glu Tyr Ala Ser Pro Gly Lys Lys Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 488
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 488

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Asn Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 489
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 489

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

-continued

Ala Ala Thr Tyr Trp Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 490
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 490

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Lys
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 491
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 491

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Arg
85 90 95

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 492
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 492

Met His Val Ala Gln Pro Ala Val Val Leu Ala Ser Ser Arg Gly Ile
1               5                   10                  15

Ala Ser Phe Val Cys Glu Tyr Ala Ser Pro Ala Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 493
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Phe Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 494
<211> LENGTH: 124
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 494

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Thr Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 495
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Met Gly Ile Gly Asn Gly Thr Gln Ile
            100                 105                 110

Tyr Val Ile Asp Pro Glu Pro Cys Pro Asp Ser Asp
        115                 120


<210> SEQ ID NO 496
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Met His Val Ala Gln Pro Ala Val Val Leu Ala Ser Ser Arg Gly Ile
1               5                   10                  15
```

Ala Ser Phe Val Cys Glu Tyr Ala Ser Ile Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 497
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 497

Met His Val Ala Gln Pro Ala Val Val Leu Ala Ser Ser Arg Gly Ile
1 5 10 15

Ala Ser Phe Val Cys Glu Tyr Ala Ser Leu Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 498
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 498

Met His Val Ala Gln Pro Ala Val Val Leu Ala Ser Ser Arg Gly Ile
1 5 10 15

Ala Ser Phe Val Cys Glu Tyr Ala Ser Met Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln 65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 499
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 499

Met His Val Ala Gln Pro Ala Val Val Leu Ala Ser Ser Arg Gly Ile
1 5 10 15

Ala Ser Phe Val Cys Glu Tyr Ala Ser Gln Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 500
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 500

Met His Val Ala Gln Pro Ala Val Val Leu Ala Ser Ser Arg Gly Ile
1 5 10 15

Ala Ser Phe Val Cys Glu Tyr Ala Ser Thr Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 501
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 501

```
Met His Val Ala Gln Pro Ala Val Val Leu Ala Ser Ser Arg Gly Ile
1               5                   10                  15

Ala Ser Phe Val Cys Glu Tyr Ala Ser Val Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 502
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 502

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Arg Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 503
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 503

Met His Val Ala Gln Pro Ala Val Val Leu Ala Ser Ser Arg Gly Ile
1 5 10 15

Ala Ser Phe Val Cys Glu Tyr Ala Ser Pro Gly Lys Pro Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 504
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 504

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ser Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 505
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 505

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala His Glu Val
20 25 30

Arg Val Thr Val Leu Arg Gln Ala Asp Ser Gln Val Thr Glu Val Cys
35 40 45

```
Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 506
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 506

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Met Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 507
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 507

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Ser Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 508
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Glu
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 509
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 509

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Pro Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 510
<211> LENGTH: 124
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 510

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Ala Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 511
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 511

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr His Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 512
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 512

```
Met His Val Ala Gln Pro Ala Val Val Leu Ala Ser Ser Arg Gly Ile
1               5                   10                  15
```

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Met Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 513
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 513

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Trp Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 514
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 514

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Asp Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
```

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 515
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 515

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Asp Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 516
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Gly Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 517
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 517

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met His Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 518
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 518

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Leu Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 519
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 519

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Asp Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 520
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 520

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met His Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 521
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 521

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

```
Ala Ala Thr Tyr Met Met Thr Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 522
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 522

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Ala Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 523
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 523

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Phe Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 524
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Gly Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 525
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 525

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly His Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 526
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 526

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Ile Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 527
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 527

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Lys Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 528
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 528

Met His Val Ala Gln Pro Ala Val Val Leu Ala Ser Ser Arg Gly Ile
1 5 10 15

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Leu Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 529
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 529

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Met Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 530
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 530

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Gln Glu Leu Thr Phe Leu Asp Asp Ser
    50                  55                  60

Ile Cys Thr Gly Thr Ser Ser Gly Asn Gln Val Asn Leu Thr Ile Gln
```

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 531
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 531

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Arg Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 532
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Ser Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 533
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 533

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Val Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 534
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 534

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Tyr Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 535
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 535

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Ala Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 536
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 536

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Asp Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 537
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 537

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45
```

Ala Ala Thr Tyr Met Met Gly Asn His Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 538
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 538

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Lys Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 539
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 539

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Met Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 540
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 540

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Asn Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 541
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 541

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Gln Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 542
<211> LENGTH: 124
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 542

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Arg Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 543
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 543

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Ser Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 544
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 544

```
Met His Val Ala Gln Pro Ala Val Val Leu Ala Ser Ser Arg Gly Ile
1               5                   10                  15
```

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Thr Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 545
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 545

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Val Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 546
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 546

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Ile Thr Phe Leu Asp Asp Ser
50 55 60

Ile Cys Thr Gly Thr Ser Ser Gly Asn Gln Val Asn Leu Thr Ile Gln

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 547
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Arg Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 548
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 548

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Thr Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 549
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 549

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Ile Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 550
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 550

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Met Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 551
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 551

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Asn Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 552
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 552

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Gln Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 553
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 553

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Arg Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 554
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 554

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Ser Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 555
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 555

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Val Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 556
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 556

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Glu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 557
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 557

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Ile Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 558
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 558

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Met Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 559
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 559

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Thr Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 560
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 560

Met His Val Ala Gln Pro Ala Val Val Leu Ala Ser Ser Arg Gly Ile
1 5 10 15

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Val Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 561
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 561

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Arg Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 562
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 562

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Glu Ser
    50                  55                  60

Ile Cys Thr Gly Thr Ser Ser Gly Asn Gln Val Asn Leu Thr Ile Gln
```

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 563
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 563

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Gly Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 564
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 564

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp His Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 565
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 565

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Thr Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 566
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 566

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Gly Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 567
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 567

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Gly Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 568
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 568

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Ile Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 569
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 569

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Trp Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 570
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 570

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr His Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 571
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 571

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

```
Met Tyr Thr Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 572
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 572

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Leu Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 573
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 573

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Thr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 574
<211> LENGTH: 124
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 574

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Tyr Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 575
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 575

```
Met His Val Ala Gln Pro Ala Val Val Leu Ala Ser Ser Arg Gly Ile
1               5                   10                  15

Ala Ser Phe Val Cys Glu Tyr Ala Ser Asn Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 576
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 576

```
Met His Val Ala Gln Pro Ala Val Val Leu Ala Ser Ser Arg Gly Ile
1               5                   10                  15
```

Ala Ser Phe Val Cys Glu Tyr Ala Ser Pro Ile Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 577
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 577

Met His Val Ala Gln Pro Ala Val Val Leu Ala Ser Ser Arg Gly Ile
1 5 10 15

Ala Ser Phe Val Cys Glu Tyr Ala Ser Pro Gln Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 578
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 578

Met His Val Ala Gln Pro Ala Val Val Leu Ala Ser Ser Arg Gly Ile
1 5 10 15

Ala Ser Phe Val Cys Glu Tyr Ala Ser Pro Trp Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 579
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Met His Val Ala Gln Pro Ala Val Val Leu Ala Ser Ser Arg Gly Ile
1               5                   10                  15

Ala Ser Phe Val Cys Glu Tyr Ala Ser Pro Gly Glu Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 580
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 580

Met His Val Ala Gln Pro Ala Val Val Leu Ala Ser Ser Arg Gly Ile
1               5                   10                  15

Ala Ser Phe Val Cys Glu Tyr Ala Ser Pro Gly Ile Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 581
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 581

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Met Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 582
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 582

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Pro Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 583
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 583

Met His Val Ala Gln Pro Ala Val Val Leu Ala Ser Ser Arg Gly Ile
1 5 10 15

Ala Ser Phe Val Cys Glu Tyr Ala Ser Pro Gly Gln Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 584
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 584

Met His Val Ala Gln Pro Ala Val Val Leu Ala Ser Ser Arg Gly Ile
1 5 10 15

Ala Ser Phe Val Cys Glu Tyr Ala Ser Pro Gly Val Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 585
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 585

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Ile Glu Val
20 25 30

Arg Val Thr Val Leu Arg Gln Ala Asp Ser Gln Val Thr Glu Val Cys
35 40 45

```
Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 586
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 586

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Leu Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 587
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 587

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Glu Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 588
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 588

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Leu Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 589
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 589

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Asn Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 590
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 590

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Ala Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 591
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 591

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Gln Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 592
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 592

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Ser Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 593
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 593

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Asp Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 594
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 594

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Val Thr Phe Leu Asp Asp Ser
50 55 60

Ile Cys Thr Gly Thr Ser Ser Gly Asn Gln Val Asn Leu Thr Ile Gln

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 595
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 595

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu His Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 596
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 596

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Lys Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 597
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 597

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Leu Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 598
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 598

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Pro Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 599
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 599

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Asp Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 600
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 600

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Gly Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 601
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 601

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Gln Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 602
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 602

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Arg Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 603
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 603

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Ala Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 604
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 604

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Glu Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 605
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Ser Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 606
<211> LENGTH: 124
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 606

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Gln Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 607
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 607

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Ser Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 608
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 608

Met His Val Ala Gln Pro Ala Val Val Leu Ala Ser Ser Arg Gly Ile
1               5                   10                  15
```

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Arg Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 609
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 609

Met His Val Ala Gln Pro Ala Val Val Leu Ala Ser Ser Arg Gly Ile
1               5                   10                  15

Ala Ser Phe Val Cys Glu Tyr Ala Ser Arg Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 610
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 610

Met His Val Ala Gln Pro Ala Val Val Leu Ala Ser Ser Arg Gly Ile
1               5                   10                  15

Ala Ser Phe Val Cys Glu Tyr Ala Ser Pro Asp Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
```

-continued

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 611
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 611

Met His Val Ala Gln Pro Ala Val Val Leu Ala Ser Ser Arg Gly Ile
1               5                   10                  15

Ala Ser Phe Val Cys Glu Tyr Ala Ser Pro Pro Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 612
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 612

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Asn Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 613
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 613

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Lys Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 614
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 614

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Asp Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 615
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 615

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Gly Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 616
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 616

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Pro Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 617
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 617

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Arg Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 618
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 618

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Thr Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 619
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 619

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Gly
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 620
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 620

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu His
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 621
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 621

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Thr
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 622
<211> LENGTH: 124
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 622

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Glu Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 623
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 623

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Gly Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 624
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 624

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Ile Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 625
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 625

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Met Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 626
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 626

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Asn Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln

```
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 627
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Gln Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 628
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 628

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Trp Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 629
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 629

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Tyr Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 630
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 630

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Glu Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 631
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 631

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Gly Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 632
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 632

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Ile Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 633
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 633

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Val Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 634
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 634

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Ala Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 635
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 635

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Asp Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 636
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 636

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Ile Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 637
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 637

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Lys Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 638
<211> LENGTH: 124
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 638

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Leu Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 639
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 639

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Gln Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 640
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 640

```
Met His Val Ala Gln Pro Ala Val Val Leu Ala Ser Ser Arg Gly Ile
1               5                   10                  15
```

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Arg Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 641
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 641

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Ser Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 642
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 642

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Thr Met Met Gly Asn Glu Leu Thr Phe Leu Asp Asp Ser
50 55 60

Ile Cys Thr Gly Thr Ser Ser Gly Asn Gln Val Asn Leu Thr Ile Gln 65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 643
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 643

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr His Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 644
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 644

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Pro Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 645
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 645

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Ser Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 646
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 646

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Ala Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 647
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 647

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Ile Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 648
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 648

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Leu Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 649
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 649

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

```
Ala Ala Thr Tyr Met Met Asn Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 650
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 650

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gln Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 651
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 651

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Arg Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 652
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 652

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Tyr Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 653
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 653

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Gly Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 654
<211> LENGTH: 124
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 654

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Ile Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 655
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 655

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Trp Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 656
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 656

Met His Val Ala Gln Pro Ala Val Val Leu Ala Ser Ser Arg Gly Ile
1               5                   10                  15
```

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Tyr Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 657
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 657

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Asp Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 658
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 658

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Gly Phe Leu Asp Asp Ser
    50                  55                  60

Ile Cys Thr Gly Thr Ser Ser Gly Asn Gln Val Asn Leu Thr Ile Gln
```

65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 659
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 659

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Tyr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 660
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 660

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Asp Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 661
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 661

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Gly Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 662
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 662

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr His Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 663
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 663

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Leu Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 664
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 664

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Gly Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 665
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 665

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

```
Ala Ala Thr Tyr Met Met Gly Asn Glu Leu Thr Phe Leu Ile Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 666
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 666

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Trp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 667
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 667

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Ala Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 668
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 668

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Tyr Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 669
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 669

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Asp Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 670
<211> LENGTH: 124
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 670

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys His Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 671
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 671

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Asn Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 672
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 672

```
Met His Val Ala Gln Pro Ala Val Val Leu Ala Ser Ser Arg Gly Ile
1               5                   10                  15
```

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Pro Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 673
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 673

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Trp Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 674
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 674

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
```

```
65                  70                  75                  80

Gly Leu Arg Ala Met Asp Thr Gly Leu Tyr Ile Cys Lys Ala Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 675
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 675

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Asp Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 676
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 676

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys His Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 677
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 677

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Asn Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 678
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 678

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Pro Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 679
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 679

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Arg Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 680
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 680

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Thr Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 681
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 681

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

```
Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Trp Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 682
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 682

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Gly Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 683
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 683

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Ile Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 684
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 684

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Lys Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 685
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 685

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Pro Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 686
<211> LENGTH: 124
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 686

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Gln Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 687
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 687

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Arg Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 688
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 688

```
Met His Val Ala Gln Pro Ala Val Val Leu Ala Ser Ser Arg Gly Ile
1               5                   10                  15
```

-continued

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Ser Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 689
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 689

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Thr Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 690
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 690

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
```

65 70 75 80

Gly Leu Arg Ala Met Asp Thr Gly Leu Tyr Ile Cys Lys Val Val Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 691
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 691

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Tyr Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 692
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 692

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Ala
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 693
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 693

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Gly
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 694
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 694

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu His
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 695
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 695

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Met
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 696
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 696

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Pro
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 697
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 697

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Gln
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 698
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 698

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Asp Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 699
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 699

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

```
Gly Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 700
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Ile Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 701
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Asn Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 702
<211> LENGTH: 124
<212> TYPE: PRT
```

<213> ORGANISM: Artificial Sequence
<220> FEATURE:
<223> OTHER INFORMATION: Description of Artificial Sequence: Synthetic
polypeptide

<400> SEQUENCE: 702

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Ser Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 703
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 703

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Val Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 704
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 704

```
Met His Val Ala Gln Pro Ala Val Val Leu Ala Ser Ser Arg Gly Ile
1               5                   10                  15
```

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Ile Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 705
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 705

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Met Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 706
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 706

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
```

```
65                  70                  75                  80

Gly Leu Arg Ala Met Asp Thr Gly Leu Tyr Ile Cys Lys Val Glu Leu
                85                  90                  95

Met Tyr Trp Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 707
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Tyr Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 708
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro His Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 709
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 709

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Leu Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 710
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 710

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Thr Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 711
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 711

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Val Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 712
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 712

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Trp Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 713
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 713

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

```
Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Leu Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 714
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 714

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro His Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 715
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

Met Tyr Pro Pro Pro Tyr His Leu Gly Ile Gly Asn Gly Thr Gln Ile
100 105 110

Tyr Val Ile Asp Pro Glu Pro Cys Pro Asp Ser Asp
115 120

<210> SEQ ID NO 716
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 716

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Leu Leu Gly Ile Gly Asn Gly Thr Gln Ile
100 105 110

Tyr Val Ile Asp Pro Glu Pro Cys Pro Asp Ser Asp
115 120

<210> SEQ ID NO 717
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 717

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Pro Leu Gly Ile Gly Asn Gly Thr Gln Ile
100 105 110

Tyr Val Ile Asp Pro Glu Pro Cys Pro Asp Ser Asp
115 120

<210> SEQ ID NO 718
<211> LENGTH: 124
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 718

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Thr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 719
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 719

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Pro Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 720
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 720

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Ser Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 721
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 721

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Pro Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 722
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 722

```
Met His Val Ala Gln Pro Ala Val Val Leu Ala Ser Ser Arg Gly Ile
1               5                   10                  15

Ala Ser Phe Val Cys Glu Tyr Ala Ser Pro His Lys Ala Thr Glu Val
```

```
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 723
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 723

Met His Val Ala Gln Pro Ala Val Val Leu Ala Ser Ser Arg Gly Ile
1               5                   10                  15

Ala Ser Phe Val Cys Glu Tyr Ala Ser Pro Thr Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 724
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 724

Met His Val Ala Gln Pro Ala Val Val Leu Ala Ser Ser Arg Gly Ile
1               5                   10                  15

Ala Ser Phe Val Cys Glu Tyr Ala Ser Pro Gly Asn Ala Thr Glu Val
            20                  25                  30

Arg Val Thr Val Leu Arg Gln Ala Asp Ser Gln Val Thr Glu Val Cys
        35                  40                  45
```

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 725
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 725

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Met Lys Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 726
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 726

Met His Val Ala Gln Pro Ala Val Val Leu Ala Ser Ser Arg Gly Ile
1 5 10 15

Ala Ser Phe Val Cys Glu Tyr Ala Ser Pro Ser Lys Ala Thr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

```
Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 727
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 727

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Thr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 728
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 728

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Trp Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
```

```
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 729
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 729

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Gly Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 730
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 730

Met His Val Ala Gln Pro Ala Val Val Leu Ala Ser Ser Arg Gly Ile
1               5                   10                  15

Ala Ser Phe Val Cys Glu Tyr Ala Ser Pro Gly Gly Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110
```

```
Tyr Val Ile Asp Pro Glu Pro Cys Pro Asp Ser Asp
        115                 120


<210> SEQ ID NO 731
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 731

Met His Val Ala Gln Pro Ala Val Val Leu Ala Ser Ser Arg Gly Ile
1               5                   10                  15

Ala Ser Phe Val Cys Glu Tyr Ala Ser His Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 732
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 732

Met His Val Ala Gln Pro Ala Val Val Leu Ala Ser Ser Arg Gly Ile
1               5                   10                  15

Ala Ser Phe Val Cys Glu Tyr Ala Ser Lys Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 733
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 733

```
Met His Val Ala Gln Pro Ala Val Val Leu Ala Ser Ser Arg Gly Ile
1               5                   10                  15

Ala Ser Phe Val Cys Glu Tyr Ala Ser Ser Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 734
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 734

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Val Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 735
<211> LENGTH: 124
<212> TYPE: PRT

<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: see specification as filed for detailed
description of substitutions and preferred embodiments

<400> SEQUENCE: 735

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Ala Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 736
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: see specification as filed for detailed
description of substitutions and preferred embodiments

<400> SEQUENCE: 736

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asp Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 737
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide <220> FEATURE:
<223> OTHER INFORMATION: see specification as filed for detailed description of substitutions and preferred embodiments

<400> SEQUENCE: 737

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 738
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 738

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Gln Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 739
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 739

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Tyr Glu Val
20 25 30

Arg Val Thr Val Leu Arg Gln Ala Asp Ser Gln Val Thr Glu Val Cys
35 40 45

Ala Ala Thr Tyr Met Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 740
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 740

Met His Val Ala Gln Pro Ala Val Val Leu Ala Ser Ser Arg Gly Ile
1 5 10 15

Ala Ser Phe Val Cys Glu Tyr Ala Ser Pro Gly Lys Ala Thr Glu Val
20 25 30

Arg Val Thr Val Leu Arg Gln Ala Asp Ser Gln Val Thr Glu Val Cys
35 40 45

Ala Ala Thr Tyr Val Met Gly Asn Glu Leu Thr Phe Leu Asp Asp Ser
50 55 60

Ile Cys Thr Gly Thr Ser Ser Gly Asn Gln Val Asn Leu Thr Ile Gln
65 70 75 80

Gly Leu Arg Ala Met Asp Thr Gly Leu Tyr Ile Cys Lys Val Glu Leu
85 90 95

Met Tyr Pro Pro Pro Tyr Tyr Leu Gly Ile Gly Asn Gly Thr Gln Ile
100 105 110

Tyr Val Ile Asp Pro Glu Pro Cys Pro Asp Ser Asp
115 120

<210> SEQ ID NO 741
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 741

Met His Val Ala Gln Pro Ala Val Val Leu Ala Ser Ser Arg Gly Ile
1 5 10 15

```
Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Val Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 742
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 742

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Glu Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 743
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 743

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30
```

```
Arg Val Thr Val Leu Arg Gln Ala Asp Ser Gln Val Thr Glu Val Cys
        35                  40                  45

Ala Ala Thr Tyr Met Met Gly Asp Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 744
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 744

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Ser Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 745
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 745

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Ala Phe Leu Asp Asp Ser
```

```
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 746
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 746

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asn Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 747
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 747

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80
```

```
Gly Leu Arg Ala Met Asp Thr Gly Leu Tyr Ile Cys Glu Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 748
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 748

Met His Val Ala Gln Pro Ala Val Val Leu Ala Ser Ser Arg Gly Ile
1               5                   10                  15

Ala Ser Phe Val Cys Glu Tyr Ala Ser Pro Gly Asp Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 749
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 749

Met His Val Ala Gln Pro Ala Val Val Leu Ala Ser Ser Arg Gly Ile
1               5                   10                  15

Ala Ser Phe Val Cys Glu Tyr Ala Ser Ala Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 750
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 750

Met His Val Ala Gln Pro Ala Val Val Leu Ala Ser Ser Arg Gly Ile
1               5                   10                  15

Ala Ser Phe Val Cys Glu Tyr Ala Ser Pro Val Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 751
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 751

Met His Val Ala Gln Pro Ala Val Val Leu Ala Ser Ser Arg Gly Ile
1               5                   10                  15

Ala Ser Phe Val Cys Glu Tyr Ala Ser Pro Gly Ala Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
```

```
        115                 120


<210> SEQ ID NO 752
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 752

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Ile
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 753
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: see specification as filed for detailed
      description of substitutions and preferred embodiments

<400> SEQUENCE: 753

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Gly Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 754
```

<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 754

```
Met His Val Ala Gln Pro Ala Val Val Leu Ala Ser Ser Arg Gly Ile
1               5                   10                  15

Ala Ser Phe Val Cys Glu Tyr Ala Ser Pro Arg Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 755
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 755

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Gln Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 756
<211> LENGTH: 124
<212> TYPE: PRT
<213> ORGANISM: Artificial Sequence
<220> FEATURE:

<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 756

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Arg Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 757
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 757

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Lys Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 758
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: see specification as filed for detailed description of substitutions and preferred embodiments

<400> SEQUENCE: 758

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Val Gly Ile Gly Asn Gly Thr Gln Ile
            100                 105                 110

Tyr Val Ile Asp Pro Glu Pro Cys Pro Asp Ser Asp
        115                 120

<210> SEQ ID NO 759
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 759

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 760
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 760

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

-continued

```
Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120


<210> SEQ ID NO 761
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 761

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120
```